(12) United States Patent
Klaassen et al.

(10) Patent No.: US 8,399,215 B2
(45) Date of Patent: Mar. 19, 2013

(54) PENTOSE SUGAR FERMENTING CELL

(75) Inventors: Paul Klaassen, Dordrecht (NL); Jan Metske Van Der Laan, Breda (NL); Bianca Elisabeth Maria Gielesen, Maassluis (NL); Gijsberdina Pieternella Van Suylekom, 'S Gravenmoer (NL)

(73) Assignee: DSM IP Assets B.V., Heerlen (NL)

( * ) Notice: Subject to any disclaimer, the term of this patent is extended or adjusted under 35 U.S.C. 154(b) by 172 days.

(21) Appl. No.: 12/867,927

(22) PCT Filed: Mar. 5, 2009

(86) PCT No.: PCT/EP2009/052623
§ 371 (c)(1), (2), (4) Date: Aug. 17, 2010

(87) PCT Pub. No.: WO2009/109633
PCT Pub. Date: Sep. 11, 2009

(65) Prior Publication Data
US 2012/0034648 A1    Feb. 9, 2012

(30) Foreign Application Priority Data
Mar. 7, 2008 (EP) .................................... 08102407

(51) Int. Cl.
*C12P 1/00* (2006.01)
*C12N 1/00* (2006.01)
(52) U.S. Cl. ..... 435/41; 435/106; 435/132; 435/254.11; 435/254.21
(58) Field of Classification Search .................. None
See application file for complete search history.

(56) References Cited

U.S. PATENT DOCUMENTS
5,252,726 A * 10/1993 Woldike ................ 536/24.1
2008/0261287 A1    10/2008 Winkler et al.

FOREIGN PATENT DOCUMENTS
| WO | WO 03/095627 | * 11/2003 |
| WO | WO 2006/009434 | * 1/2006 |
| WO | WO 2008/000632 | 1/2008 |
| WO | WO 2008/041840 | 4/2008 |

OTHER PUBLICATIONS

Wisselink et al. Appl. Envirn. Microbiol. (Aug. 2007) 73 (15), 4881-4891.*
Written Opinion for PCT/EP2009/052623, mailed Jul. 8, 2009.
Database UniProt [Online] Oct. 23, 2007, "RecName: Full=Xylose isomerase; EC<A HEF=http://srs.ebi.ac.uk/srsbin/cgi-bin/wgetz?[enzyme-ECNumber:5.3.1.5]+-e>5.3.1.5</A?:", (whole document).
Van Maris et al., "Alcoholic fermentation of carbon sources in biomass hydrolysates by *Saccharomyces cerevisiae*" current status, *Kluwer Academic Publishers*, vol. 90, No. 4, Oct. 11, 2006, pp. 391-418.
Van Maris et al., "Development of Efficient Xylose Fermentation in *Saccharomyces cerevisiae*: Xylose Isomerase as a Key Component", *Advances in Biochemical Engineering*, vol. 108, Jan. 1, 2007, pp. 179-204.

* cited by examiner

*Primary Examiner* — Nashaat Nashed
(74) *Attorney, Agent, or Firm* — Baker Donelson Bearman Caldwell & Berkowitz, PC

(57) ABSTRACT

The invention relates to a cell which comprises a nucleotide sequence encoding a xylose isomerase, wherein the amino acid sequence of the xylose isomerase has at least about 70% sequence identity to the amino acid sequence set out in SEQ ID NO: 3 and wherein the nucleotide sequence is heterologous to the host. The cell of the invention may be used in a process for producing a fermentation product, such as ethanol. Such a process may comprise fermenting a medium containing a source of xylose with a cell of the invention such that the cell ferments xylose to the fermentation product.

32 Claims, 21 Drawing Sheets

Panel a

Panel b

Panel c

Panel a

Panel b

Panel a

Panel b

Panel a

Panel b

Panel c

Panel a

Panel b

Panel a

Panel b

SEQUENCE LISTING

```
<160> NUMBER OF SEQ ID NOS: 24

<210> SEQ ID NO 1
<211> LENGTH: 1317
<212> TYPE: DNA
<213> ORGANISM: Bacteroides uniformis

<400> SEQUENCE: 1
atggcaacaa aagagtattt tcccggaata ggaaagatta aattcgaagg taaagagagc      60
aagaacccga tggcattccg ttattacgat gccgataaag taatcatggg taagaaaatg     120
agcgaatggc tgaagttcgc catggcatgg tggcacactc tttgcgcaga aggtggtgac     180
caattcggtg gcggaacaaa gaaattcccc tggaacggtg aggctgacaa ggttcaggct     240
gccaagaaca aaatggacgc cggctttgaa ttcatgcaga aaatgggtat cgaatactac     300
tgcttccacg atgtagacct ctgcgaagaa gccgagacca ttgaagaata cgaagccaac     360
```

-continued

```
ttgaaggaaa tcgtagcgta tgccaagcag aaacaagcag aaaccggcat caaactgttg      420
tggggtactg ccaacgtatt cggccatgcc cgctacatga atggtgcagc caccaatccc      480
gatttcgatg ttgtggcacg tgccgccatc caaatcaaaa acgccatcga cgctactatc      540
gaactgggag gctcaaacta tgtattctgg ggcggtcgcg aaggctacat gtcattgctg      600
aatacagacc agaagcgtga aaagagcac ctcgcacaga tgttgaccat cgcccgcgac       660
tatgcacgtg cccgcggctt caaaggtacc ttcttgattg aaccgaaacc gatggaacct      720
acaaaacacc agtatgatgt agacaccgaa accgttatcg gcttcttgaa ggctcacaat      780
ctggacaaag atttcaaggt gaacatcgaa gtgaaccacg ctactttggc gggccacacc      840
ttcgagcacg aactcgcagt agccgtagac aacggtatgc tcggctccat cgacgccaac      900
cgtggtgact accagaacgg ctgggataca gaccagttcc ccattgacaa cttcgaactg      960
acccaggcaa tgatgcaaat catccgtaac ggaggctttg caatggcgg tacaaacttc       1020 gatgccaaga cccgtcgcaa ctccaccgac ctggaagaca ttttcattgc ccacatcgcc      1080
ggtatggacg tgatggcacg tgcactggaa agtgcagcca aactgcttga agagtctcct      1140
tacaagaaga tgctggccga ccgctatgct tccttcgaca gtggtaaagg caaggaattt      1200
gaagatggca aactgacgct ggaggatttg gtagcttacg caaaagccaa cggtgagccg      1260
aaacagacca gcggcaagca ggaattgtat gaggcaatcg tgaatatgta ctgctaa        1317
```

<210> SEQ ID NO 2
<211> LENGTH: 1318
<212> TYPE: DNA
<213> ORGANISM: Bacteroides uniformis
<220> FEATURE:
<221> NAME/KEY: CDS
<222> LOCATION: (1)..(1314)
<220> FEATURE:
<221> NAME/KEY: misc_feature
<222> LOCATION: (1)..(1314)
<223> OTHER INFORMATION: codon optimized sequence

<400> SEQUENCE: 2

```
atg gct acc aag gaa tac ttc cca ggt att ggt aag atc aaa ttc gaa      48
Met Ala Thr Lys Glu Tyr Phe Pro Gly Ile Gly Lys Ile Lys Phe Glu
1               5                  10                  15 ggt aag gaa tcc aag aac cca atg gcc ttc aga tac tac gat gct gac      96
Gly Lys Glu Ser Lys Asn Pro Met Ala Phe Arg Tyr Tyr Asp Ala Asp
            20                  25                  30 aag gtt atc atg ggt aag aag atg tct gaa tgg tta aag ttc gct atg     144
Lys Val Ile Met Gly Lys Lys Met Ser Glu Trp Leu Lys Phe Ala Met
        35                  40                  45 gct tgg tgg cat acc ttg tgt gct gaa ggt ggt gac caa ttc ggt ggt     192
Ala Trp Trp His Thr Leu Cys Ala Glu Gly Gly Asp Gln Phe Gly Gly
    50                  55                  60 ggt acc aag aaa ttc cca tgg aac ggt gaa gct gac aag gtc caa gct     240
Gly Thr Lys Lys Phe Pro Trp Asn Gly Glu Ala Asp Lys Val Gln Ala
65                  70                  75                  80 gct aag aac aag atg gac gct ggt ttc gaa ttt atg caa aag atg ggt     288
Ala Lys Asn Lys Met Asp Ala Gly Phe Glu Phe Met Gln Lys Met Gly
                85                  90                  95 att gaa tac tac tgt ttc cac gat gtt gac ttg tgt gaa gaa gct gaa     336
Ile Glu Tyr Tyr Cys Phe His Asp Val Asp Leu Cys Glu Glu Ala Glu
            100                 105                 110 acc atc gaa gaa tac gaa gct aac ttg aag gaa att gtt gct tac gct     384
Thr Ile Glu Glu Tyr Glu Ala Asn Leu Lys Glu Ile Val Ala Tyr Ala
        115                 120                 125
```

| | | |
|---|---|---|
| aag caa aag caa gct gaa act ggt atc aag cta tta tgg ggt act gct<br>Lys Gln Lys Gln Ala Glu Thr Gly Ile Lys Leu Leu Trp Gly Thr Ala<br>130                              135                         140 | | 432 |
| aac gtc ttt ggt cat gcc aga tac atg aac ggt gcc gct acc aac cca<br>Asn Val Phe Gly His Ala Arg Tyr Met Asn Gly Ala Ala Thr Asn Pro<br>145                             150                      155                    160 | | 480 |
| gat ttc gat gtt gtt gcc aga gct gcc atc caa atc aag aac gcc atc<br>Asp Phe Asp Val Val Ala Arg Ala Ala Ile Gln Ile Lys Asn Ala Ile<br>                    165                    170                    175 | | 528 |
| gat gct acc att gaa tta ggt ggt tcc aac tac gtt ttc tgg ggt ggt<br>Asp Ala Thr Ile Glu Leu Gly Gly Ser Asn Tyr Val Phe Trp Gly Gly<br>                         180                    185                    190 | | 576 |
| aga gaa ggt tac atg tcc ttg ttg aac act gac caa aag aga gaa aag<br>Arg Glu Gly Tyr Met Ser Leu Leu Asn Thr Asp Gln Lys Arg Glu Lys<br>195                              200                    205 | | 624 |
| gaa cac ttg gct caa atg ttg acc att gct cgt gac tac gct cgt gcc<br>Glu His Leu Ala Gln Met Leu Thr Ile Ala Arg Asp Tyr Ala Arg Ala<br>          210                    215                    220 | | 672 |
| aga ggt ttc aag ggt act ttc ttg att gaa cca aag cca atg gaa cca<br>Arg Gly Phe Lys Gly Thr Phe Leu Ile Glu Pro Lys Pro Met Glu Pro<br>225                              230                    235                    240 | | 720 |
| acc aag cac caa tac gat gtt gac acc gaa act gtc atc ggt ttc ttg<br>Thr Lys His Gln Tyr Asp Val Asp Thr Glu Thr Val Ile Gly Phe Leu<br>                    245                    250                    255 | | 768 |
| aag gct cac aac ttg gac aag gac ttc aag gtc aac atc gaa gtc aac<br>Lys Ala His Asn Leu Asp Lys Asp Phe Lys Val Asn Ile Glu Val Asn<br>                         260                    265                    270 | | 816 |
| cac gct act ttg gcc ggt cac act ttc gaa cac gaa ttg gct gtt gct<br>His Ala Thr Leu Ala Gly His Thr Phe Glu His Glu Leu Ala Val Ala<br>                    275                    280                    285 | | 864 |
| gtc gac aac ggt atg ttg ggt tcc att gat gct aac aga ggt gac tac<br>Val Asp Asn Gly Met Leu Gly Ser Ile Asp Ala Asn Arg Gly Asp Tyr<br>290                              295                    300 | | 912 |
| caa aac ggt tgg gac acc gac caa ttc cca atc gac aac ttt gaa ttg<br>Gln Asn Gly Trp Asp Thr Asp Gln Phe Pro Ile Asp Asn Phe Glu Leu<br>305                              310                    315                    320 | | 960 |
| act caa gct atg atg caa atc atc aga aac ggt ggt ttc ggt aac ggt<br>Thr Gln Ala Met Met Gln Ile Ile Arg Asn Gly Gly Phe Gly Asn Gly<br>                         325                    330                    335 | | 1008 |
| ggt acc aac ttc gat gct aag acc aga aga aac tct act gac ttg gaa<br>Gly Thr Asn Phe Asp Ala Lys Thr Arg Arg Asn Ser Thr Asp Leu Glu<br>                    340                    345                    350 | | 1056 |
| gat atc ttc atc gct cac att gcc ggt atg gat gtc atg gcc aga gct<br>Asp Ile Phe Ile Ala His Ile Ala Gly Met Asp Val Met Ala Arg Ala<br>                    355                    360                    365 | | 1104 |
| ttg gaa tct gct gct aaa tta ttg gaa gaa tct cct tac aag aag atg<br>Leu Glu Ser Ala Ala Lys Leu Leu Glu Glu Ser Pro Tyr Lys Lys Met<br>370                              375                    380 | | 1152 |
| ttg gct gac aga tac gct tct ttc gac tct ggt aag ggt aag gaa ttt<br>Leu Ala Asp Arg Tyr Ala Ser Phe Asp Ser Gly Lys Gly Lys Glu Phe<br>385                              390                    395                    400 | | 1200 |
| gaa gat ggt aag ttg act ttg gaa gat ttg gtt gct tac gcc aag gct<br>Glu Asp Gly Lys Leu Thr Leu Glu Asp Leu Val Ala Tyr Ala Lys Ala<br>                         405                    410                    415 | | 1248 |
| aac ggt gaa cca aag caa act tct ggt aag caa gaa ttg tac gaa gcc<br>Asn Gly Glu Pro Lys Gln Thr Ser Gly Lys Gln Glu Leu Tyr Glu Ala<br>                       420                    425                    430 | | 1296 |
| att gtc aac atg tac tgt taag<br>Ile Val Asn Met Tyr Cys<br>                  435 | | 1318 |

```
<210> SEQ ID NO 3
<211> LENGTH: 438
<212> TYPE: PRT
<213> ORGANISM: Bacteroides uniformis

<400> SEQUENCE: 3

Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asp
                20                  25                  30

Lys Val Ile Met Gly Lys Lys Met Ser Glu Trp Leu Lys Phe Ala Met
            35                  40                  45

Ala Trp Trp His Thr Leu Cys Ala Glu Gly Gly Asp Gln Phe Gly Gly
50                  55                  60

Gly Thr Lys Lys Phe Pro Trp Asn Gly Glu Ala Asp Lys Val Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Glu Glu Ala Glu
            100                 105                 110

Thr Ile Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Ile Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Gly Gly Phe Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Glu Ser Pro Tyr Lys Lys Met
370                 375                 380
```

```
Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Val Ala Tyr Ala Lys Ala
                405                 410                 415

Asn Gly Glu Pro Lys Gln Thr Ser Gly Lys Gln Glu Leu Tyr Glu Ala
            420                 425                 430

Ile Val Asn Met Tyr Cys
        435

<210> SEQ ID NO 4
<211> LENGTH: 16176
<212> TYPE: DNA
<213> ORGANISM: Artificial sequence
<220> FEATURE:
<223> OTHER INFORMATION: Synthetic DNA

<400> SEQUENCE: 4
tcgcgcgttt cggtgatgac ggtgaaaacc tcttgacaca tgcagctccc ggagacggtc      60
acagcttgtc tgtaagcgga tgccgggagc agacaagccc gtcagggcgc gtcagcgggt     120
gttggcgggt gtcggggctg gcttaactat gcggcatcag agcagattgt actgagagtg     180
caccatatgc ggtgtgaaat accgcacaga tgcgtaagga gaaaataccg catcaggcgc     240
cattcgccat tcaggctgcg caactgttgg gaagggcgat cggtgcgggc ctcttcgcta     300
ttacgccagc tggcgaaagg gggatgtgct gcaaggcgat taagttgggt aacgccaggg     360
ttttcccagt cacgacgttg taaaacgacg gccagtaagc ttgcatgcct gcaggtcgac     420
gcggccgcat attttttgta actgtaattt cactcatgca caagaaaaaa aaaactggat     480
taaaagggag cccaaggaaa actcctcagc atatatttag aagtctcctc agcatatagt     540
tgtttgtttt ctttacacat tcactgttta ataaaacttt tataatattt cattatcgga     600
actctagatt ctatacttgt ttcccaattg ggccgatcgg gccttgctgg tagtaaacgt     660
atacgtcata aaagggaaaa gccacatgcg gaagaatttt atggaaaaaa aaaaaacctc     720
gaagttacta cttctagggg gcctatcaag taaattactc ctggtacact gaagtatata     780
agggatatag aagcaaatag ttgtcagtgc aatccttcaa gacgattggg aaaatactgt     840
aggtaccgga gacctaacta catagtgttt aaagattacg atatttaact tacttagaa      900 taatgccatt ttttgagtt ataataatcc tacgttagtg tgagcgggat ttaaactgtg      960
aggaccttaa tacattcaga cacttctgcg gtatcaccct acttattccc ttcgagatta    1020
tatctaggaa cccatcaggt tggtggaaga ttacccgttc taagactttt cagcttcctc    1080
tattgatgtt acacctggac accccttttc tggcatccag ttttaatct tcagtggcat     1140 gtgagattct ccgaaattaa ttaaagcaat cacacaattc tctcggatac cacctcggtt    1200
gaaactgaca ggtggtttgt tacgcatgct aatgcaaagg agcctatata cctttggctc    1260
ggctgctgta acagggaata taagggcag cataatttag gagtttagtg aacttgcaac    1320
atttactatt ttcccttctt acgtaaatat ttttctttt aattctaaat caatcttttt    1380 caatttttg tttgtattct tttcttgctt aaatctataa ctacaaaaaa cacatacata    1440
aactaaaaat gtctgaacca gctcaaaaga acaaaaggt tgctaacaac tctctagaac     1500
aattgaaagc ctccggcact gtcgttgttg ccgacactgg tgatttcggc tctattgcca    1560
agtttcaacc tcaagactcc acaactaacc catcattgat cttggctgct gccaagcaac    1620
caacttacgc caagttgatc gatgttgccg tggaatacgg taagaagcat ggtaagacca    1680
ccgaagaaca agtcgaaaat gctgtggaca gattgttagt cgaattcggt aaggagatct    1740
```

-continued

```
taaagattgt tccaggcaga gtctccaccg aagttgatgc tagattgtct tttgacactc    1800
aagctaccat tgaaaaggct agacatatca ttaaattgtt tgaacaagaa ggtgtctcca    1860
aggaaagagt ccttattaaa attgcttcca cttgggaagg tattcaagct gccaaagaat    1920
tggaagaaaa ggacggtatc cactgtaatt tgactctatt attctccttc gttcaagcag    1980
ttgcctgtgc cgaggcccaa gttactttga tttccccatt tgttggtaga attctagact    2040
ggtacaaatc cagcactggt aaagattaca agggtgaagc cgacccaggt gttatttccg    2100
tcaagaaaat ctacaactac tacaagaagt acggttacaa gactattgtt atgggtgctt    2160 cttcagaag cactgacgaa atcaaaaact ggctggtgt tgactatcta acaatttctc     2220
cagctttatt ggacaagttg atgaacagta ctgaaccttt cccaagagtt ttggaccctg    2280
tctccgctaa gaaggaagcc ggcgacaaga tttcttacat cagcgacgaa tctaaattca    2340
gattcgactt gaatgaagac gctatggcca ctgaaaaatt gtccgaaggt atcagaaaat    2400
tctctgccga tattgttact ctattcgact tgattgaaaa gaaagttacc gcttaaggaa    2460
gtatctcgga atattaatt taggccatgt ccttatgcac gtttcttttg atacttacgg     2520
gtacatgtac acaagtatat ctatatatat aaattaatga aaatccccta tttatatata    2580
tgactttaac gagacagaac agttttttat tttttatcct atttgatgaa tgatacagtt    2640
tcttattcac gtgttatacc cacaccaaat ccaatagcaa taccggccat cacaatcact    2700
gtttcggcag cccctaagat cagacaaaac atccggaacc accttaaatc aacgtcccat    2760
atgaatcctt gcagcaaagc cgctcgtacc ggagatatac aatagaacag ataccagaca    2820
agacataatg ggctaaacaa gactcacacca attcactgc ctcattgatg gtggtacata    2880
acgaactaat actgtagccc tagacttgat agccatcatc atatcgaagt ttcactaccc    2940
tttttccatt tgccatctat tgaagtaata ataggcgcat gcaacttctt ttcttttttt    3000
ttcttttctc tctccccgt tgttgtctca ccatatccgc aatgacaaaa aaatgatgga     3060
agacactaaa ggaaaaaatt aacgacaaag acagcaccaa cagatgtcgt tgttccagag    3120
ctgatgaggg gtatctcgaa gcacacgaaa cttttttcctt ccttcattca cgcacactac    3180
tctctaatga gcaacggtat acggccttcc ttccagttac ttgaatttga aataaaaaaa    3240
agtttgctgt cttgctatca agtataaata gacctgcaat tattaatctt ttgtttcctc    3300
gtcattgttc tcgttcccctt tcttccttgt ttctttttct gcacaatatt tcaagctata    3360
ccaagcatac aatcaactat ctcatataca atgactcaat tcactgacat tgataagcta    3420
gccgtctcca cctaaagaat tttggctgtg gacaccgtat ccaaggccaa ctcaggtcac    3480
ccaggtgctc cattgggtat ggcaccagct gcacgcttc tatggagtca atgcgcatg     3540 aacccaacca acccagactg gatcaacaga gatagatttg tcttgtctaa cggtcacgcg    3600
gtcgctttgt tgtattctat gctacatttg actggttacg atctgtctat tgaagacttg    3660
aaacagttca gacagttggg ttccagaaca ccaggtcatc ctgaatttga gttgccaggt    3720
gttgaagtta ctaccggtcc attaggtcaa ggtatctcca acgctgttgg tatggccatg    3780
gctcaagcta acctggctgc cacttacaac aagcccgggct ttaccttgtc tgacaactac    3840
acctatgttt tcttgggtga cggttgtttg caagaaggta tttcttcaga agcttcctcc    3900
ttggctggtc atttgaaatt gggtaacttg attgccatct acgatgacaa caagatcact    3960
atcgatggtg ctaccagtat ctcattcgat gaagatgttg ctaagagata cgaagcctac    4020
ggttgggaag ttttgtacgt agaaaatggt aacgaagatc tagccggtat tgccaaggct    4080
attgctcaag ctaagttatc caaggacaaa ccaactttga tcaaaatgac cacaaccatt    4140
```

```
ggttacggtt ccttgcatgc cggctctcac tctgtgcacg gtgccccatt gaaagcagat    4200
gatgttaaac aactaaagag caaattcggt ttcaacccag acaagtcctt tgttgttcca    4260
caagaagttt acgaccacta ccaaaagaca attttaaagc caggtgtcga agccaacaac    4320
aagtggaaca agttgttcag cgaataccaa aagaaattcc cagaattagg tgctgaattg    4380
gctagaagat tgagcggcca actacccgca aattgggaat ctaagttgcc aacttacacc    4440
gccaaggact ctgccgtggc cactagaaaa ttatcagaaa ctgttcttga ggatgtttac    4500
aatcaattgc cagagttgat tggtggttct gccgatttaa caccttctaa cttgaccaga    4560
tggaaggaag cccttgactt ccaacctcct tcttccggtt caggtaacta ctctggtaga    4620
tacattaggt acggtattag agaacacgct atgggtgcca taatgaacgg tatttcagct    4680
ttcggtgcca actacaaacc atacggtggt actttcttga acttcgtttc ttatgctgct    4740
ggtgccgtta gattgtccgc tttgtctggc cacccagtta tttgggttgc tacacatgac    4800
tctatcggtg tcggtgaaga tggtccaaca catcaaccta ttgaaacttt agcacacttc    4860
agatccctac caaacattca agtttggaga ccagctgatg gtaacgaagt ttctgccgcc    4920
tacaagaact ctttagaatc caagcatact ccaagtatca ttgctttgtc cagacaaaac    4980
ttgccacaat tggaaggtag ctctattgaa agcgcttcta agggtggtta cgtactacaa    5040
gatgttgcta acccagatat tattttagtg gctactggtt ccgaagtgtc tttgagtgtt    5100
gaagctgcta agactttggc cgcaaagaac atcaaggctc gtgttgtttc tctaccagat    5160
ttcttcactt tgacaaaaca accctagaa tacagactat cagtcttacc agacaacgtt    5220
ccaatcatgt ctgttgaagt tttggctacc acatgttggg gcaaatacgc tcatcaatcc    5280
ttcggtattg acagatttgg tgcctccggt aaggcaccag aagtcttcaa gttcttcggt    5340
ttcaccccag aaggtgttgc tgaaagagct caaaagacca ttgcattcta aagggtgac    5400 aagctaattt ctccttttgaa aaagctttc taaattctga tcgtagatca tcagatttga    5460
tatgatatta tttgtgaaaa aatgaaataa aactttatac aacttaaata caactttttt    5520
tataaacgat taagcaaaaa aatagtttca aacttttaac aatattccaa acactcagtc    5580
cttttccttc ttatattata ggtgtacgta ttatagaaaa atttcaatga ttactttttc    5640 tttcttttc cttgtaccag cacatggccg agcttgaatg ttaaacccttt cgagagaatc    5700 acaccattca agtataaagc caataaagaa tatcgtacca gagaattttg ccatcggaca    5760
tgctacctta cgcttatatc tctcattgga atatcgtttt ctgattaaaa cacggaagta    5820
agaacttaat tcgttttttcg ttgaactatg ttgtgccagc gtaacattaa aaagagtgt    5880 acaaggccac gttctgtcac cgtcagaaaa atatgtcaat gaggcaagaa ccgggatggt    5940
aacaaaaatc acgatctggg tgggtgtggg tgtattggat tataggaagc cacgcgctca    6000
acctggaatt acaggaagct ggtaattttt tgggtttgca atcatcacca tctgcacgtt    6060
gttataatgt cccgtgtcta tatatatcca ttgacggtat tctattttt tgctattgaa    6120 atgagcgttt tttgttacta caattggttt tacagacgga attttccta tttgtttcgt    6180 cccatttttc ctttttctcat tgttctcata tcttaaaaag gtcctttctt cataatcaat    6240
gctttctttt acttaatatt ttacttgcat tcagtgaatt ttaatacata ttcctctagt    6300
cttgcaaaat cgatttagaa tcaagatacc agcctaaaaa tggtcaaacc aattatagct    6360
cccagtatcc ttgcttctga cttcgccaac ttgggttgcg aatgtcataa ggtcatcaac    6420 gccgcgcag attggttaca tatcgatgtc atggacggcc attttgttcc aaacattact    6480
ctgggccaac caattgttac ctccctacgt cgttctgtgc cacgccctgg cgatgctagc    6540
```

```
aacacagaaa agaagcccac tgcgttcttc gattgtcaca tgatggttga aaatcctgaa    6600
aaatgggtcg acgattttgc taaatgtggt gctgaccaat ttacgttcca ctacgaggcc    6660
acacaagacc ctttgcattt agttaagttg attaagtcta agggcatcaa agctgcatgc    6720
gccatcaaac ctggtacttc tgttgacgtt ttatttgaac tagctcctca tttggatatg    6780
gctcttgtta tgactgtgga acctgggttt ggaggccaaa aattcatgga agacatgatg    6840
ccaaaagtgg aaactttgag agccaagttc ccccatttga atatccaagt cgatggtggt    6900
ttgggcaagg agaccatccc gaaagccgcc aaagccggtg ccaacgttat tgtcgctgga    6960
accagtgttt tcactgcagc tgacccgcac gatgttatct ccttcatgaa agaagaagtc    7020
tcgaaggaat tgcgttctag agatttgcta gattagttgt acatatgcgg catttcttat    7080
atttatactc tctatactat acgatatggt attttttttct cgttttgatc tcctaatata    7140
cataaaccga gccattccta ctatacaaga tacgtaagtg cctaactcat gggaaaaatg    7200
ggccgcccag ggtggtgcct tgtccgtttt cgatgatcaa tccctgggat gcagtatcgt    7260
caatgacact ccataaggct tccttaacca aagtcaaaga actcttcttt tcattctctt    7320
tcactttctt accgccatct agatcaatat ccatttcgta ccccgcggaa ccgccagata    7380
ttcattactt gacgcaaaag cgtttgaaat aatgacgaaa agaaggaag aaaaaaaaag    7440 aaaaataccg cttctaggcg ggttatctac tgatccgagc ttccactagg atagcaccca    7500
aacacctgca tatttggacg accttttactt acaccaccaa aaaccacttt cgcctctccc    7560 gccccctgata acgtccacta attgagcgat tacctgagcg gtcctctttt gtttgcagca    7620
tgagacttgc atactgcaaa tcgtaagtag caacgtctca aggtcaaaac tgtatggaaa    7680
ccttgtcacc tcacttaatt ctagctagcc taccctgcaa gtcaagaggt ctccgtgatt    7740
cctagccacc tcaaggtatg cctctccccg gaaactgtgg cctttctgg cacacatgat    7800 ctccacgatt tcaacatata aatagctttt gataatggca atattaatca aatttatttt    7860
acttctttct tgtaacatct ctcttgtaat cccttattcc ttctagctat ttttcataaa    7920
aaaccaagca actgcttatc aacacacaaa cactaaatca aaatggctgc cggtgtccca    7980
aaaattgatg cgttagaatc tttgggcaat cctttggagg atgccaagag agctgcagca    8040
tacagagcag ttgatgaaaa tttaaaattt gatgatcaca aaattattgg aattggtagt    8100
ggtagcacag tggtttatgt tgccgaaaga attggacaat atttgcatga ccctaaattt    8160
tatgaagtag cgtctaaatt catttgcatt ccaacaggat tccaatcaag aaacttgatt    8220
ttggataaca agttgcaatt aggctccatt gaacagtatc ctcgcattga tatagcgttt    8280
gacggtgctg atgaagtgga tgagaattta caattaatta aggtggtgg tgcttgtcta    8340 tttcaagaaa aattggttag tactagtgct aaaaccttca ttgtcgttgc tgattcaaga    8400
aaaaagtcac caaaacattt aggtaagaac tggaggcaag gtgttcccat tgaaattgta    8460
ccttcctcat acgtgagggt caagaatgat ctattagaac aattgcatgc tgaaaaagtt    8520
gacatcagac aaggaggttc tgctaaagca ggtcctgttg taactgacaa taataacttc    8580
attatcgatg cggatttcgg tgaaatttcc gatccaagaa aattgcatag agaaatcaaa    8640
ctgttagtgg gcgtggtgga aacaggttta ttcatcgaca acgcttcaaa agcctacttc    8700
ggtaattctg acggtagtgt tgaagttacc gaaaagtgag cagatcaaag gcaaagacag    8760
aaaccgtagt aaaggttgac ttttcacaac agtgtctcca tttttatat tgtattatta    8820 aagctattta gttattgga tactgttttt tttccagaag ttttctttt agtaaagtac    8880 aatccagtaa aaatgaagga tgaacaatcg gtgtatgcag attcaacacc aataaatgca    8940
```

```
atgtttattt ctttggaacg tttgtgttgt tcgaaatcca ggataatcct tcaacaagac    9000
cctgtccgga taaggcgtta ctaccgatga cacaccaagc tcgagtaacg gagcaagaat    9060
tgaaggatat ttctgcacta aatgccaaca tcagatttaa tgatccatgg acctggttgg    9120
atggtaaatt ccccactttt gcctgatcca gccagtaaaa tccatactca acgacgatat    9180
gaacaaattt ccctcattcc gatgctgtat atgtgtataa atttttacat gctcttctgt    9240
ttagacacag aacagcttta aataaaatgt tggatatact ttttctgcct gtggtgtcat    9300
ccacgctttt aattcatctc ttgtatggtt gacaatttgg ctattttta acagaaccca    9360 acggtaattg aaattaaaag ggaaacgagt gggggcgatg agtgagtgat actaaaatag    9420
acaccaagag agcaaagcgg tcccagcggc cgcgaattcg gcgtaatcat ggtcatagct    9480
gtttcctgtg tgaaattgtt atccgctcac aattccacac aacatacgag ccggaagcat    9540
aaagtgtaaa gcctggggtg cctaatgagt gagctaactc acattaattg cgttgcgctc    9600
actgcccgct ttccagtcgg gaaacctgtc gtgccagctg cattaatgaa tcggccaacg    9660
cgcggggaga ggcggtttgc gtattgggcg ctcttccgct tcctcgctca ctgactcgct    9720
gcgctcggtc gttcggctgc ggcgagcggt atcagctcac tcaaaggcgg taatacggtt    9780
atccacagaa tcaggggata acgcaggaaa gaacatgtga gcaaaaggcc agcaaaaggc    9840
caggaaccgt aaaaaggccg cgttgctggc gtttttccat aggctccgcc ccctgacga    9900 gcatcacaaa aatcgacgct caagtcagag gtggcgaaac ccgacaggac tataaagata    9960
ccaggcgttt cccctggaa gctccctcgt gcgctctcct gttccgaccc tgccgcttac   10020
cggatacctg tccgcctttc tcccttcggg aagcgtggcg ctttctcaat gctcacgctg   10080
taggtatctc agttcggtgt aggtcgttcg ctccaagctg ggctgtgtgc acgaaccccc   10140
cgttcagccc gaccgctgcg ccttatccgg taactatcgt cttgagtcca acccggtaag   10200
acacgactta tcgccactgg cagcagccac tggtaacagg attagcagag cgaggtatgt   10260
aggcggtgct acagagttct tgaagtggtg gcctaactac ggctacacta aaggacagt    10320 atttggtatc tgcgctctgc tgaagccagt taccttcgga aaaagagttg gtagctcttg   10380
atccggcaaa caaccaccg ctggtagcgg tggtttttt gtttgcaagc agcagattac    10440
gcgcagaaaa aaaggatctc aagaagatcc tttgatcttt tctacggggt ctgacgctca   10500
gtggaacgaa aactcacgtt aagggatttt ggtcatgaga ttatcaaaaa ggatcttcac   10560
ctagatcctt ttaaattaaa aatgaagttt taaatcaatc taaagtatat atgagtaaac   10620
ttggtctgac agttaccaat gcttaatcag tgaggcacct atctcagcga tctgtctatt   10680
tcgttcatcc atagttgcct gactccccgt cgtgtagata actacgatac gggagggctt   10740
accatctggc cccagtgctg caatgatacc gcgagaccca cgctcaccgg ctccagattt   10800
atcagcaata aaccagccag ccggaagggc cgagcgcaga agtggtcctg caactttatc   10860
cgcctccatc cagtctatta attgttgccg ggaagctaga gtaagtagtt cgccagttaa   10920
tagtttgcgc aacgttgttg ccattgctac aggcatcgtg gtgtcacgct cgtcgtttgg   10980
tatggcttca ttcagctccg gttcccaacg atcaaggcga gttacatgat cccccatgtt   11040
gtgcaaaaaa gcggttagct ccttcggtcc tccgatcgtt gtcagaagta agttggccgc   11100
agtgttatca ctcatggtta tggcagcact gcataattct cttactgtca tgccatccgt   11160
aagatgcttt tctgtgactg gtgagtactc aaccaagtca ttctgagaat agtgtatgcg   11220
gcgaccgagt tgctcttgcc cggcgtcaat acgggataat accgcgccac atagcagaac   11280
tttaaaagtg ctcatcattg gaaaacgttc ttcggggcga aaactctcaa ggatcttacc   11340
```

```
gctgttgaga tccagttcga tgtaacccac tcgtgcaccc aactgatctt cagcatcttt    11400
tactttcacc agcgtttctg ggtgagcaaa acaggaagg caaaatgccg caaaaaggg      11460 aataagggcg acacggaaat gttgaatact catactcttc cttttcaat attattgaag     11520 catttatcag ggttattgtc tcatgagcgg atacatattt gaatgtattt agaaaaataa    11580
acaaataggg gttccgcgca catttccccg aaaagtgcca cctgacgtca actatacaaa    11640
tgacaagttc ttgaaaacaa gaatctttt attgtcagta ctgattagaa aaactcatcg     11700
agcatcaaat gaaactgcaa tttattcata tcaggattat caataccata tttttgaaaa    11760
agccgtttct gtaatgaagg agaaaactca ccgaggcagt tccataggat ggcaagatcc    11820
tggtatcggt ctgcgattcc gactcgtcca acatcaatac aacctattaa ttccccctcg    11880
tcaaaaataa ggttatcaag tgagaaatca ccatgagtga cgactgaatc cggtgagaat    11940
ggcaaaagct tatgcatttc tttccagact tgttcaacag gccagccatt acgctcgtca    12000
tcaaaatcac tcgcatcaac caaaccgtta ttcattcgtg attgcgcctg agcgagacga    12060
aatacgcgat cgctgttaaa aggacaatta caaacaggaa tcgaatgcaa ccggcgcagg    12120
aacactgcca gcgcatcaac aatattttca cctgaatcag gatattcttc taatacctgg    12180
aatgctgttt tgccggggat cgcagtggtg agtaaccatg catcatcagg agtacggata    12240
aaatgcttga tggtcggaag aggcataaat tccgtcagcc agtttagtct gaccatctca    12300
tctgtaacat cattggcaac gctacctttg ccatgtttca gaaacaactc tggcgcatcg    12360
ggcttcccat acaatcgata gattgtcgca cctgattgcc cgacattatc gcgagcccat    12420
ttatacccat ataaatcagc atccatgttg gaatttaatc gcggcctcga acgtgagtc    12480 ttttccttac ccatggttgt ttatgttcgg atgtgatgtg agaactgtat cctagcaaga    12540
ttttaaaagg aagtatatga agaagaacc tcagtggcaa atcctaacct tttatatttc     12600
tctacagggg cgcggcgtgg ggacaattca acgcgactgt gacgcgttct agaacacaca    12660
atatgcatgt aatcgctgat ttttttgtt ttagaagctc tatcttcagg taaaaatgag     12720
tagagaaaaa aaaacatact ggatcgatgc agaattaggg ggttattatc ctgcaggtac    12780
atgattttca gtgggaacat tgcttttag tagtccggtt ctcaacaact tgtctaagtg     12840
ttgaaaacaa aagaaatggc gtagaaacaa agtagtgtaa gtaaatctgc caatgttcta    12900
tgtataaaaa gtaaaggcaa gaagaggttc tatgcatatt tctgaaaata tctaatacac    12960
tattataatg catcaagaaa ctgtcgtatg atgaagtgcc tatgagtttt tgtgtacgtg    13020
cttctctagt atgtagccgg ttttctcttt ttacctcttt ttactactta tactactact    13080
tttactacct ttcttccacg taatctagat ctcaagccac aattcttgcc ctatgctcca    13140
acgtatacaa catcgaagaa gagtcttct ttagggagtc attggaaaag atagtatgat    13200
ggtattcgat ttacctatgt cgcaaaagaa agtccggggc aacaccacag aatgctttct    13260
ctgtactaat aacctgttgt gcgcttaacg gtctaatcgt taatcagcgg tggttaaatt    13320
tttgtaaatc taatgttcca tgattttctt tcttcaaaag gaacatgtag cgaaaatctt    13380
ttttttactt tgatacactg caattgtttc tgagcatgct gaaattttct cgatgttttt    13440
tttttttatt ggcatccaag taattaatcc ttatgctacg aaaaagttgt aggaatgaat    13500
catgcataat ctaacggata tcatcatata ctctgtgcta atattctaaa caagttcgaa    13560
aatattttct tggcccatgt aataggtggt aagtgtattg ctttgatagg aacgtcatta    13620
tcgcacaaga caatcggcac taataaccgt ttaaatatta tcatgcatgt atacatcagt    13680
atctcataga aatatacctg taagtacata cttatctaag tataaattct cgacctatgg    13740
```

```
agtcaccaca tttcccagca acttccccac ttcctctgca atcgccaacg tcctctcttc   13800
actgagtctc cgtccgataa cctgcactgc aaccggtgcc ccatggtacg cctccggatc   13860
atactcttcc tgcacgaggg catcaagctc actaaccgcc ttgaaactct cattcttctt   13920
atcgatgttc ttatccgcaa aggtaaccgg aacaaccacg ctcgtgaaat ccagcaggtt   13980
gatcacagag gcatacccat agtaccggaa ctggtcatgc cgtaccgcag cggtaggcgt   14040
aatcggcgcg atgatggcgt ccagttcctt cccggccttt tcttcagcct cccgccattt   14100
ctcaaggtac tccatctggt aattccactt ctggagatgc gtgtcccaga gctcgttcat   14160
gttaacagct ttgatgttcg ggttcagtag gtctttgata tttggaatcg ccggctcgcc   14220
ggatgcactg atatcgcgca ttacgtcggc gctgccgtca gccgcgtaga tatgggagat   14280
gagatcgtgg ccgaaatcgt gcttgtatgg cgtccacggg gtcacggtgt gaccggcttt   14340
ggcgagtgcg gcgacggtgg tttccacgcc gcgcaggata ggagggtgtg aaggacatt   14400 gccgtcgaag ttgtagtagc cgatattgag cccgccgttc ttgatcttgg aggcaataat   14460
gtccgactcg gactggcgcc agggcatggg gatgaccttg gagtcgtatt ccatggctc   14520 ctgaccgagg acggatttgg tgaagaggcg gaggtcctca acagagtgcg taatcggccc   14580
gacaacgctg tgcaccgtct cctgaccctc catgctgttc gccatctttg catacggcag   14640
ccgcccatga ctcggcctta gaccgtacag gaagttgaac gcggccggca ctcgaatcga   14700
gccaccgata tccgttccta caccgatgac gccaccacga atcccaacga tcgcaccctc   14760
accaccagaa ctgccgccgc acgaccagtt cttgttgcgt gggttgacgg tgcgcccgat   14820
gatgttgttg actgtctcgc agaccatcag ggtctgcggg acagaggtct tgacgtagaa   14880
gacggcaccg gctttgcgga gcatggttgt cagaaccgag tccccttcgt cgtacttgtt   14940
tagccatgag atgtagccca ttgatgtttc gtagcccttg actcgaagct ggtctttgag   15000
agagatgggg aggccatgga gtggaccaac gggtctcttg tgctttgcgt agtattcatc   15060
gagttccctt gcctgcgcga gagcggcgtc agggaagaac tcgtgggcgc agtttgttaa   15120
ctgctgggcg attgctgccc gtttacagaa tgctagcgta acttccaccg aggtcaactc   15180 tccgccgcc agcttggaca caagatctgc agcggaggcc tctgtgatct tcagttcggc   15240
ctctgaaagg atccccgatt tctttgggaa atcaataacg ctgtcttccg caggcagcgt   15300
ctggactttc cattcatcag ggatggtttt tgcgaggcgg gcgcgcttat cagcggccag   15360
ttcttcccag gattgaggca ttgtatatga gatagttgat tgtatgcttg gtatagcttg   15420
aaatattgtg cagaaaaaga aacaaggaag aaagggaacg agaacaatga cgaggaaaca   15480
aaagattaat aattgcaggt ctatttatac ttgatagcaa agcggcaaac tttttttatt   15540
tcaaattcaa gtaactggaa ggaaggccgt ataccgttgc tcattagaga gtagtgtgcg   15600
tgaatgaagg aaggaaaaag tttcgtgtgt tcgaagatac ccctcatcag ctctggaaca   15660
acgacatctg ttggtgctgt ctttgtcgtt aattttttcc tttagtgtct tccatcatt   15720 tttttgtcat tgcggatatg gtgagacaac aacgggggag agagaaaaga aaaaaaaga   15780 aaagaagttg catgcgccta ttattacttc aatagatggc aaatgaaaa agggtagtga   15840 aacttcgata tgatgatggc tatcaagtct agggctacag tattagttcg ttatgtacca   15900
ccatcaatga ggcagtgtaa tttgtgtagt cttgtttagc ccattatgtc ttgtctggta   15960
tctgttctat tgtatatctc ccctccgcca cctacatgtt agggagacca acgaaggtat   16020
tataggaatc ccgatgtatg ggtttggttg ccagaaaaga ggaagtccat attgtacacc   16080
cggaaacaac aaaaggatgg gcccatgacg tctaagaaac cattattatc atgacattaa   16140
```

```
cctataaaaa taggcgtatc acgaggccct ttcgtc                          16176
```

<210> SEQ ID NO 5
<211> LENGTH: 22
<212> TYPE: DNA
<213> ORGANISM: Artificial sequence
<220> FEATURE:
<223> OTHER INFORMATION: Synthetic DNA

<400> SEQUENCE: 5

```
gaaatgggcg cattactaca ag                                         22
```

<210> SEQ ID NO 6
<211> LENGTH: 22
<212> TYPE: DNA
<213> ORGANISM: Artificial sequence
<220> FEATURE:
<223> OTHER INFORMATION: Synthetic DNA

<400> SEQUENCE: 6

```
caccaacctg atgggttcct ag                                         22
```

<210> SEQ ID NO 7
<211> LENGTH: 22
<212> TYPE: DNA
<213> ORGANISM: Artificial sequence
<220> FEATURE:
<223> OTHER INFORMATION: Synthetic DNA

<400> SEQUENCE: 7

```
acgccagggt tttcccagtc ac                                         22
```

<210> SEQ ID NO 8
<211> LENGTH: 22
<212> TYPE: DNA
<213> ORGANISM: Artificial sequence
<220> FEATURE:
<223> OTHER INFORMATION: Synthetic DNA

<400> SEQUENCE: 8

```
ccagcaccct aagccgacta gg                                         22
```

<210> SEQ ID NO 9
<211> LENGTH: 21
<212> TYPE: DNA
<213> ORGANISM: Artificial sequence
<220> FEATURE:
<223> OTHER INFORMATION: Synthetic DNA

<400> SEQUENCE: 9

```
acggtgctga tgaagtggat g                                          21
```

<210> SEQ ID NO 10
<211> LENGTH: 21
<212> TYPE: DNA
<213> ORGANISM: Artificial sequence
<220> FEATURE:
<223> OTHER INFORMATION: Synthetic DNA

<400> SEQUENCE: 10

```
accacgccca ctaacagttt g                                          21
```

<210> SEQ ID NO 11
<211> LENGTH: 32
<212> TYPE: DNA
<213> ORGANISM: Artificial sequence
<220> FEATURE:

<223> OTHER INFORMATION: Synthetic DNA

<400> SEQUENCE: 11 gggggtacc ctggatggcg gcgttagtat cg                          32

<210> SEQ ID NO 12
<211> LENGTH: 32
<212> TYPE: DNA
<213> ORGANISM: Artificial sequence
<220> FEATURE:
<223> OTHER INFORMATION: Synthetic DNA

<400> SEQUENCE: 12 gggggtacc tcacagtcgc gttgaattgt cc                          32

<210> SEQ ID NO 13
<211> LENGTH: 24
<212> TYPE: DNA
<213> ORGANISM: Artificial sequence
<220> FEATURE:
<223> OTHER INFORMATION: Synthetic DNA

<400> SEQUENCE: 13
ccaaggcagc ggtacatcaa gtag                                  24

<210> SEQ ID NO 14
<211> LENGTH: 23
<212> TYPE: DNA
<213> ORGANISM: Artificial sequence
<220> FEATURE:
<223> OTHER INFORMATION: Synthetic DNA

<400> SEQUENCE: 14
tgcacatgtt gtccatcaag atg                                   23

<210> SEQ ID NO 15
<211> LENGTH: 24
<212> TYPE: DNA
<213> ORGANISM: Artificial sequence
<220> FEATURE:
<223> OTHER INFORMATION: Synthetic DNA

<400> SEQUENCE: 15
ggaaacagct atgacatgat tacg                                  24

<210> SEQ ID NO 16
<211> LENGTH: 23
<212> TYPE: DNA
<213> ORGANISM: Artificial sequence
<220> FEATURE:
<223> OTHER INFORMATION: Synthetic DNA

<400> SEQUENCE: 16
gtagcgaaat catgtattgc acc                                   23

<210> SEQ ID NO 17
<211> LENGTH: 18215
<212> TYPE: DNA
<213> ORGANISM: Artificial sequence
<220> FEATURE:
<223> OTHER INFORMATION: Synthetic DNA

<400> SEQUENCE: 17
ggccaagatg gccgatctgc attttcata ataatcctcg gtactttcta caagatcaat     60
taaattccaa tcaaaaatcg tcttttgcaa gattttgaag tcacagtact tttcattttc   120

```
aatgtcaaca gcgccccatt tgtattgtct tcctttaact ttttcgccct tttcattaaa    180
aatgtactca ttagatgcaa ttatactgaa tggatatttt tgaaaaatat cttgtgttgc    240
attcaaaact tcatcgccga aaaagaaaca tacagggata tcttgtactc ttattatttc    300
tctaacttgt gttttgaagt ttttcaattc ctctttcgtt agcaaatctg atttagcaat    360
aaccgggatt aaattcactc tcttcgctaa ttttttcatt gttacgacgt ctaaagtatc    420
aattccctta tttgaaggtc tcagaaagta caaacaacaa tggactctat tatcaaccat    480
ttttgtccta tcaggttgtt cttcttggaa aatgtacgat cttatttctt catcaatata    540
gtttctagac tgcagcccgg gatccgtcga caagcttgtg gagaggtgac ttcatgaacc    600
aagtgtctgt cgatatacaa caaaaggaa ccatttcat cttgatggac aacatgtgca    660
tcaaaaacct tatcgtaaag agttcttgga cccttggatg gagtgtaaac catgatttaa    720
aacagcaaat aataaaaatc gatagcgaca aaaactgtca atttcaatat tctttatatt    780
tgttgactgc ttagatattt tgagaaaatt cagcggaaac agcgtgatga gtgagttaag    840
ttctgctgtt taaataagta ttcaactact attgaagccg actcatgaag ccggttacgg    900
acaaaaccgg gcaaatttcg ccggtcccgg aattttcgtt tccgcaataa agaaccgct    960
catcatcata gcgccagggt agtatactat agaaggtcag actaaactga gtcatctaga  1020
gtaatgacgc cttagtagct tttacatctt cataagaaaa ggaaacttgt agaatggcct  1080
ggcgatttgt ttgctttctt gtgatgaaga aatttcgatg cgattaaccg gcaaaatcag  1140
taaaggtatt tcgcggaggc ggccttcaat catcgaatac tacgtcttaa tatgatgtac  1200
tgtggttcat attttcaagt agtgttagta aatttgtata cgttcatgta agtgtgtatc  1260
ttgagtgtct gtatgggcgc ataaacgtaa gcgagacttc caaatggagc aaacgagaag  1320
agatctttaa agtattatag aagagctggg caggaactat tatgacgtaa agccttgacc  1380
ataataaaga cgattctttg tccctctata caaacatctt gcaaagatac caaatatttt  1440
caaatcctac tcaataaaaa attaatgaat aaattagtgt gtgtgcatta tatatattaa  1500
aaattaagaa ttagactaaa taaagtgttt ctaaaaaaat attaaagttg aaatgtgcgt  1560
gttgtgaatt gtgctctatt agaataatta tgacttgtgt gcgtttcata ttttaaaata  1620
ggaaataacc aagaaagaaa aagtaccatc cagagaaacc aattatatca atcaaataa   1680
aacaaccagc ttcggtgtgt gtgtgtgtgt gaagctaaga gttgatgcca tttaatctaa  1740
aaattttaag gtgtgtgtgt ggataaaata ttagaatgac aattcgaatt gcgtaccta   1800
gtcaaaaaat tagccttta attctgctgt aacccgtaca tgcccaaaat aggggcggg   1860
ttacacagaa tatataacat cgtaggtgtc tgggtgaaca gtttattcct ggcatccact  1920
aaatataatg gagcccgctt tttaagctgg catccagaaa aaaaagaat cccagcacca   1980
aaatattgtt ttcttcacca accatcagtt cataggtcca ttctcttagc gcaactacag  2040
agaacagggg cacaaacagg caaaaaacgg gcacaacctc aatggagtga tgcaacctgc  2100
ctggagtaaa tgatgacaca aggcaattga cccacgcatg tatctatctc attttcttac  2160
accttctatt accttctgct ctctctgatt tggaaaaagc tgaaaaaaaa ggttgaaacc  2220
agttccctga aattattccc ctacttgact aataagtata taaagacggt aggtattgat  2280
tgtaattctg taaatctatt tcttaaactt cttaaattct acttttatag ttagtctttt  2340
ttttagtttt aaaacaccaa gaacttagtt tcgaataaac acacataaac aaacaaaatg  2400
ttatcagtac ctgattatga gttttggttt gttaccggtt cacaacacct ttatggtgaa  2460
gaacaattga agtctgttgc taaggatgcg caagatattg cggataaatt gaatgcaagc  2520
```

```
ggcaagttac cttataaagt agtctttaag gatgttatga cgacggctga aagtatcacc    2580
aactttatga aagaagttaa ttacaatgat aaggtagccg gtgttattac ttggatgcac    2640
acattctcac cagctaagaa ctggattcgt ggaactgaac tgttacaaaa accattatta    2700
cacttagcaa cgcaatattt gaataatatt ccatatgcag acattgactt tgattacatg    2760
aaccttaacc aaagtgccca tggcgaccgc gagtatgcct acattaacgc ccggttgcag    2820
aaacataata agattgttta cggctattgg ggcgatgaag atgtgcaaga gcagattgca    2880
cgttgggaag acgtcgccgt agcgtacaat gagagcttta agttaaggt tgctcgcttt    2940 ggcgacacaa tgcgtaatgt ggccgttact gaaggtgaca aggttgaggc tcaaattaag    3000
atgggctgga cagttgacta ttatggtatc ggtgacttag ttgaagagat caataaggtt    3060
tcggatgctg atgttgataa ggaatacgct gacttggagt ctcggtatga atggtccaa    3120 ggtgataacg atgcggacac gtataaacat tcagttcggg ttcaattggc acaatatctg    3180
ggtattaagc ggttcttaga aagaggcggt tacacagcct ttaccacgaa ctttgaagat    3240
cttgggggga tggagcaatt acctggtcta gcttcacaat tattaattcg tgatgggtat    3300
ggttttggtg ctgaaggtga ctggaagacg gctgctttag gacgggttat gaagattatg    3360
tctcacaaca agcaaaccgc ctttatggaa gactacacgt tagacttgcg tcatggtcat    3420
gaagcgatct taggttcaca catgttggaa gttgatccgt ctatcgcaag tgataaacca    3480
cgggtcgaag ttcatccatt ggatattggg ggtaaagatg atcctgctcg cctagtattt    3540
actggttcag aaggtgaagc aattgatgtc accgttgccg atttccgtga tgggttcaag    3600
atgattagct acgcggtaga tgcgaataag ccagaagccg aaacacctaa tttaccagtt    3660
gctaagcaat tatggacccc aaagatgggc ttaaagaaag gtgcactaga atggatgcaa    3720
gctggtggtg gtcaccacac gatgctgtcc ttctcgttaa ctgaagaaca aatggaagac    3780
tatgcaacca tggttggcat gactaaggca ttcttaaagt aagtgaattt actttaaatc    3840
ttgcatttaa ataaattttc tttttatagc tttatgactt agtttcaatt tatatactat    3900
tttaatgaca ttttcgattc attgattgaa agctttgtgt ttttttcttg tgcgctattg    3960
cattgttctt gtcttttttcg ccacatgtaa tatctgtagt agatacctga tacattgtgg    4020
atgctgagtg aaattttagt taataatgga ggcgctctta ataattttgg ggatattggc    4080
tttttttttt aaagtttaca aatgaatttt ttccgccagg atcgtacgcc gcggaaccgc    4140
cagatattca ttacttgacg caaaagcgtt tgaaataatg acgaaaaaga aggaagaaaa    4200
aaaaagaaaa ataccgcttc taggcgggtt atctactgat ccgagcttcc actaggatag    4260
cacccaaaca cctgcatatt tggacgacct ttacttacac caccaaaaac cactttcgcc    4320
tctcccgccc ctgataacgt ccactaattg agcgattacc tgagcggtcc tcttttgttt    4380
gcagcatgag acttgcatac tgcaaatcgt aagtagcaac gtctcaaggt caaaactgta    4440
tggaaaccct gtcacctcac ttaattctag ctagcctacc ctgcaagtca agaggtctcc    4500
gtgattccta gccacctcaa ggtatgcctc tccccggaaa ctgtggcctt ttctggcaca    4560
catgatctcc acgatttcaa catataaata gcttttgata atggcaatat taatcaaatt    4620
tattttactt cttttcttgta acatctctct tgtaatccct tattccttct agctattttt    4680
cataaaaaac caagcaactg cttatcaaca cacaaacact aaatcaaaat gaatttagtt    4740
gaaacagccc aagcgattaa aactggcaaa gtttctttag gaattgagct ggctcaact    4800 cgaattaaag ccgttttgat cacgacgat tttaatacga ttgcttcggg aagttacgtt    4860
tgggaaaacc aatttgttga tggtacttgg acttacgcac ttgaagatgt ctggaccgga    4920
```

```
attcaacaaa gttatacgca attagcagca gatgtccgca gtaaatatca catgagtttg   4980
aagcatatca atgctattgg cattagtgcc atgatgcacg gatacctagc atttgatcaa   5040
caagcgaaat tattagttcc gtttcggact tggcgtaata acattacggg gcaagcagca   5100
gatgaattga ccgaattatt tgatttcaac attccacaac ggtggagtat cgcacactta   5160
taccaggcaa tcttaaataa tgaagcgcac gttaaacagg tggacttcat aacaacgctg   5220
gctggctatg taacctggaa attgtcgggt gagaaagttc taggaatcgg tgatgcgtct   5280
ggcgttttcc caattgatga aacgactgac acatacaatc agacgatgtt aaccaagttt   5340
agccaacttg acaaagttaa accgtattca tgggatatcc ggcatatttt accgcgggtt   5400
ttaccagcgg gagccattgc tggaaagtta acggctgccg gggcgagctt acttgatcag   5460
agcggcacgc tcgacgctgg cagtgttatt gcaccgccag aaggggatgc tggaacagga   5520
atggtcggta cgaacagcgt ccgtaaacgc acgggtaaca tctcggtggg aacctcagca   5580
ttttcgatga acgttctaga taaaccattg tctaaagtct atcgcgatat tgatattgtt   5640
atgacgccag atgggtcacc agttgcaatg gtgcatgtta ataattgttc atcagatatt   5700
aatgcgtggg caacgatttt tcatgagttt gcagcccggt tgggaatgga attgaaaccg   5760
gatcgattat atgaaacgtt attcttggaa tcaactcgcg ctgatgcgga tgctggaggg   5820
ttggctaatt atagttatca atccggtgag aatattacta agattcaagc tggtcggccg   5880
ctatttgtac ggacaccaaa cagtaaattt agtttaccga actttatgtt gactcaatta   5940
tatgcggcgt tcgcaccccct ccaacttggt atggatattc ttgttaacga agaacatgtt   6000
caaacggacg ttatgattgc acagggtgga ttgttccgaa cgccggtaat tggccaacaa   6060
gtattggcca acgcactgaa cattccgatt actgtaatga gtactgctgg tgaaggcggc   6120
ccatggggga tggcagtgtt agccaacttt gcttgtcggc aaactgcaat gaacctagaa   6180
gatttcttag atcaagaagt ctttaaagag ccagaaagta tgacgttgag tccagaaccg   6240
gaacgggtgg ccggatatcg tgaatttatt caacgttatc aagctggctt accagttgaa   6300
gcagcggctg ggcaagcaat caaatattag agcttttgat taagccttct agtccaaaaa   6360
acacgttttt ttgtcattta tttcattttc ttagaatagt ttagtttatt cattttatag   6420
tcacgaatgt tttatgattc tatatagggt tgcaaacaag cattttttcat tttatgttaa   6480 aacaatttca ggtttacctt ttattctgct tgtggtgacg cgggtatccg cccgctcttt   6540
tggtcaccca tgtatttaat tgcataaata attcttaaaa gtggagctag tctatttcta   6600
tttacatacc tctcatttct catttcctcc actagtagaa aattttgcca tcggacatgc   6660
taccttacgc ttatatctct cattggaata tcgttttctg attaaaacac ggaagtaaga   6720
acttaattcg ttttttcgttg aactatgttg tgccagcgta acattaaaaa agagtgtaca   6780
aggccacgtt ctgtcaccgt cagaaaaata tgtcaatgag gcaagaaccg ggatggtaac   6840
aaaaatcacg atctgggtgg gtgtgggtgt attggattat aggaagccac gcgctcaacc   6900
tggaattaca ggaagctggt aattttttgg gtttgcaatc atcaccatct gcacgttgtt   6960
ataatgtccc gtgtctatat atatccattg acggtattct attttttttgc tattgaaatg   7020 agcgtttttt gttactacaa ttggttttac agacggaatt ttccctatttt gtttcgtccc   7080 attttttcctt ttctcattgt tctcatatct taaaaaggtc cttttcttcat aatcaatgct   7140 ttcttttact taatatttta cttgcattca gtgaattta atacatattc ctctagtctt   7200
gcaaaatcga tttagaatca agataccagc ctaaaaatgc tagaagcatt aaaacaagaa   7260
gtttatgagg ctaacatgca gcttccaaag ctgggcctgg ttacttttac ctggggcaat   7320
```

```
gtctcgggca ttgaccggga aaaaggccta ttcgtgatca agccatctgg tgttgattat    7380
ggtgaattaa aaccaagcga tttagtcgtt gttaacttac agggtgaagt ggttgaaggt    7440
aaactaaatc cgtctagtga tacgccgact catacggtgt tatataacgc ttttcctaat    7500
attggcggaa ttgtccatac tcattcgcca tgggcagttg cctatgcagc tgctcaaatg    7560
gatgtgccag ctatgaacac gacccatgct gatacgttct atggtgacgt gccggccgcg    7620
gatgcgctga ctaaggaaga aattgaagca gattatgaag gcaacacggg taaaaccatt    7680
gtgaagacgt tccaagaacg gggcctcgat tatgaagctg taccagcctc attagtcagc    7740
cagcacggcc catttgcttg gggaccaacg ccagctaaag ccgttacaa tgctaaagtg    7800 ttggaagtgg ttgccgaaga agattatcat actgcgcaat tgacccgtgc aagtagcgaa    7860
ttaccacaat atttattaga taagcattat ttacgtaagc atggtgcaag tgcctattat    7920
ggtcaaaata tgcgcattc taaggatcat gcagttcgca agtaaacaaa tcgctcttaa    7980
atatatacct aaagaacatt aaagctatat tataagcaaa gatacgtaaa ttttgcttat    8040
attattatac acatatcata tttctatatt tttaagattt ggttatataa tgtacgtaat    8100
gcaaaggaaa taaattttat acattattga acagcgtcca agtaactaca ttatgtgcac    8160
taatagttta gcgtcgtgaa gactttattg tgtcgcgaaa agtaaaaatt ttaaaaatta    8220
gagcaccttg aacttgcgaa aaaggttctc atcaactgtt taaaaacgcg tgtcttctgt    8280
gtttcagttc agggcttttc ggaggatgtg aatcgacggc gtactgtcct tgggaacttt    8340
gtctacgtat tttcacttcc tcagcgaatc cagagactat cttgggaaat tcgacaggac    8400
agtctgttga caaccgactc ccttttgact tcataataaa aattcaatga cgcaaaagga    8460
attttaggtt tttattattt attttatttat ttctgttaat tgatccttttt cttttccacta    8520 ccaacaacaa aaaggggggg aaaagatgt ataatctaaa agacactaat ctgctcttga    8580
tatccttatt atgtaatgga ataactcata taaatgtaaa atagaacttc aaattataat    8640
tataatgata gtcgaggtca gacacactta taatacatta agtaaagaaa aaaaaatgtc    8700
tgtcatcgag gtctcttttg tgtcgctaac aaaacatcac taaatacgaa gacactttgc    8760
atgggaagga tgcagcaaat ggcaaactaa cgggccattg attggtttac ctcttctatt    8820
tgtattacga ccagaaagaa cgaatggttt tcatcaatga ggtaggaaac gacctaaata    8880
taatgtagca tagataaaat cttttgtactg tatggttgca atgccttctt gattagtatc    8940
gaatttcctg aataattttg ttaatctcat tagccaaact aacgcctcaa cgaatttatc    9000
aaactttagt tcttttcctg ttccatttct gtttataaac tcagcatatt ggtcaaatgt    9060
tttctcgcta acttcaaaag gtattagata tcctagttct tgaagtgagt tatgaaattc    9120
gcttacagaa atggtgagcg atccgttgat atcattgtcc acataaactt ttctccaact    9180
tttcactctt ttgtataggg cgatgaattc tgcctggttg acagtgccaa acctggaagc    9240
accaaataaa tttatcagcg catctactga tgatatacaa aaatgggagt tgtcgtcgtt    9300
ttgtagtaag ttctgtagtt cctcagctgt cagtcggttt ttgcccttta catcatggtt    9360
atgaaatagc tgtgtggcca cttgcatgtc tcgtacatct tctctgctat cgaacgaagc    9420
aggtgcaact ttcttcaaga gttgtgcagg cactgcttga ttgtgaatta ggggaggagg    9480
agaggaagct atccgttgag cggaagtgtt caagttgtta taatgggttg gcgctggagg    9540
tataggcctg cctgctggtt tctgtgcgat aacattatat ctaggatcca caggtgtttt    9600
cgtatgtctt ggagaataac tttggggaga accataggag tggtgaccgt tttctgctct    9660 gttttttgtta tattgagttt gtaagggaat tggagctgag tggactctag tgttgggagt    9720
```

```
ttgtgcttga gtaaccggta ccacggctcc tcgctgcaga cctgcgagca gggaaacgct   9780
cccctcacag tcgcgttgaa ttgtccccac gccgcgcccc tgtagagaaa tataaaaggt   9840
taggatttgc cactgaggtt cttctttcat atacttcctt ttaaaatctt gctaggatac   9900
agttctcaca tcacatccga acataaacaa ccatgggtaa ggaaaagact cacgtttcga   9960
ggccgcgatt aaattccaac atggatgctg atttatatgg gtataaatgg gctcgcgata  10020
atgtcgggca atcaggtgcg acaatctatc gattgtatgg gaagcccgat gcgccagagt  10080
tgtttctgaa acatggcaaa ggtagcgttg ccaatgatgt tacagatgag atggtcagac  10140
taaactggct gacggaattt atgcctcttc cgaccatcaa gcattttatc cgtactcctg  10200
atgatgcatg gttactcacc actgcgatcc ccggcaaaac agcattccag gtattagaag  10260
aatatcctga ttcaggtgaa atattgttg atgcgctggc agtgttcctg cgccggttgc  10320
attcgattcc tgtttgtaat tgtcctttta acagcgatcg cgtatttcgt ctcgctcagg  10380
cgcaatcacg aatgaataac ggtttggttg atgcgagtga ttttgatgac gagcgtaatg  10440
gctggcctgt tgaacaagtc tggaaagaaa tgcataagct tttgccattc tcaccggatt  10500
cagtcgtcac tcatggtgat ttctcacttg ataaccttat ttttgacgag gggaaattaa  10560
taggttgtat tgatgttgga cgagtcggaa tcgcagaccg ataccaggat cttgccatcc  10620
tatggaactg cctcggtgag ttttctcctt cattacagaa acggcttttt caaaaatatg  10680
gtattgataa tcctgatatg aataaattgc agtttcattt gatgctcgat gagttttct  10740
aatcagtact gacaataaaa agattcttgt tttcaagaac ttgtcatttg tatagttttt  10800
ttatattgta gttgttctat tttaatcaaa tgttagcgtg atttatattt tttttcgcct  10860
cgacatcatc tgcccagatg cgaagttaag tgcgcagaaa gtaatatcat gcgtcaatcg  10920
tatgtgaatg ctggtcgcta tactgctgtc gattcgatac taacgccgcc atccagggta  10980
ccatcctttt gttgtttccg ggtgtacaat atggacttcc tcttttctgg caaccaaacc  11040
catacatcgg gattcctata ataccttcgt tggtctccct aacatgtagg tggcggaggg  11100
gagatataca atagaacaga taccagacaa gacataatgg gctaaacaag actacaccaa  11160
ttacactgcc tcattgatgg tggtacataa cgaactaata ctgtagccct agacttgata  11220
gccatcatca tatcgaagtt tcactaccct ttttccattt gccatctatt gaagtaataa  11280
taggcgcatg caacttcttt tcttttttt tcttttctct ctccccgtt gttgtctcac  11340
catatccgca atgacaaaaa aaatgatgga agacactaaa ggaaaaaatt aacgacaaag  11400
acagcaccaa cagatgtcgt tgttccagag ctgatgaggg gtatcttcga acacacgaaa  11460
cttttttcctt ccttcattca cgcacactac tctctaatga gcaacggtat acggccttcc  11520
ttccagttac ttgaatttga aataaaaaaa gtttgccgct ttgctatcaa gtataaatag  11580
acctgcaatt attaatcttt tgtttcctcg tcattgttct cgttcccttt cttccttgtt  11640
tcttttttctg cacaatattt caagctatac caagcataca atcaactatc tcatatacaa  11700
tgcctcaatc ctgggaagaa ctggccgctg ataagcgcgc ccgcctcgca aaaccatcc  11760
ctgatgaatg gaaagtccag acgctgcctg cggaagacag cgttattgat ttcccaaaga  11820
aatcggggat cctttcagag gccgaactga agatcacaga ggcctccgct gcagatcttg  11880
tgtccaagct ggcggccgga gagttgacct cggtggaagt tacgctagca ttctgtaaac  11940
gggcagcaat cgcccagcag ttaacaaact gcgcccacga gttcttccct gacgccgctc  12000
tcgcgcaggc aagggaactc gatgaatact acgcaaagca caagagaccc gttggtccac  12060
tccatggcct ccccatctct ctcaaagacc agcttcgagt caagggctac gaaacatcaa  12120
```

```
tgggctacat ctcatggcta aacaagtacg acgaagggga ctcggttctg acaaccatgc   12180
tccgcaaagc cggtgccgtc ttctacgtca agacctctgt cccgcagacc ctgatggtct   12240
gcgagacagt caacaacatc atcgggcgca ccgtcaaccc acgcaacaag aactggtcgt   12300
gcggcggcag ttctggtggt gagggtgcga tcgttgggat tcgtggtggc gtcatcggtg   12360
taggaacgga tatccggtggc tcgattcgag tgccggccgc gttcaacttc ctgtacggtc   12420
taaggccgag tcatgggcgg ctgccgtatg caaagatggc gaacagcatg gagggtcagg   12480
agacggtgca cagcgttgtc gggccgatta cgcactctgt tgaggacctc cgcctcttca   12540
ccaaatccgt cctcggtcag gagccatgga aatacgactc caaggtcatc cccatgccct   12600
ggcgccagtc cgagtcggac attattgcct ccaagatcaa gaacggcggg ctcaatatcg   12660
gctactacaa cttcgacggc aatgtccttc cacaccctcc tatcctgcgc ggcgtggaaa   12720
ccaccgtcgc cgcactcgcc aaagccggtc acaccgtgac cccgtggacg ccatacaagc   12780
acgatttcgg ccacgatctc atctcccata tctacgcggc tgacggcagc gccgacgtaa   12840
tgcgcgatat cagtgcatcc ggcgagccgg cgattccaaa tatcaaagac ctactgaacc   12900
cgaacatcaa agctgttaac atgaacgagc tctgggacac gcatctccag aagtggaatt   12960
accagatgga gtaccttgag aaatggcggg aggctgaaga aaaggccggg aaggaactgg   13020
acgccatcat cgcgccgatt acgcctaccg ctgcggtacg gcatgaccag ttccggtact   13080
atgggtatgc ctctgtgatc aacctgctgg atttcacgag cgtggttgtt ccggttacct   13140
ttgcggataa gaacatcgat aagaagaatg agagtttcaa ggcggttagt gagcttgatg   13200
ccctcgtgca ggaagagtat gatccggagg cgtaccatgg ggcaccggtt gcagtgcagg   13260
ttatcggacg gagactcagt gaagagagga cgttggcgat tgcagaggaa gtggggaagt   13320
tgctgggaaa tgtggtgact ccataggtcg agaatttata cttagataag tatgtactta   13380
caggtatatt tctatgagat actgatgtat acatgcatga taatatttaa acggttatta   13440
gtgccgattg tcttgtgcga taatgacgtt cctatcaaag caatacactt accacctatt   13500
acatgggcca agaaaatatt ttcgaacttg tttagaatat tagcacagag tatatgatga   13560
tatccgttag attatgcatg attcattcct acaacttttt cgtagcataa ggattaatta   13620
cttggatgcc aataaaaaaa aaaaacatcg agaaatttc agcatgctca gaaacaattg   13680
cagtgtatca aagtaaaaaa aagatttcg ctacatgttc cttttgaaga aagaaaatca   13740
tggaacatta gatttacaaa aatttaacca ccgctgatta acgattagac cgttaagcgc   13800
acaacaggtt attagtacag agaaagcatt ctgtggtgtt gccccggact ttcttttgcg   13860
acataggtaa atcgaatacc atcatactat cttttccaat gactccctaa agaaagactc   13920
ttcttcgatg ttgtatacgt tggagcatag ggcaagaatt gtggcttgag atctagatta   13980
cgtggaagaa aggtagtaaa agtagtagta taagtagtaa aaagaggtaa aaagagaaaa   14040
ccggctacat actagagaag cacgtacaca aaaactcata ggcacttcat catacgcacg   14100
tttcttgatg cattataata gtgtattaga tattttcaga aatatgcata gaacctcttc   14160
ttgcctttac tttttataca tagaacattg gcagatttac ttacactact ttgtttctac   14220
gccatttctt ttgttttcaa cacttagaca agttgttgag aaccggacta ctaaaaagca   14280
atgttcccac tgaaaatcat gtacctgcag gataataacc ccctaattct gcatcgatcc   14340
agtatgtttt tttttctcta ctcatttta cctgaagata gagcttctaa aacaaaaaaa   14400
atcagcgatt acatgcatat tgtgtgttct agaattgcgg atcaccagat cgccattaca   14460
atgtatgcag gcaaatattt ctcagaatga aaatagaga aaggaaacg aaaattctgt   14520
```

```
aagatgcctt cgaagagatt tctcgatatg caaggcgtgc atcagggtga tccaaaggaa    14580
ctcgagagag agggcgaaag gcaatttaat gcattgcttc tccattgact tctagttgag    14640
cggataagtt cggaaatgta agtcacagct aatgacaaat ccactttagg tttcgaggca    14700
ctatttaggc aaaaagacga gtggggaaat aacaaacgct caaacatatt agcatatacc    14760
ttcaaaaaat gggaatagta tataaccttc cggttcgtta ataaatcaaa tctttcatct    14820
agttctctta agatttcaat attttgcttt cttgaagaaa gaatctactc tcctccccca    14880
ttcgcactgc aaagctagct tggcactggc cgtcgtttta caacgtcgtg actgggaaaa    14940
ccctggcctt acccaactta atcgccttgc agcacatccc cctttcgcca gctggcgtaa    15000
tagcgaagag gcccgcaccg atcgcccttc ccaacagttg cgcagcctga atggcgaatg    15060
ggaaattgta acgttaata ttttgttaaa attgcgcgtta aattttttgtt aaatcagctc    15120 attttttaac caataggccg aaatcggcaa aatcccttat aaatcaaaag aatagaccga    15180
gatagggttg agtgttgttc cagttttggaa caagagtcca ctattaaaga acgtggactc    15240
caacgtcaaa gggcgaaaaa ccgtctatca gggcgatggc ccactacgtg aaccatcacc    15300
ctaatcaagt ttttttgggt cgaggtgccg taaagcacta atcggaacc ctaaagggag    15360 cccccgattt agagcttgac ggggaaagcc ggcgaacgtg gcgagaaagg aagggaagaa    15420
agcgaaagga gcgggcgcta gggcgctggc aagtgtagcg gtcacgctgc gcgtaaccac    15480 cacaccgcc gcgcttaatg cgccgctaca gggcgcgtca ggtggcactt tcggggaaa     15540 tgtgcgcgga accctatttt gtttattttt ctaaatacat tcaaatatgt atccgctcat    15600
gagacaataa ccctgataaa tgcttcaata atattgaaaa aggaagagta tgagtattca    15660
acatttccgt gtcgccctta ttcccttttt tgcggcattt tgccttcctg ttttttgctca   15720 cccagaaacg ctggtgaaag taaaagatgc tgaagatcag ttgggtgcac gagtgggtta    15780
catcgaactg gatctcaaca gcggtaagat ccttgagagt tttcgccccg aagaacgttt    15840
tccaatgatg agcacttttta aagttctgct atgtggcgcg gtattatccc gtattgacgc    15900
cgggcaagac caactcggtc gccgcataca ctattctcag aatgacttgg ttgagtactc    15960
accagtcaca gaaaagcatc ttacggatgg catgacagta agagaattat gcagtgctgc    16020
cataaccatg agtgataaca ctgcggccaa cttacttctg acaacgatcg gaggaccgaa    16080
ggagctaacc gcttttttgc acaacatggg ggatcatgta actcgccttg atcgttggga    16140
accggagctg aatgaagcca taccaaacga cgagcgtgac accacgatgc ctgtagcaat    16200
ggcaacaacg ttgcgcaaac tattaactgg cgaactactt agtctagctt cccggcaaca    16260
attaatagac tggatggagg cggataaagt tgcaggacca cttctgcgct cggcccttcc    16320
ggctggctgg tttattgctg ataaatctgg agccggtgag cgtgggtctc gcggtatcat    16380
tgcagcactg gggccagatg gtaagccctc ccgtatcgta gttatctaca cgacggggag    16440
tcaggcaact atggatgaac gaaatagaca gatcgctgag ataggtgcct cactgattaa    16500
gcattggtaa ctgtcagacc aagtttactc atatatactt tagattgatt taaaacttca    16560
tttttaattt aaaaggatct aggtgaagat cctttttgat aatctcatga ccaaaatccc    16620
ttaacgtgag ttttcgttcc actgagcgtc agaccccgta gaaaagatca aggatcttc    16680 ttgagatcct ttttttctgc gcgtaatctg ctgcttgcaa acaaaaaaac caccgctacc    16740
agcggtggtt tgtttgccgg atcaagagct accacctctt tttccgaagg taactggctt    16800
cagcagagcg cagataccaa atactgtcct tctagtgtag ccgtagttag gccaccactt    16860
caagaactct gtagcaccgc ctacatacct cgctctgcta atcctgttac cagtggctgc    16920
```

```
tgccagtggc gataagtcgt gtcttaccgg gttggactca agacgatagt taccggataa    16980
ggcgcagcgg tcgggctgaa cgggggggttc gtgcacacag cccagcttgg agcgaacgac    17040
ctacaccgaa ctgagatacc tacagcgtga gcattgagaa agcgccacgc ttcccgaagg    17100
gagaaaggcg gacaggtatc cggtaagcgg cagggtcgga acaggagagc gcacgaggga    17160
gcttccaggg ggaaacgcct ggtatcttta tagtcctgtc gggtttcgcc acctctgact    17220
tgagcgtcga ttttgtgat gctcgtcagg ggggcggagc ctatggaaaa acgccagcaa    17280
cgcggccttt ttacggttcc tggccttttg ctggcctttt gctcacatgt tctttcctgc    17340
gttatcccct gattctgtgg ataaccgtat taccgccttt gagtgagctg ataccgctcg    17400
ccgcagccga acgaccgagc gcagcgagtc agtgagcgag gaagcggaag agcgcccaat    17460
acgcaaaccg cctctccccg cgcgttggcc gattcattaa tgcagctggc acgacaggtt    17520
tcccgactgg aaagcgggca gtgagcgcaa cgcaattaat gtgagttagc tcactcatta    17580
ggcaccccag gctttacact ttatgcttcc ggctcgtatg ttgtgtggaa ttgtgagcgg    17640
ataacaattt cacacaggaa acagctatga catgattacg aatttaatac gactcacaat    17700
agggaattag cttgcgcgaa attattggct tttttttttt tttaattaat actacctttt    17760
gatgtgaacg tttactaaag tagcactatc tgtggaatgg ctgttggaac tttttccgat    17820
taacagcttg tattccaagt cctgacattc cagttgtaag ttttccaact tgtgattcaa    17880
ttgttcaatc tcttggttaa aattctcttg ttccatgaat aggctctttt tccagtctcg    17940
aaattttgaa atttctctgt tggacagctc gttgaatttt ttcttagctt ctaattgtct    18000
agttataaat tcaggatccc attctgtagc caccttatcc atgaccgttt tattaattat    18060
ttcatagcac ttgtaatttt tgagtttgtt ttcctcgatt tcatcgaagt tcatttcttc    18120
ctccaaaaat ttcctttgtt cttccgttat gtcaacactt ttcgttgtta agcaatctct    18180
ggcctttaat agcctagttc ttagcatttc agatc                               18215
```

<210> SEQ ID NO 18
<211> LENGTH: 23
<212> TYPE: DNA
<213> ORGANISM: Artificial sequence
<220> FEATURE:
<223> OTHER INFORMATION: Synthetic DNA

<400> SEQUENCE: 18
tgatcttgta gaaagtaccg agg                                              23

<210> SEQ ID NO 19
<211> LENGTH: 25
<212> TYPE: DNA
<213> ORGANISM: Artificial sequence
<220> FEATURE:
<223> OTHER INFORMATION: Synthetic DNA

<400> SEQUENCE: 19
ctttgttctt ccgttatgtc aacac                                            25

<210> SEQ ID NO 20
<211> LENGTH: 23
<212> TYPE: DNA
<213> ORGANISM: Artificial sequence
<220> FEATURE:
<223> OTHER INFORMATION: Synthetic DNA

<400> SEQUENCE: 20
ttccaagaag aacaacctga tag                                              23

```
<210> SEQ ID NO 21
<211> LENGTH: 21
<212> TYPE: DNA
<213> ORGANISM: Artificial sequence
<220> FEATURE:
<223> OTHER INFORMATION: Synthetic DNA

<400> SEQUENCE: 21
tgatgtgaac gtttactaaa g                                               21

<210> SEQ ID NO 22
<211> LENGTH: 32
<212> TYPE: DNA
<213> ORGANISM: Artificial Sequence
<220> FEATURE:
<223> OTHER INFORMATION: sequence placed in front of xylose isomerase
      coding sequence

<400> SEQUENCE: 22
actagtaaaa acacatacat aaactaaaaa tg                                   32

<210> SEQ ID NO 23
<211> LENGTH: 49
<212> TYPE: DNA
<213> ORGANISM: Artificial Sequence
<220> FEATURE:
<223> OTHER INFORMATION: original TPI1 promoter

<400> SEQUENCE: 23
tcttgcttaa atctataact acaaaaaaca catacataaa ctaaaaatg                 49

<210> SEQ ID NO 24
<211> LENGTH: 49
<212> TYPE: DNA
<213> ORGANISM: Artificial Sequence
<220> FEATURE:
<223> OTHER INFORMATION: TPI1 promoter containing SpeI restriction site
      (ACTAGT)

<400> SEQUENCE: 24
tcttgcttaa atctataact agtaaaaaca catacataaa ctaaaaatg                 49
```

PENTOSE SUGAR FERMENTING CELL

This application is the U.S. national phase of International Application No. PCT/EP2009/052623 filed 5 Mar. 2009 which designated the U.S. and claims priority to EP Patent Application No. 08102407.7 filed 7 Mar. 2008, the entire contents of each of which are hereby incorporated by reference.

FIELD OF THE INVENTION

The present invention relates to a cell which is capable of isomerising xylose to xylulose. The invention also relates to a process in which such cells are used for the production of a fermentation product, such as ethanol.

BACKGROUND OF THE INVENTION

Large-scale consumption of traditional, fossil fuels (petroleum-based fuels) in recent decades has contributed to high levels of pollution. This, along with the realisation that the world stock of fossil fuels is not limited and a growing environmental awareness, has stimulated new initiatives to investigate the feasibility of alternative fuels such as ethanol, which is a particulate-free burning fuel source that releases less $CO_2$ than unleaded gasoline on a per liter basis.

Although biomass-derived ethanol may be produced by the fermentation of hexose sugars obtained from many different sources, the substrates typically used for commercial scale production of fuel alcohol, such as cane sugar and corn starch, are expensive. Increases in the production of fuel ethanol will therefore require the use of lower-cost feedstocks.

Currently, only lignocellulosic feedstock derived from plant biomass is available in sufficient quantities to substitute the crops currently used for ethanol production. In most lignocellulosic material, the second-most-common sugar, after glucose, is xylose. Thus, for an economically feasible fuel production process, both hexose and pentose sugars must be fermented to form ethanol. The yeast *Saccharomyces cerevisiae* is robust and well adapted for ethanol production, but it is unable to produce ethanol using xylose as a carbon source. Also, no naturally-occurring organisms are known which can ferment xylose to ethanol with both a high ethanol yield and a high ethanol productivity.

There is therefore a need for an organism possessing these properties so as to enable the commercially-viable production of ethanol from lignocellulosic feedstocks.

SUMMARY OF THE INVENTION

According to the invention, there is provided a cell that is capable of fermentation, such as alcoholic fermentation, and of using xylose as a carbon source. Such a cell comprises a nucleotide sequence encoding a xylose isomerase, wherein the amino acid sequence of the xylose isomerase has at least about 70% sequence identity to the amino acid sequence set out in SEQ ID NO: 3 and wherein the nucleotide sequence is heterologous to the host. Such a cell produces a higher amount of ethanol when using xylose as a carbon source as compared to the wild type filamentous fungus.

The invention also provides:
a process for producing a fermentation product which process comprises fermenting a medium containing a source of xylose with a cell of the invention such that the cell ferments xylose to the fermentation product;
a process for producing a fermentation product which process comprises fermenting a medium containing at least a source of xylose and a source of L-arabinose with a cell as defined of the invention which is also capable of utilizing L-arabinose such that the cell ferments xylose and L-arabinose to the fermentation product; and
a process for producing a fermentation product which process comprises fermenting a medium containing at least a source of xylose and a source of L-arabinose with a cell of the invention and a cell able to use L-arabinose, whereby each cell ferments xylose and/or arabinose to the fermentation product.

The invention further provides the use of a cell of the invention in a process for the production of a fermentation product.

Panel a: XcmI-digestion of chromosomal DNA preparations, hybridized with the RKI1-probe. Lane 1: CEN.PK113-7D; lane 2: BIE104F1; lane 3: BIE104P1

Panel b: PsiI-digestion of chromosomal DNA preparations, hybridized with the RKI1-probe. Lane 1: CEN.PK113-7D; lane 2: BIE104F1; lane 3: BIE104P1

ΔGRE3::PPP stands for the replacement of the coding region of the GRE3-gene by the cassette containing the genes TAL1, TKL1, RKI1 and RPE1 under control of strong constitutive promoters, ΔGRE3::[TPI1p-TAL1-ADH1p-TKL1-PGI1p-RPE1-ENO1p-RKI1].

Figure 5:
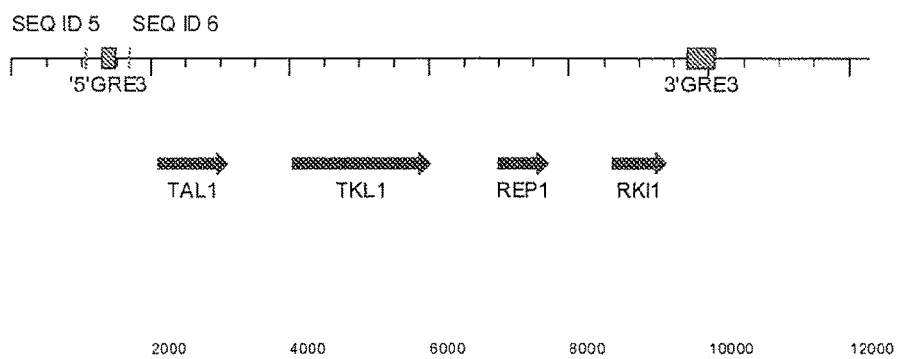
Figure 5:
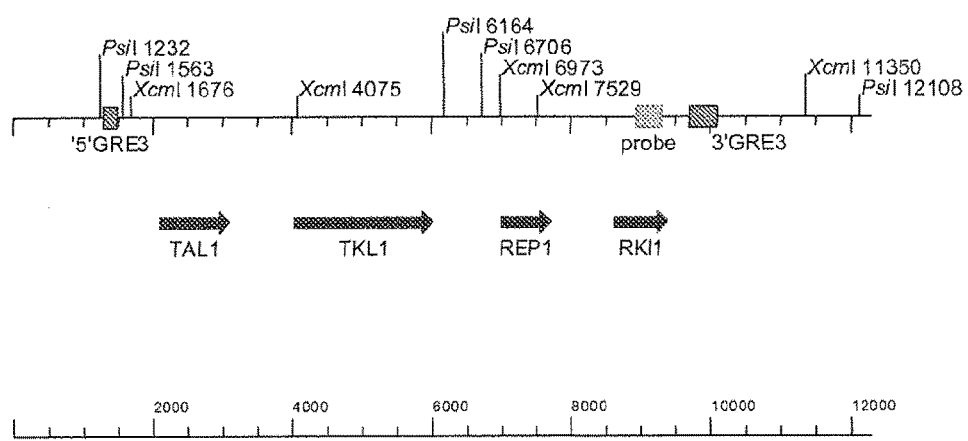

FIG. 5 sets out a physical map of the GRE3-locus, where the coding region of the GRE3-gene was replaced by the integration of the PPP-genes TAL1, TKL1, RKI1 and RPE1. Panel a shows the where the primers of SEQ ID 5 and 6 bind, panel b shows where the RKI1-probe binds.

Figure 6:
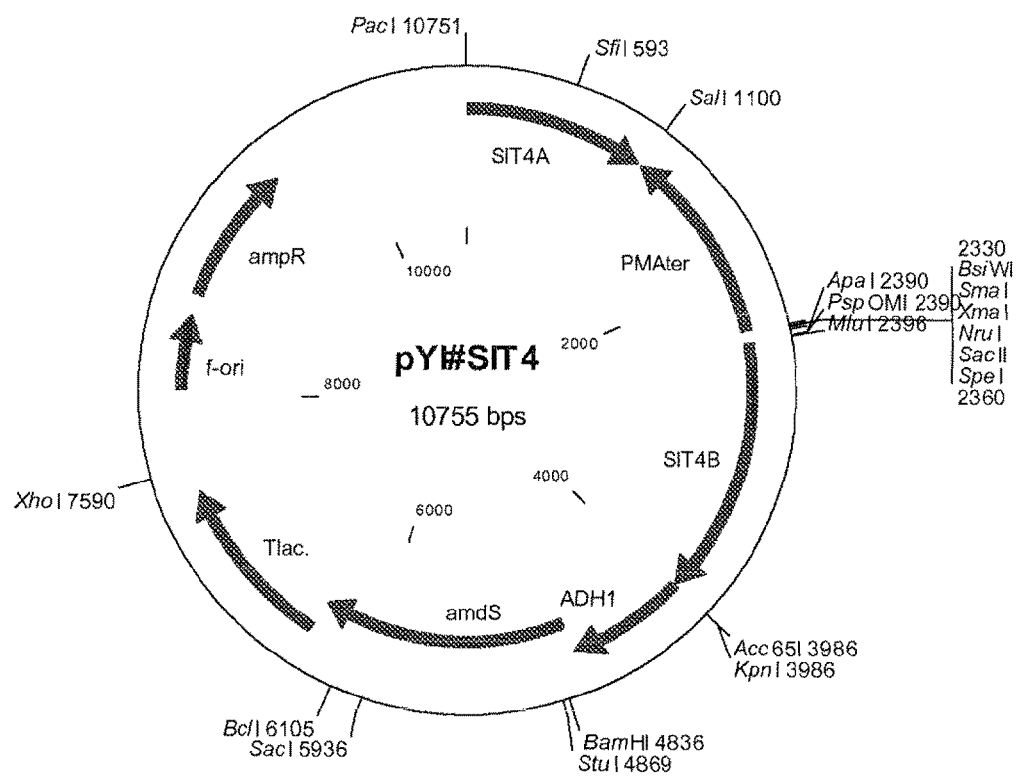

FIG. 6 sets out a physical map of plasmid pYI#SIT4

Figure 7:
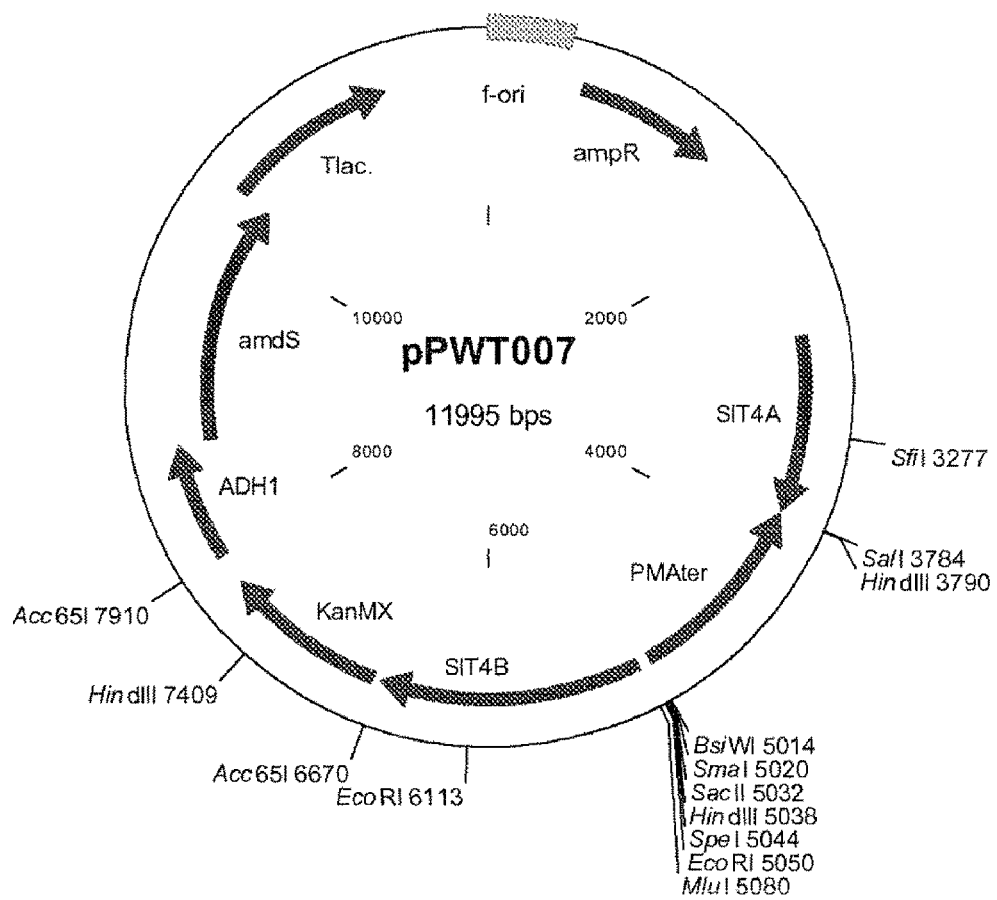

FIG. 7 sets out a physical map of plasmid pPWT007

Figure 8:
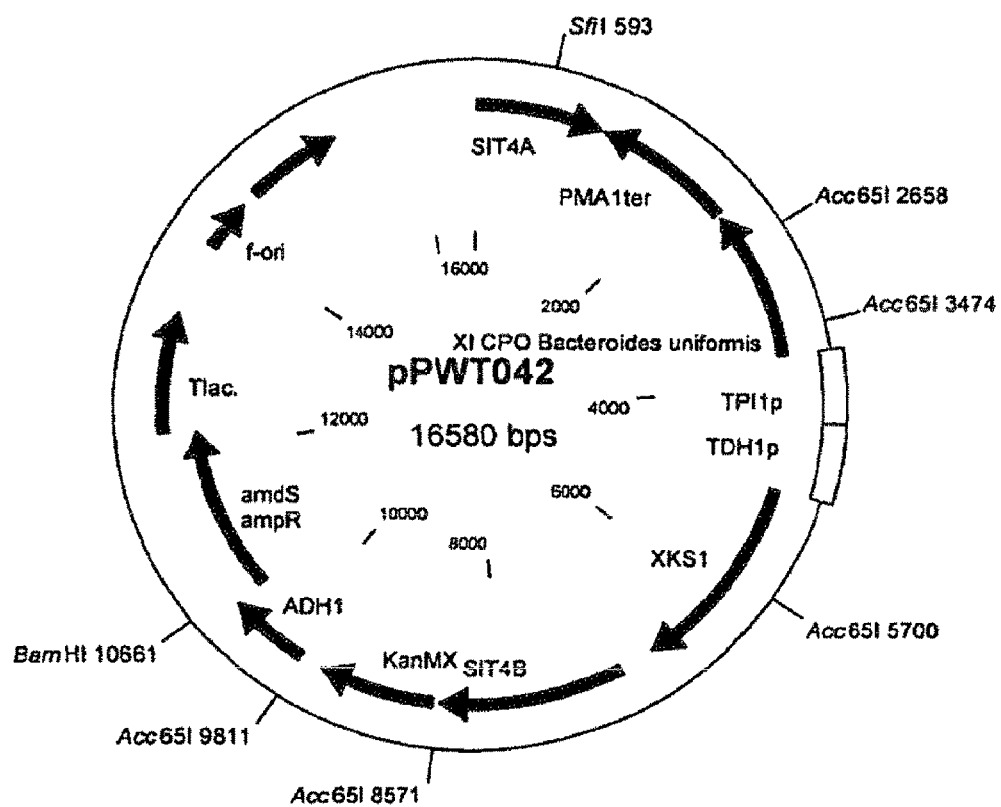

FIG. 8 sets out a physical map of plasmid pPWT042

Figure 9:
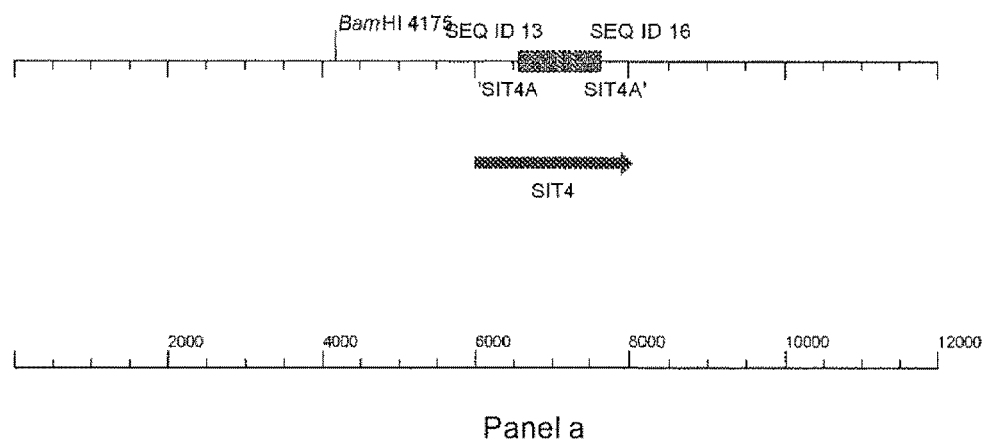
Figure 9:
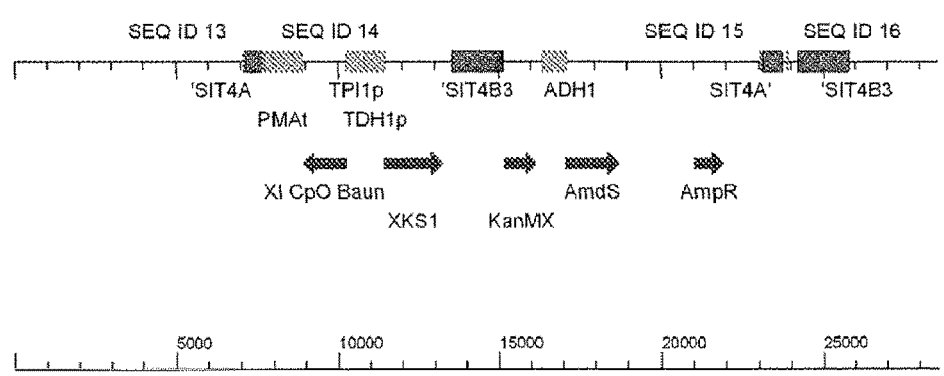

FIG. 9 sets out a physical map of the wild-type S/T4-locus (panel a) and a one copy integration of PWT080 in the S/T4-locus (panel b, showing where the primers bind)

Figure 10:
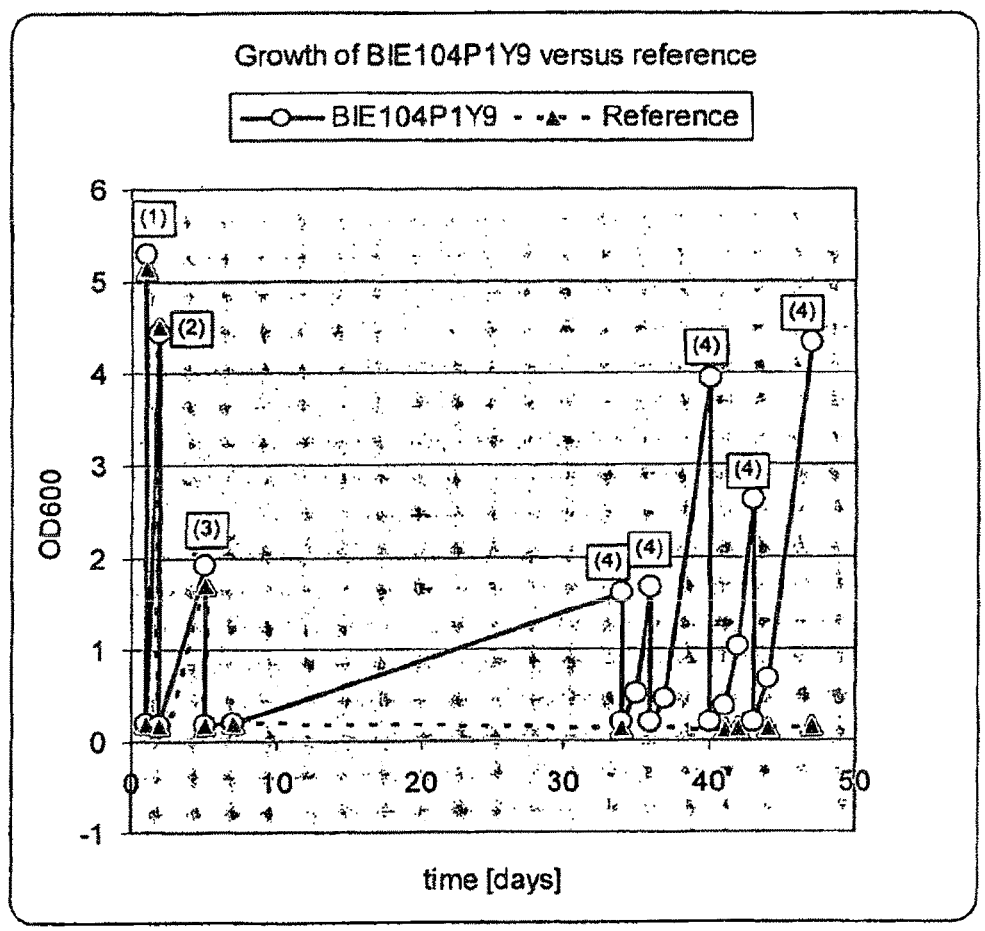

FIG. 10 sets out a growth curve of BIE104P1Y9 on 2% xylose as sole carbon source, after several precultivations, and of the reference strain without one copy of pPWT042 integrated in the genome. Events indicated in the graph by numbers (1): transfer to YNB 1% glucose+1% xylose; (2): transfer to YNB 0.1% glucose+2% xylose; (3) transfer to YNB 2% xylose; (4) transfer to YNB 2% xylose (only BIE104P1Y9).

Figure 11:
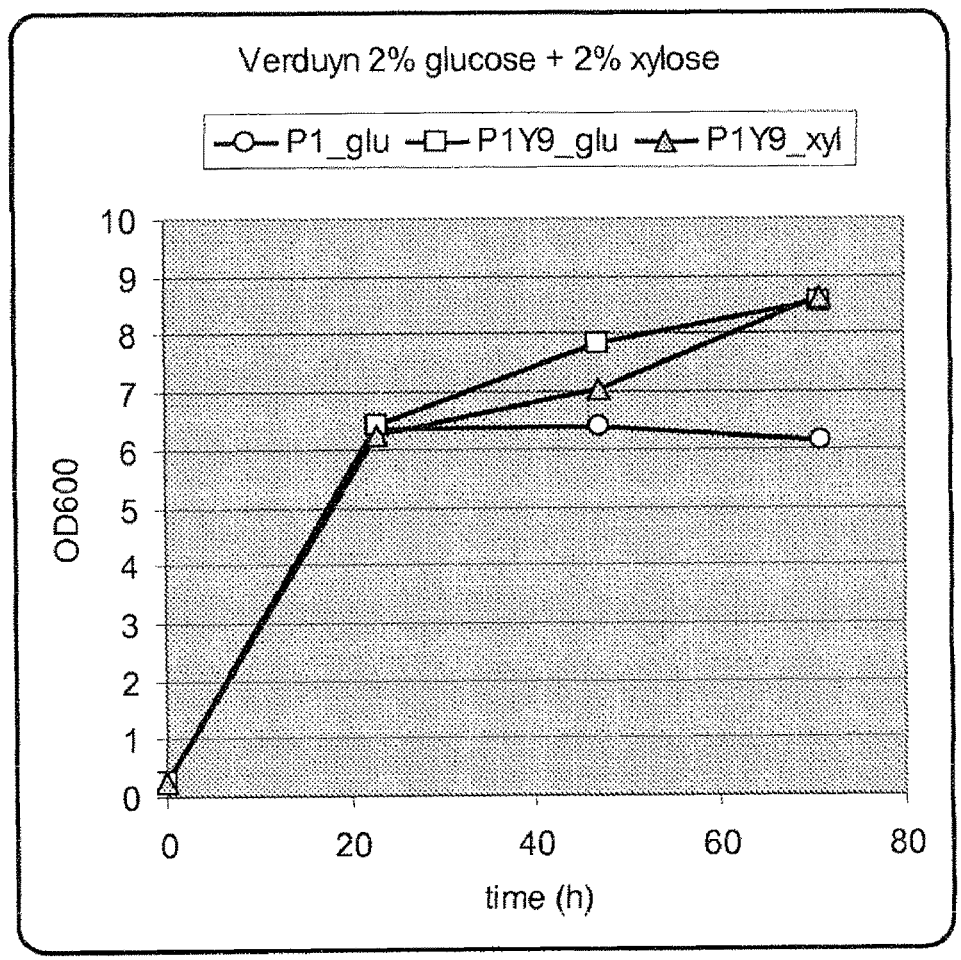

FIG. 11 sets out a growth curve of the reference strain BIE104P1 and a xylose metabolizing strain, BIE104P1Y9.

Figure 12:
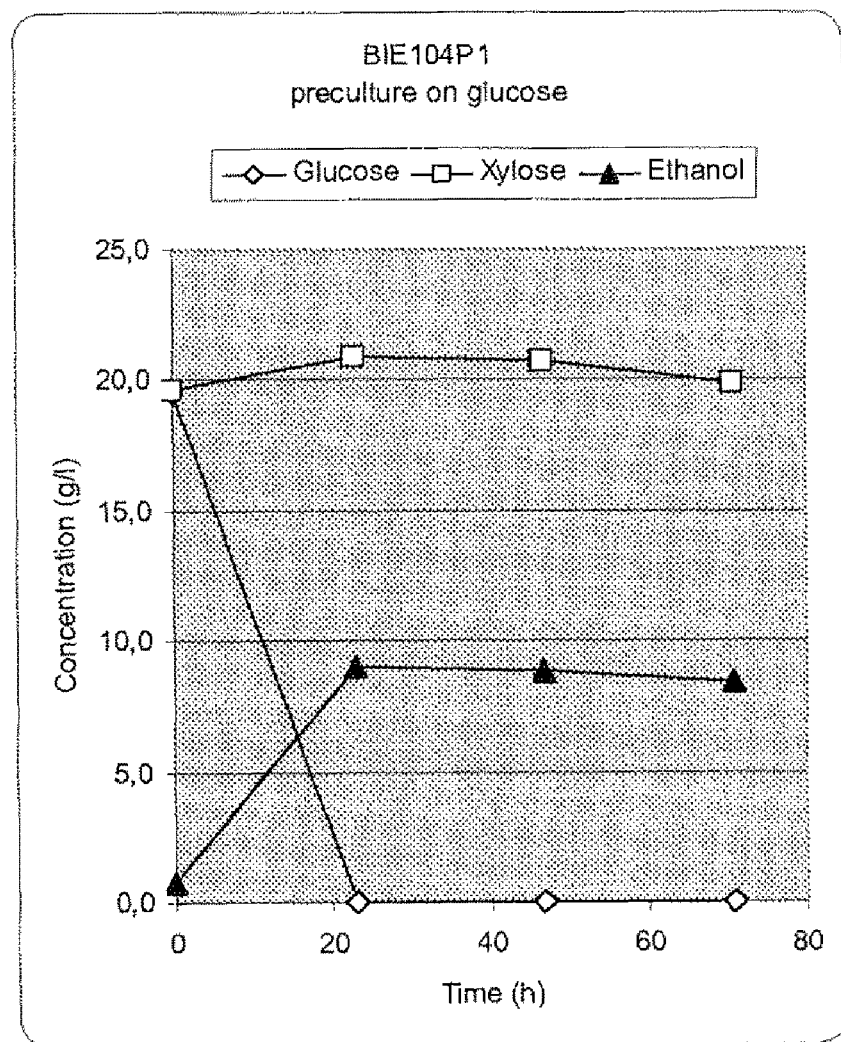
Figure 12:
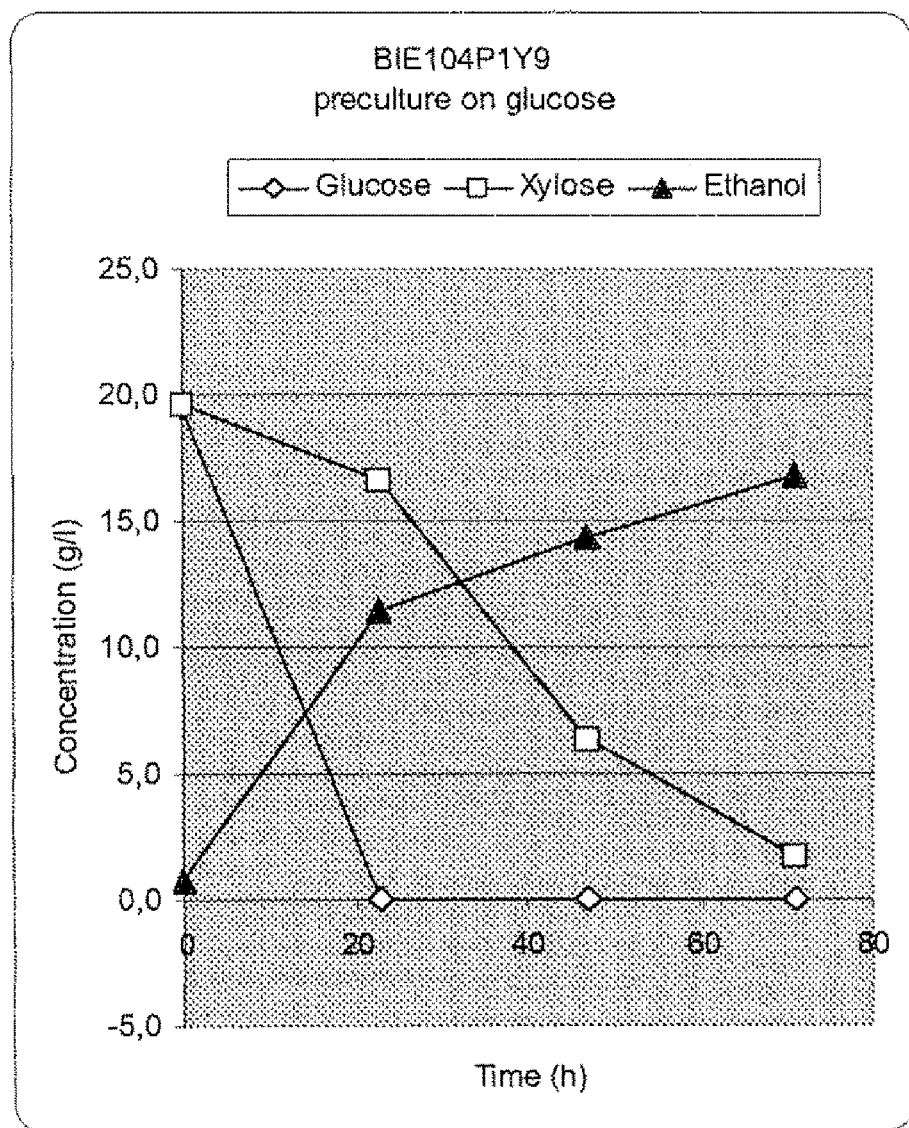
Figure 12:
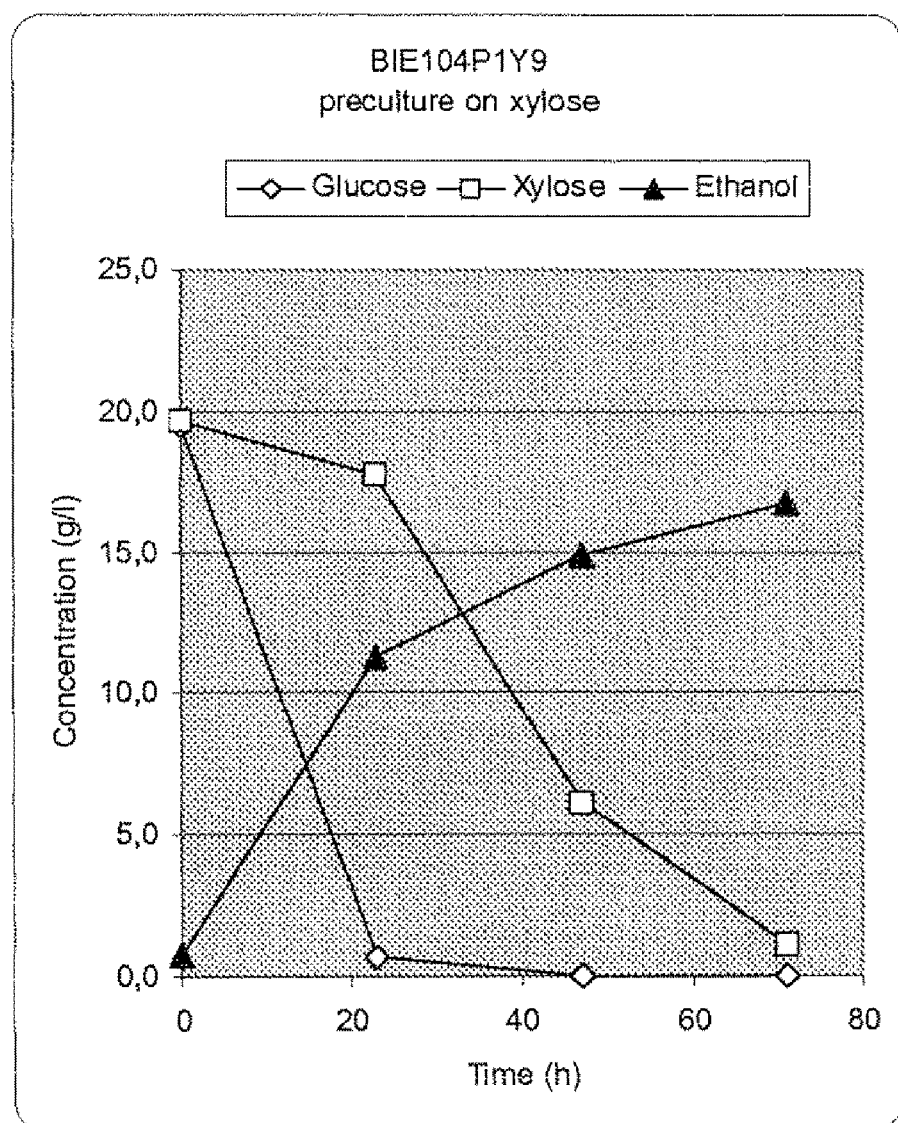

FIG. 12 sets out the xylose and glucose consumption and ethanol production in time of strains BIE104P1 precultured on glucose (panel a), BIE104P1Y9 precultured on glucose (panel b) and BIE104P1Y9 precultured on xylose (panel c).

Figure 13:
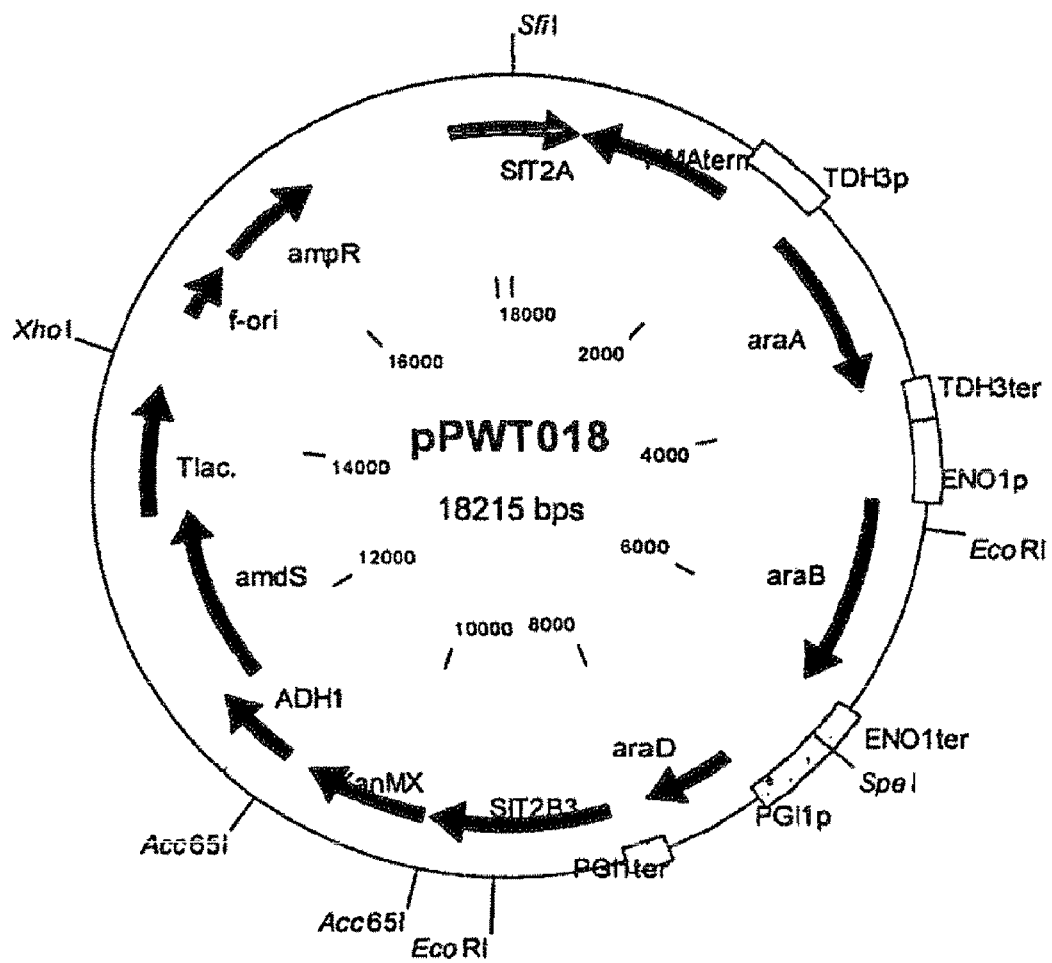

FIG. 13 sets out a physical map of plasmid pPWT018.

Figure 14:
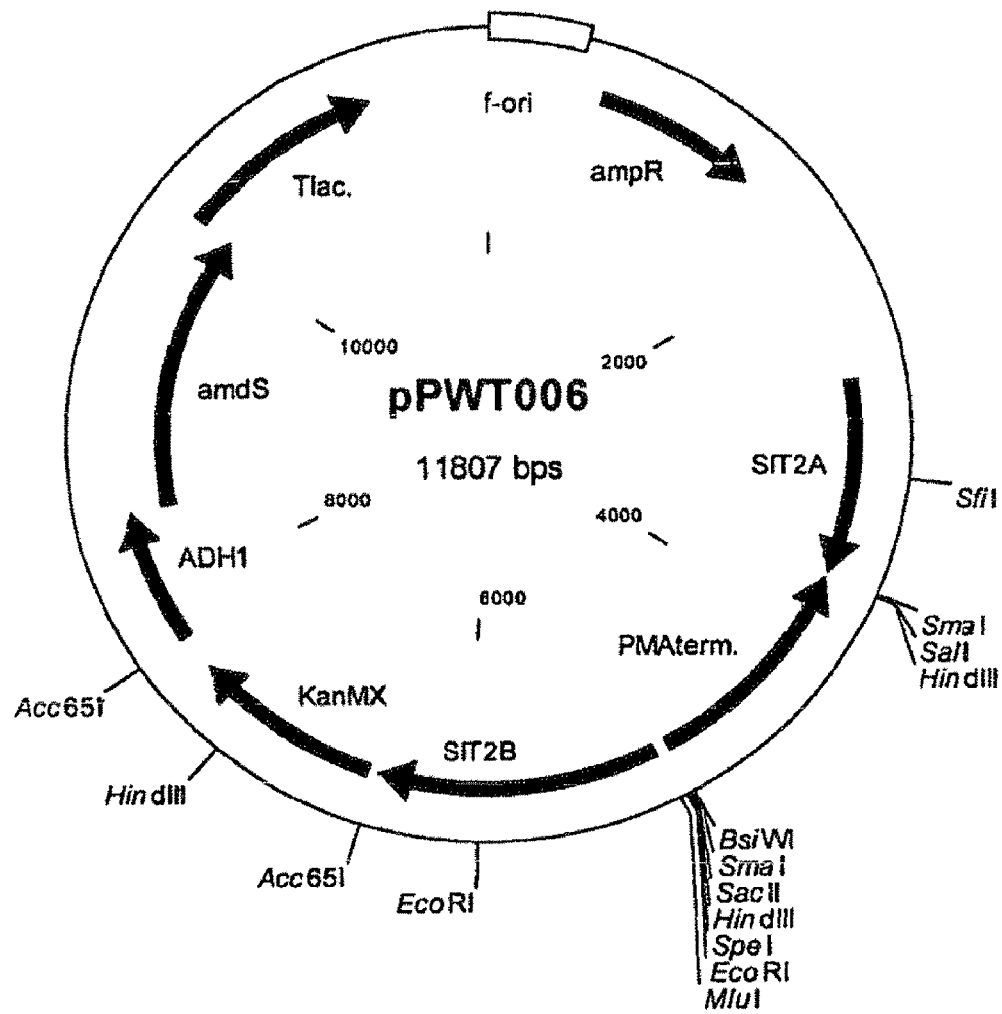

FIG. 14 sets out a physical map of plasmid pPWT006.

Figure 15:
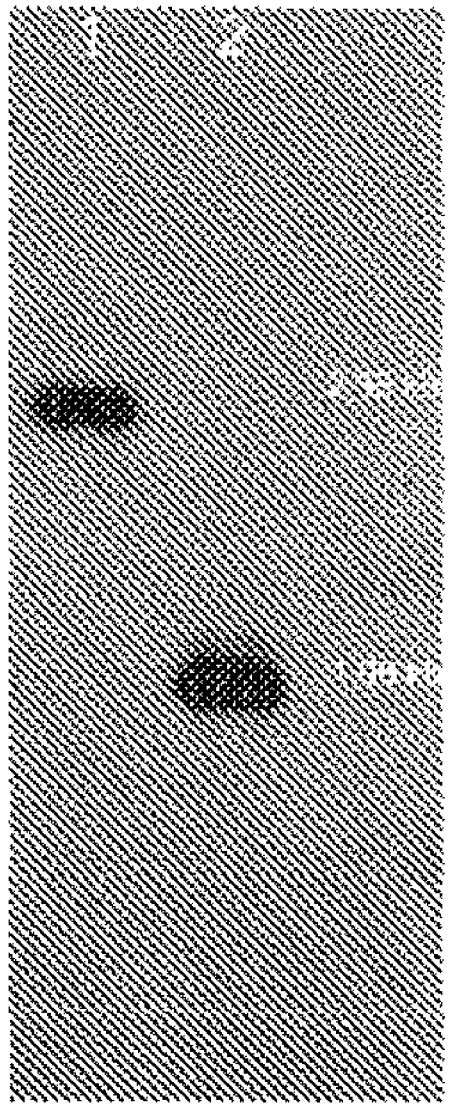

FIG. 15 sets out a Southern blot autoradiogram. Chromosomal DNA of wild-type strain CEN.PK113-7D (lane 1) and BIE104A2 (lane 2) was digested with Both EcoRI and HindIII. The blot was hybridized with a specific SIT2-probe.

Figure 16:
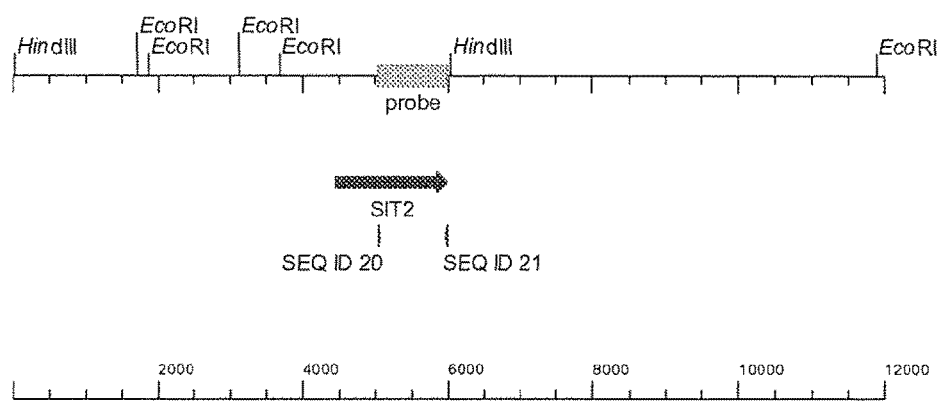
Figure 16:
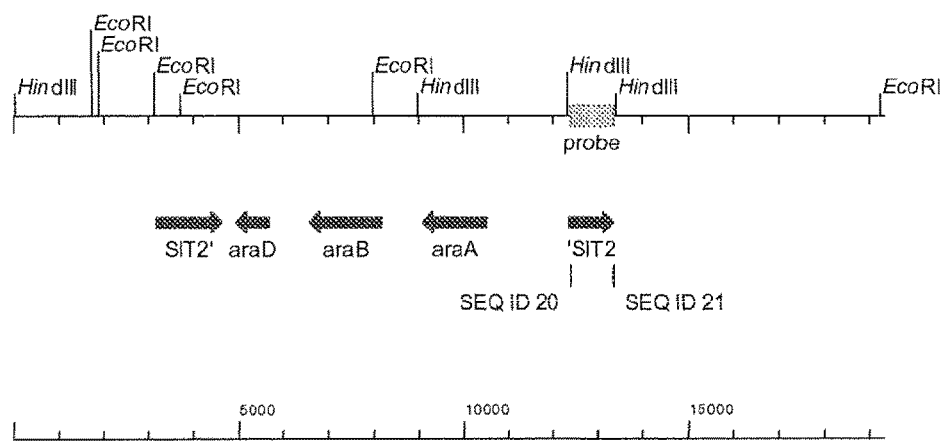

FIG. 16 sets out physical maps of the wild-type S/T2-locus (panel a) and after introduction of the ara-genes by integration of plasmid pPWT018, followed by intramolecular recombination leading to the loss of vector and selectable marker sequences (panel b). The hybridization of the probe is indicated.

Figure 17:
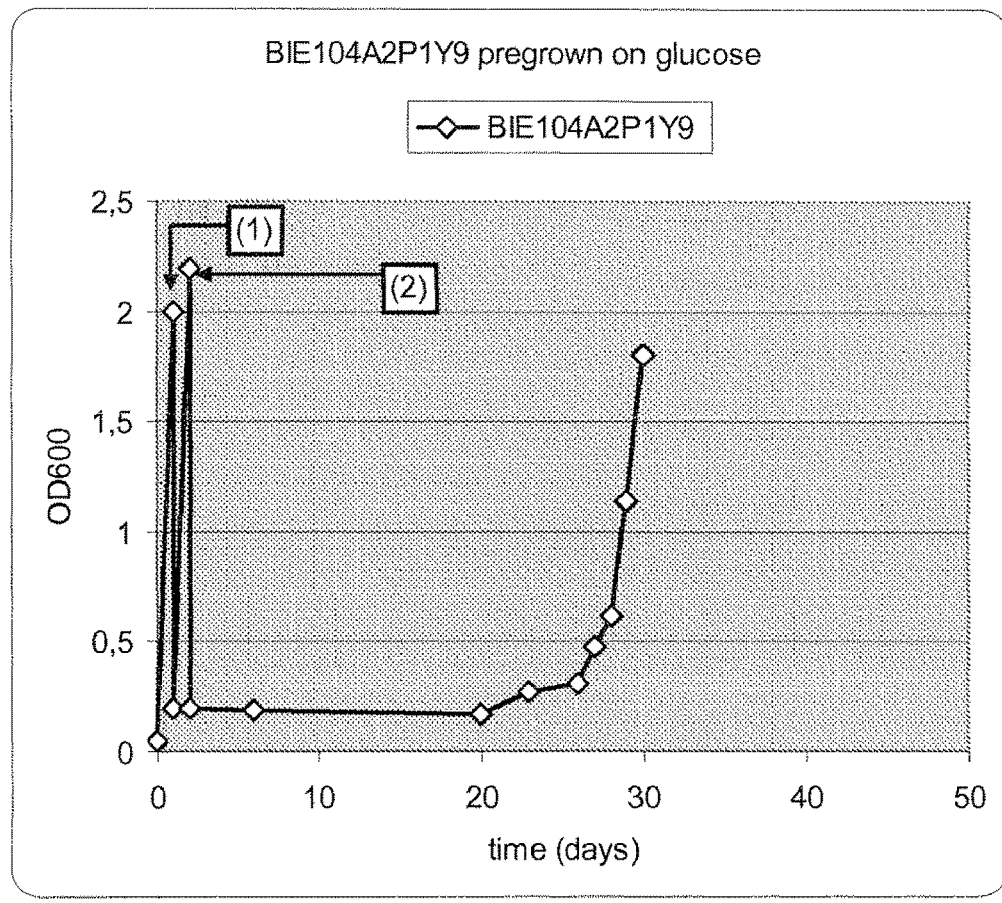
Figure 17:
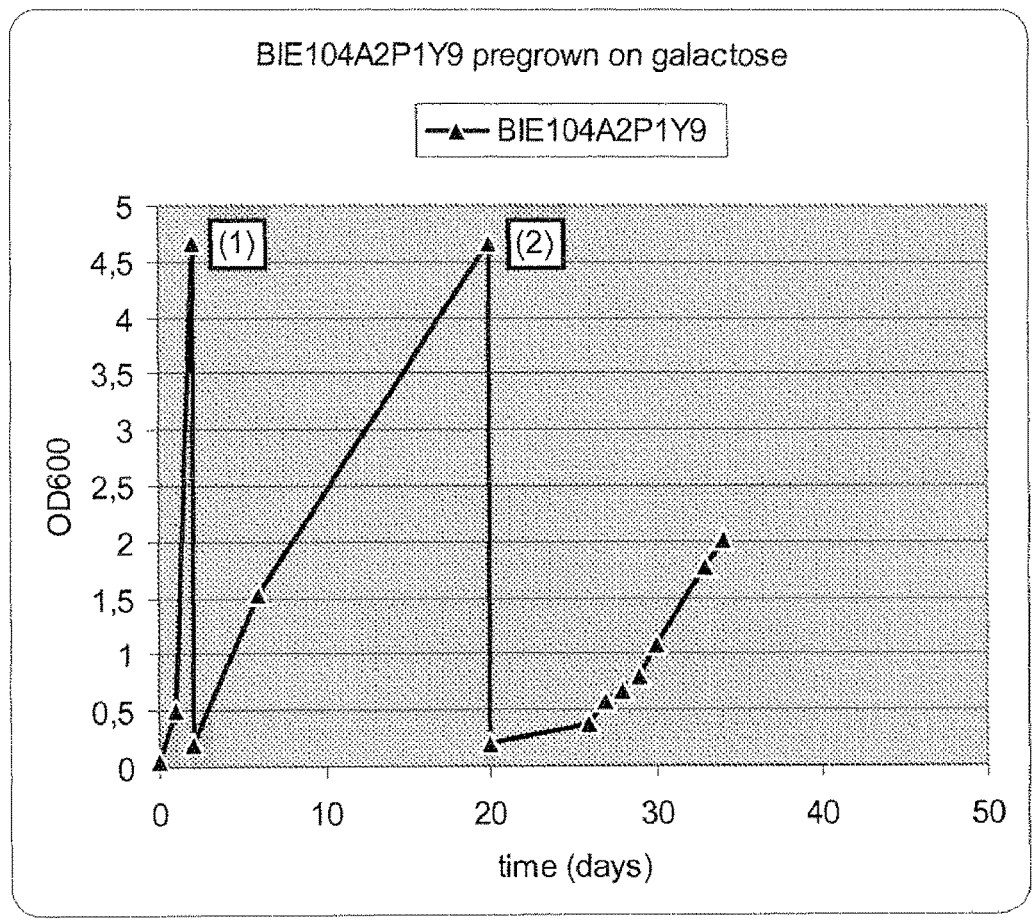

FIG. 17 sets out a graphic representation of growth curves of strain BIE104A2P1Y9 on different media. Panel a: strain BIE104A2P1Y9 grown on galactose, followed by events indicated in the graph by numbers (1) transfer to 1% arabinose+1% xylose and (2) transfer to 2% xylose+0.2% arabinose. Panel b: strain BIE104A2P1Y9 grown on glucose, followed by (1) transfer to 1% arabinose+1% xylose and (2) transfer to 2% xylose+0.2% arabinose.

BRIEF DESCRIPTION OF THE SEQUENCE LISTING

SEQ ID NO: 1 sets out the wild-type xylose isomerase sequence from *Bacteroides uniformis* ATCC 8492. Genbank accession no. AAYH02000036.
SEQ ID NO: 2 sets out a codon optimized sequence derived from SEQ ID NO: 1.
SEQ ID NO: 3 sets out the amino acid sequence of xylose isomerase from *Bacteroides uniformis* ATCC 8492.
SEQ ID NO: 4 sets out the sequence of plasmid pPWT080.
SEQ ID NO: 5 sets out the sequence of forward primer.
SEQ ID NO: 6 sets out the sequence of reverse primer.
SEQ ID NO: 7 sets out the sequence of the forward multifunctional primer for diagnostic PCR.
SEQ ID NO: 8 sets out the sequence of reverse multifunctional primer for diagnostic PCR.
SEQ ID NO: 9 sets out the sequence of forward primer RKI1-probe.
SEQ ID NO: 10 sets out the sequence of reverse primer RKI1-probe.
SEQ ID NO: 11 sets out the sequence of forward primer kanMX-cassette.
SEQ ID NO: 12 sets out the sequence of reverse primer kanMX-cassette.
SEQ ID NO: 13 sets out the sequence of forward primer.
SEQ ID NO: 14 sets out the sequence of reverse primer.
SEQ ID NO: 15 sets out the sequence of forward multifunctional primer for diagnostic PCR.
SEQ ID NO: 16 sets out the sequence of reverse multifunctional primer for diagnostic PCR.
SEQ ID NO: 17 sets out the sequence of sequence of plasmid pPWT018
SEQ ID NO: 18 sets out the sequence of forward primer integration pPWT018.
SEQ ID NO: 19 sets out the sequence of reverse primer integration pPWT018.
SEQ ID NO: 20 sets out the sequence of forward primer SIT2-probe.
SEQ ID NO: 21 sets out the sequence of reverse primer SIT2-probe.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The invention relates to a cell which comprises a nucleotide sequence encoding a xylose isomerase, wherein the amino acid sequence of the xylose isomerase has at least about 70% identity to the amino acid sequence set out in SEQ ID NO: 3 and wherein the nucleotide sequence is heterologous to the host.

The presence of the nucleotide sequence encoding a xylose isomerase confers on the cell the ability to isomerise xylose to xylulose.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, a cell of the invention is capable of isomerising xylose to xylulose. The ability of isomerising xylose to xylulose is conferred on the host cell by transformation of the host cell with a nucleic acid construct comprising a nucleotide sequence encoding a defined xylose isomerase. A cell of the invention isomerises xylose into xylulose by the direct isomerisation of xylose to xylulose. This is understood to mean that xylose is isomerised into xylulose in a single reaction catalysed by a xylose isomerase, as opposed to two step conversion of xylose into xylulose via a xylitol intermediate as catalysed by xylose reductase and xylitol dehydrogenase, respectively.

A unit (U) of xylose isomerase activity may herein be defined as the amount of enzyme producing 1 nmol of xylulose per minute, under conditions as described by Kuyper et al. (2003, FEMS Yeast Res. 4: 69-78).

The cell of the invention is defined with reference to a xylose isomerase having the amino acid sequence of SEQ ID NO: 3 or a sequence having at least about 70% sequence identity thereto. Likewise, a cell of the invention may be defined with reference to a xylose isomerase be a nucleotide sequence which encoding such an amino acid sequence.

SEQ ID NO: 3 sets out the amino acid sequence of xylose isomerase from *Bacteroides uniformis* ATCC 8492. A cell of the invention comprises a nucleotide sequence encoding a xylose isomerase having the amino acid of SEQ ID NO: 3 or one which has at least about 70% sequence identity thereto.

Preferably, a cell according to the present invention is a cell comprising a nucleotide sequence encoding a xylose isomerase having a sequence which has at least about 75%, preferably at least about 80%, at least about 85%, at least about 90%, at least about 92%, at least about 93%, at least about 94%, at least about 95%, at least about 96%, at least about 97%, at least about 98% or at least about 99% or at least 75%, at least 80%, at least 85%, at least 90%, at least 92%, at least 93%, at least 94%, at least 95%, at least 96%, at least 97%, at least 98% or at least 99% sequence identity with the amino acid sequence of SEQ ID NO:3. However, a cell according according to the present invention may comprise a nucleotide sequence encoding a xylose isomerase having a sequence which has at least about 50%, at least about 55%, at least about 60% or at least about 70% sequence identity with the amino acid sequence set out in SEQ ID NO: 3.

Sequence identity (or sequence similarity) is herein defined as a relationship between two or more amino acid (polypeptide or protein) sequences or two or more nucleic acid (polynucleotide) sequences, as determined by comparing the sequences. Usually, sequence identities or similarities are compared, typically over the whole length of the sequences compared. However, sequences may be compared over shorter comparison windows. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix. Preferred parameters for nucleic acid sequences comparison using BLASTP are gap open 11.0, gap extend 1, DNA full matrix (DNA identity matrix).

Optionally, in determining the degree of amino acid similarity, the skilled person may also take into account so-called "conservative" amino acid substitutions, as will be clear to the skilled person.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine.

Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; He to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A nucleotide sequence encoding an enzyme which catalyses the conversion of xylose to xylulose according to the invention may also be defined by its capability to hybridise with the nucleotide sequences encoding the enzyme having the sequence set out in SEQ ID NO: 3 or a sequence having at least about 70% sequence identity therewith, under moderate, or preferably under stringent hybridisation conditions.

Formally, such nucleotide sequences hybridize with the reverse complement of the nucleotide sequences which encode the enzyme having the sequence set out in SEQ ID NO: 3 or a sequence having at least about 70% sequence identity therewith, for examples sequences which hybridize with the reverse complement of SEQ ID NOs: 1 or 2.

Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC (sodium chloride, sodium citrate) or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

To increase the likelihood that the introduced enzyme is expressed in active form in a cell of the invention, the corresponding encoding nucleotide sequence may be adapted to optimise its codon usage to that of the chosen yeast cell. Several methods for codon optimisation are known in the art. A preferred method to optimise codon usage of the nucleotide sequences to that of the yeast is a codon pair optimization technology as disclosed in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

As a simple measure for gene expression and translation efficiency, herein, the Codon Adaptation Index (CAI), as described in Xuhua Xia, Evolutionary Bioinformatics 2007: 3 53-58, is used. The index uses a reference set of highly expressed genes from a species to assess the relative merits of each codon, and a score for a gene is calculated from the frequency of use of all codons in that gene. The index assesses the extent to which selection has been effective in moulding the pattern of codon usage. In that respect it is useful for predicting the level of expression of a gene, for assessing the adaptation of viral genes to their hosts, and for making comparisons of codon usage in different organisms. The index may also give an approximate indication of the likely success of heterologous gene expression. In the codon pair optimized genes according to the invention, the CAI is 0.6 or more, 0.7 or more, 0.8 or more, 0.85 or more, 0.87 or more 0.90 or more, 0.95 or more, or about 1.0.

In a cell of the invention, the xylose isomerase is typically heterologous to the cell. That is to say, the xylose isomerase has a sequence which does not naturally occur in the cell in question as part of the organism, cell, genome DNA or RNA sequence in which it is present. That is to say, the xylose isomerase is exogenous to the cell or does not occur naturally in the cell. Accordingly, a nucleotide sequence encoding a xylose isomerase is typically expressed or is capable of being expressed in active form in the transformed host cell.

A cell of the invention is thus a cell that comprises, i.e. has been transformed with, a nucleic acid construct comprising the nucleotide sequence encoding the xylose isomerase as defined above. The nucleic acid construct comprising the xylose isomerase coding sequence preferably is capable of expression of the xylose isomerase in the host cell.

Methods for expressing a heterologous xylose isomerase sequence in a cell are well known to those skilled in the art.

Accordingly, a cell of the invention is a recombinant cell. That is to say, a cell of the invention comprises, or is transformed with or is genetically modified with a nucleotide sequence that does not naturally occur in the cell in question.

Techniques for the recombinant expression of xylose isomerase in a cell, as well as for the additional genetic modifications of a cell of the invention are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Most episomal or 2µ plasmids are relatively unstable, being lost in approximately $10^{-2}$ or more cells after each generation. Even under conditions of selective growth, only 60% to 95% of the cells retain the episomal plasmid. The copy number of most episomal plasmids ranges from 10-40 per cell of cir+ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated. Stable integration is herein defined as integration into the genome, wherein looping out of the integrated construct is no longer possible. Preferably selection markers are absent.

Typically, the nucleic acid construct may be a plasmid, for instance a low copy plasmid or a high copy plasmid. The cell according to the present invention may comprise a single or multiple copies of the nucleotide sequence encoding a xylose isomerase, for instance by multiple copies of a nucleotide construct or by use of construct which has multiple copies of the xylose isomerase sequence.

The nucleic acid construct may be maintained episomally and thus comprise a sequence for autonomous replication, such as an autosomal replication sequence sequence. A suitable episomal nucleic acid construct may e.g. be based on the yeast 2µ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265,186).

Typically, the xylose isomerase encoding sequence will be operably linked to one or more nucleic acid sequences, capable of providing for or aiding the transcription and/or translation of the xylose isomerase sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3.

In a cell of the invention, the 3'-end of the nucleotide acid sequence encoding xylose isomerase preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the xylose isomerase comprises a terminator. Preferably, such terminators are combined with mutations that prevent nonsense mediated mRNA decay in the host cell of the invention (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Although the of antibiotic resistance markers may be most convenient for the transformation of polyploid host cells, preferably however, non-antibiotic resistance markers are used, such as auxotrophic markers (URA3, TRPI, LEU2) or the *S. pombe* TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-O 635 574 and are based on the use of bidirectional markers such as the *A. nidulans* amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

Preferably, the xylose isomerase is expressed in the cytosol. Cytosolic expression may be achieved by deletion or modification of a mitochondrial or peroxisomal targeting signal.

A cell of the invention may be any suitable cell, such as a prokaryotic cell, such as a bacterium, or a eukaryotic cell. Typically, the cell will be a eukaryotic cell, for example a yeast or a filamentous fungus.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a cell of the invention may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic fermentation, more preferably one capable of anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides.

The filamentous fungi of the suitable for use as a cell of the present invention are morphologically, physiologically, and genetically distinct from yeasts. Filamentous fungal cells may be advantageously used since most fungi do not require sterile conditions for propagation and are insensitive to bacteriophage infections. Vegetative growth by filamentous fungi is by hyphal elongation and carbon catabolism of most filamentous fungi is obligately aerobic. Preferred filamentous fungi as a host cell of the invention may belong to the genus *Aspergillus, Trichoderma, Humicola, Acremoniurra, Fusarium* or *Penicillium*. More preferably, the filamentous fungal cell may be a *Aspergillus niger, Aspergillus oryzae*, a *Penicillium chrysogenum*, or *Rhizopus oryzae* cell.

Over the years suggestions have been made for the introduction of various organisms for the production of bio-ethanol from crop sugars. In practice, however, all major bioethanol production processes have continued to use the yeasts of the genus *Saccharomyces* as ethanol producer. This is due to the many attractive features of *Saccharomyces* species for industrial processes, i.e., a high acid-, ethanol- and osmotolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus* or *K fragilis*.

A cell of the invention may be able to convert plant biomass, celluloses, hemicelluloses, pectins, rhamnose, galactose, fucose, maltose, maltodextrines, ribose, ribulose, or starch, starch derivatives, sucrose, lactose and glycerol, for example into fermentable sugars. Accordingly, a cell of the invention may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

A cell of the invention is preferably is a host capable of active or passive xylose transport into the cell.

Preferably, a cell of the invention:
is capable of active glycolysis; and/or
shows flux through the pentose phosphate pathway; and/or
displays xylulose kinase activity so that the xylulose isomerised from xylose may be metabolised to pyruvate.

The cell further preferably comprises those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

A preferred cell of the invention is a cell that is naturally capable of alcoholic fermentation, preferably, anaerobic alcoholic fermentation. A cell of the invention preferably has a high tolerance to ethanol, a high tolerance to low pH (i.e. capable of growth at a pH lower than about 5, about 4, about 3, or about 2.5) and towards organic acids like lactic acid, acetic acid or formic acid and/or sugar degradation products such as furfural and hydroxy-methylfurfural and/or a high tolerance to elevated temperatures.

Any of the above characteristics or activities of a cell of the invention may be naturally present in the cell or may be introduced or modified by genetic modification.

The nucleotide sequence encoding a xylose isomerase is typically expressed or is capable of being expressed in active form in the transformed host cell. Thus, expression of the nucleotide sequence in the host cell produces an active xylose isomerase, typically with a specific activity of at least about 10 U xylose isomerase activity per mg protein at about 30° C., preferably at least about 20, at least about 25, at least about 30, at least about 50, at least about 100, at least about 200, at least about 300, at least about 500, at least about 750 or at least about 1000 U per mg at about 30° C. The specific activity of the xylose isomerase expressed in the transformed host cell is herein defined as the amount of xylose isomerase activity units per mg protein of cell free lysate of the host cell, e.g. a yeast cell free lysate. Determination of the xylose isomerase activity, amount of protein and preparation of the cell free lysate are as described herein. Preferably, expression of the nucleotide sequence encoding the xylose isomerase in the host cell produces a xylose isomerase with a $K_m$ for xylose that is less than 50, 40, 30 or 25 mM, more preferably, the $K_m$ for xylose is about 20 mM or less.

A cell of the invention may comprise one or more genetic modifications that increases the flux of the pentose phosphate pathway. In particular, the genetic modification(s) may lead to an increased flux through the non-oxidative part pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s=\mu/Y_{xs}$). Therefore the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RPI1.

The enzyme "transketolase" (EC 2.2.1.1) is herein defined as an enzyme that catalyses the reaction: D-ribose 5-phosphate+D-xylulose 5-phosphate<->sedoheptulose 7-phosphate+D-glyceraldehyde 3-phosphate and vice versa. The enzyme is also known as glycolaldehydetransferase or sedoheptulose-7-phosphate:D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate<->D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate:D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transketolase from is herein designated TAL1.

Various means are known to those skilled in the art for expression and overexpression of enzymes in a cell of the invention. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence, preferably under conditions where xylose or xylose and glucose are available as carbon sources, more preferably as major carbon sources (i.e. more than 50% of the available carbon source consists of xylose or xylose and glucose), most preferably as sole carbon sources. Suitable promoters in this context include both constitutive and inducible natural promoters as well as engineered promoters. A preferred promoter for use in the present invention will in addition be insensitive to catabolite (glucose) repression and/or will preferably not require xylose for induction. Promotors having these characteristics are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADHI, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics.

The coding sequence used for overexpression of the enzymes mentioned above may preferably be homologous to the host cell of the invention. However, coding sequences that are heterologous to the host cell of the invention may be used.

Overexpression of an enzyme, when referring to the production of the enzyme in a genetically modified host cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Overexpression of an enzyme is thus preferably determined by measuring the level of the enzyme's specific activity in the host cell using appropriate enzyme assays as described herein. Alternatively, overexpression of the enzyme may be determined indirectly by quantifying the specific steady state level of enzyme protein, e.g. using antibodies specific for the enzyme, or by quantifying the specific steady level of the mRNA coding for the enzyme. The latter may particularly be suitable for enzymes of the pentose phosphate pathway for which enzymatic assays are not easily feasible as substrates for the enzymes are not commercially available. Preferably in a host cell of the invention, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention may comprise one or more genetic modifications that increase the specific xylulose kinase activity. Preferably the genetic modification or modifications causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell of the invention is a nucleotide sequence encoding a polypeptide with xylulose kinase activity.

The enzyme "xylulose kinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinase or ATP: D-xylulose 5-phosphotransferase. A xylulose kinase of the invention may be further defined by its amino acid sequence. Likewise a xylulose kinase may be defined by a nucleotide sequence encoding the enzyme as well as by a nucleotide sequence hybridising to a reference nucleotide sequence encoding a xylulose kinase.

In a cell of the invention, a genetic modification or modifications that increase(s) the specific xylulose kinase activity may be combined with any of the modifications increasing the flux of the pentose phosphate pathway as described above. This is not, however, essential.

Thus, a host cell of the invention may comprise only a genetic modification or modifications that increase the specific xylulose kinase activity. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor of about 1.1, about 1.2, about 1.5, about 2, about 5, about 10 or about 20 as compared to a strain which is genetically identical except for the genetic modification(s) causing the overexpression. It is to be understood that these levels of overexpression may apply to the steady state level of the enzyme's activity, the steady state level of the enzyme's protein as well as to the steady state level of the transcript coding for the enzyme.

A cell of the invention may comprise one or more genetic modifications that reduce unspecific aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an unspecific aldose reductase in the host cell. Host cells may comprise multiple copies of genes encoding unspecific aldose reductases as a result of di-, poly- or aneu-ploidy, and/or the host cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or downstream of the coding sequence, the (partial) deletion or inactivation of which results in a reduction of expression of unspecific aldose reductase activity in the host cell.

A nucleotide sequence encoding an aldose reductase whose activity is to be reduced in the host cell of the invention is a nucleotide sequence encoding a polypeptide with aldose reductase activity.

In the host cells of the invention, genetic modification that reduces unspecific aldose reductase activity in the host cell may be combined with any of the modifications increasing the flux of the pentose phosphate pathway and/or with any of the modifications increasing the specific xylulose kinase activity in the host cells as described above. This is not, however, essential.

Thus, a host cell of the invention comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

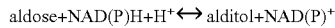

aldose+NAD(P)H+H$^+$ ⟷ alditol+NAD(P)$^+$

The enzyme has a wide specificity and is also known as aldose reductase; polyol dehydrogenase (NADP$^+$); alditol: NADP oxidoreductase; alditol:NADP$^+$ 1-oxidoreductase; NADPH-aldopentose reductase; or NADPH-aldose reductase.

A particular example of such an unspecific aldose reductase that is endogenous to S. cerevisiae and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

A cell of the invention may be adapted to xylose utilisation by selection of mutants, either spontaneous or induced (e.g. by radiation or chemicals), for growth on xylose, preferably on xylose as sole carbon source, and more preferably under anaerobic conditions. Selection of mutants may be performed by techniques including serial passaging of cultures as e.g. described by Kuyper et al. (2004, FEMS Yeast Res. 4: 655-664) or by cultivation under selective pressure in a chemostat culture. In a preferred host cell of the invention at least one of the genetic modifications described above, including modifications obtained by selection of mutants, confer to the host cell the ability to grow on xylose as carbon source, preferably as sole carbon source, and preferably under anaerobic conditions. Preferably the modified host cell produce essentially no xylitol, e.g. the xylitol produced is below the detection limit or e.g. less than about 5, about 2, about 1, about 0.5, or about 0.3% of the carbon consumed on a molar basis.

A cell of the invention may have the ability to grow on xylose as sole carbon source at a rate of at least about 0.05, about 0.1, about 0.2, about 0.25 or about 0.3 h$^{-1}$ under aerobic conditions, or, if applicable, at a rate of at least about 0.03, about 0.05, about 0.07, about 0.08, about 0.09, about 0.1, about 0.12, about 0.15 or about 0.2 h$^{-1}$ under anaerobic conditions. Preferably the modified host cell has the ability to grow on a mixture of glucose and xylose (in a 1:1 weight ratio) as sole carbon source at a rate of at least about 0.05, about 0.1, about 0.2, about 0.25 or about 0.3 h$^{-1}$ under aerobic conditions, or, if applicable, at a rate of at least about 0.03, about 0.05, about 0.1, about 0.12, about 0.15, or about 0.2 h$^{-1}$ under anaerobic conditions.

A cell of the invention may have a specific xylose consumption rate of at least about 200, about 250, about 300, about 346, about 350, about 400, about 500, about 600, about 750, or about 1000 mg xylose/g cells/h. A cell of the invention may have a yield of fermentation product (such as ethanol) on xylose that is at least about 40, about 50, about 55, about 60, about 70, about 80, about 85, about 90, about 95 about 98 or about 99% of the host cell's yield of fermentation product (such as ethanol) on glucose. More preferably, the yield of a fermentation product (such as ethanol) of a cell of the invention on xylose may be equal to the cell's yield of fermentation product (such as ethanol) on glucose. Likewise, the cell's biomass yield on xylose may be at least about 40, about 50, about 55, about 60, about 70, about 80, about 85, about 90, about 95, about 98 or about 99% of the host cell's biomass yield on glucose. More preferably, the cell's biomass yield on xylose, may be equal to the host cell's biomass yield on glucose. It is understood that in the comparison of yields on glucose and xylose both yields are compared under aerobic conditions or both under anaerobic conditions.

A cell of the invention may be capable of using arabinose. A cell of the invention may, therefore, be capable of converting L-arabinose into L-ribulose and/or xylulose 5-phosphate and/or into a desired fermentation product, for example one of those mentioned herein.

Organisms, for example S. cerevisiae strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a cell of the invention is order that it is capable of using arabinose. Such an approach is described in WO2003/095627.

A cell of the invention may be a cell suitable for the production of ethanol. A cell of the invention may, however, be suitable for the production of fermentation products other than ethanol. Such non-ethanolic fermentation products include in principle any bulk or fine chemical that is producible by a eukaryotic microorganism such as a yeast or a filamentous fungus.

Such fermentation products may be, for example, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin. A preferred modified host cell of the invention for production of non-ethanolic fermentation products is a host cell that contains a genetic modification that results in decreased alcohol dehydrogenase activity.

In a further aspect the invention relates to fermentation processes in which the modified host cells of the invention are used for the fermentation of a carbon source comprising a source of xylose, such as xylose. In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g. lignocellulose, xylans, cellulose, starch and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose.

In a preferred process the modified host cell ferments both the xylose and glucose, preferably simultaneously in which case preferably a modified host cell is used which is insensitive to glucose repression to prevent diauxic growth. In addition to a source of xylose (and glucose) as carbon source, the fermentation medium will further comprise the appropriate ingredient required for growth of the modified host cell. Compositions of fermentation media for growth of microorganisms such as yeasts are well known in the art. The fermentation process is a process for the production of a fermentation product such as e.g. ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic, such as Penicillin G or Penicillin V and fermentative derivatives thereof, and a cephalosporin.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a β-lactam antibiotic and a cephalosporin.

The fermentation process is preferably run at a temperature that is optimal for the modified host cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

A preferred process is a process for the production of a ethanol, whereby the process comprises the steps of: (a) fermenting a medium containing a source of xylose with a modified host cell as defined above, whereby the host cell ferments xylose to ethanol; and optionally, (b) recovery of the ethanol. The fermentation medium may also comprise a source of glucose that is also fermented to ethanol. In the process the volumetric ethanol productivity is preferably at least about 0.5, about 1.0, about 1.5, about 2.0, about 2.5, about 3.0, about 5.0 or about 10.0 g ethanol per liter per hour. The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product, such as a product selected from the group consisting of butanol lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. The process preferably comprises fermenting a medium containing a source of xylose with a modified host cell as defined herein above, whereby the host cell ferments xylose to the fermentation product.

The invention also provides a process for producing a fermentation product, such as a product selected from the group consisting of ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. The process preferably comprises fermenting a medium containing at least a source of xylose and a source of L-arabinose with a cell as defined above which is able to use both of xylose and L-arabinose such that the cell ferments xylose and L-arabinose to the fermentation product.

The invention also provides a process for producing a fermentation product, such as a product selected from the group consisting of ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. The process preferably comprises fermenting a medium containing at least a source of xylose and a source of L-arabinose with a cell as defined above and a cell able to use L-arabinose, whereby each cell ferments xylose and/or arabinose to the fermentation product.

A process of the invention may also comprise recovery of the fermentation product. The medium with which the process is carried out may also contain a source of glucose.

The process according to the present invention may be run under aerobic and anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h.

The following Examples illustrate the invention:

EXAMPLES

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Xylose Isomerise Activity (as Determined in Examples 1 and 2)

Xylose isomerase activity may be assayed at 37° C. in a reaction mixture containing 50 mM phosphate buffer (pH 7.0), 10 mM xylose, 10 mM $MgCl_2$ and a suitable amount of cell-free extract. The amount of xylulose formed may be determined by the cysteine-carbazole method (Goldstein and McCusker, Yeast 15, 1541-1553, 1999). Alternatively, xylose isomerase activity is assayed at 30° C. using the enzyme assay of Kersters-Hildersson et al. (Kinetic characterization of D-xylose isomerases by enzymatic assays using D-sorbitol dehydrogenase. Enz. Microb. Technol. 9 (1987) 145-148). The in vitro activity of xylose isomerase in the cell-free extracts of transformed S. cerevisiae strains is dependent on bivalent cations ($Mg_2^+$ or $CO_2^+$).

Transformation of S. cerevisiae

Transformation of S. cerevisiae was done as described by Gietz and Woods (2002; Transformation of the yeast by the LiAc/SS carrier DNA/PEG method. Methods in Enzymology 350: 87-96).

Colony PCR

A single colony isolate was picked with a plastic toothpick and resuspended in 50 μl milliQ water. The sample was incubated for 10 minutes at 99° C. 5 μl of the incubated sample was used as a template for the PCR reaction, using Phusion® DNA polymerase (Finnzymes) according to the instructions provided by the supplier.

PCR Reaction Conditions:

| | | | |
|---|---|---|---|
| step 1 | 3' | 98° C. | |
| step 2 | 10" | 98° C. | |
| step 3 | 15" | 58° C. | repeat step 2 to 4 for 30 cycles |
| step 4 | 30" | 72° C. | |
| step 5 | 4' | 72° C. | |
| step 6 | 30" | 20° C. | |

Sample Pretreatment for Xylose Isomerase Activity Determinations (General herein and in Example 3)

0.5 ml of 0.1 M MOPS buffer (pH 7.5) was added to the cell pellet of an overnight culture. The cells were resuspended and transferred to a 2 ml Eppendorf tube which already contained 0.5 g of glassbeads with a diameter of 0.4-0.5 mm. All samples were vigorously shaken in an Eppendorf tube shaker (IKA VIBRAX-VXR) for 20 min at 4° C., at maximal speed. The extract was centrifuged for 5 minutes at 14000 rpm and 4° C. The supernatant, which is the cell free extract, was transferred into a fresh Eppendorf tube.

Assay Conditions Xylose Isomerase Activity Assay (General herein and as Determined in Example 3).

The following method is a modified version of the method described by Dische-Borenfreud (J. Biol. Chem. (1951) 192, 2, 583-587). One (1.0) ml of the substrate mix (100 mM MOPS pH 7.5, 10 mM $MgCl_2$, 10 mM D-xylose) was mixed with 50 μl (diluted) cell free extract, in duplicate, on ice. Subsequently the reaction tubes were placed in a 50° C. water bath for 30 minutes. In addition, the reactions were carried out at 30° C., also in duplicate. The reaction was stopped by placing the reaction tubes on ice water, followed by addition of 0.2 ml 1.67% L-cysteine monohydrate hydrochloride (Merck) solution. The mixture is then well mixed by vortexing. Subsequently, 6 ml of $H_2SO_4$ solution (190 ml water with 450 ml 95-97% concentrated $H_2SO_4$) was added, immediately followed by 0.2 ml of 0.12% (w/v) carbazole (Merck), dissolved in ethanol. This final mixture was mixed well by vortexing and left at room temperature for 60 min. The absorption is measured at 560 nm using plastic cuvettes.

D(+)-fructose, which is also a ketose, was used as a reference. To this end, approximately 1000 mg D-fructose was weighed accurately and dissolved in 0.1 M MOPs buffer, pH 7.5 in a 50 ml volumetric flask. A series of dilutions was made ranging from approximately 2 to 20 μmole/ml. 50 μl of these fructose solutions were used in the assay as described above and the absorption at 560 nm was used to make a calibration curve. The activity of the samples was calculated by relating the absorbance at 560 nm to the calibration curve.

The protein concentration of the sample was determined according to a modified protocol of the Bradford method, using the Coomassie Plus Protein Assay (Thermo Scientific). The specific activity of xylose isomerase is expressed as nmol/mg protein·min.

Example 1

Expression of Xylose Isomerase from *Bacteroides uniformis* ATCC 8492 in *Saccharomyces cerevisiae*

1.1.1 Construction of Xylose Isomerase Expression Vector

Xylose isomerase [E.C. 4.2.1.2], GenBank accession number AAYH02000036 (SEQ ID NO: 1) from *Bacteroides uniformis* ATCC 8492 was analysed for the codon usage. The codon use was optimized as described in WO2006/077258 and WO2008/000632 (SEQ ID NO: 2).

The gene according to SEQ ID NO:2 as cloned in front of the TPI1-promoter of *S. cerevisiae*. In order to prevent potential inefficient expression of the xylose isomerase, the following sequence (SEQ ID NO:22) was placed in front of the coding sequence: ACTAGTAAAAACACATACATAAAC-TAAAAATG, showing the start codon italicized, A SpeI restriction site (ACTAGT) was introduced in the strong, constitutive TPI1-promoter, changing the sequence TCTTGCTTAAATCTATAACTACAAAAAA-CACATACATAAAC TAAAAATG (SEQ ID NO:23; original TPI1 promoter) into TCTTGCTTAAATCTATAACTAG-TAAAAACACATACATAAAC TAAAAATG (SEQ ID NO:24).

This allows for operably linking the codon optimized xylose isomerase coding sequence to the TPI1-promoter.

In addition, the termination codon TAA was changed into TAAG, which is the most efficient termination codon in yeast. Convenient restriction sites were added to facilitate cloning. The sequence is synthesized by GeneArt AG (Regensburg, Germany).

Figure 1:
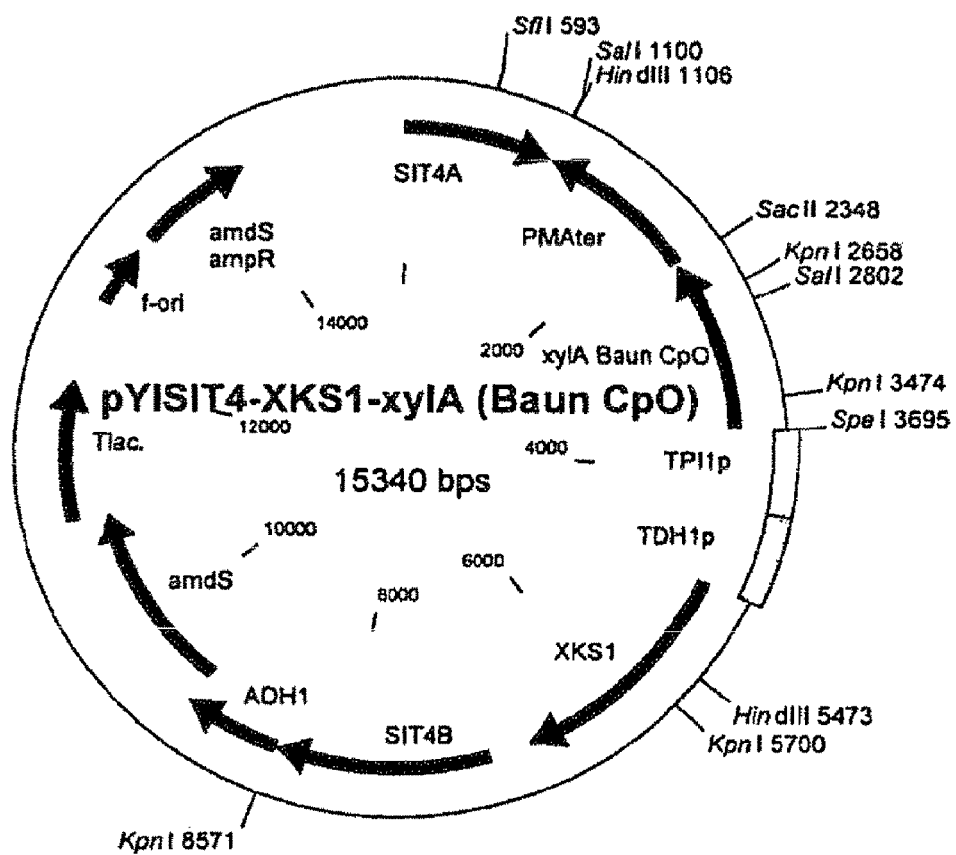
FIG. 1 sets out the plasmid map of pYISIT4-XKS1-xylA (Baun CpO) encoding xylose isomerase from *Bacteroides uniformis* ATCC 8492 for expression in *Saccharomyces cerevisiae*. CpO denotes codon pair optimized.

The final yeast expression construct pYISIT4-XKS1-xylA (Baun CpO) is set out in FIG. 1.

1.2 Yeast Transformation

*S. cerevisiae* strain CEN.PK113-7D (MATa URA3 HIS3 LEU2 TRP1 MAL2-8 SUC2) and a derivative of CEN.PK113-7D, in which the GRE3-gene was replaced by the genes of the non-oxidative part of the pentose phosphate pathway (see above) (MATa URA3 HIS3 LEU2 TRP1 MAL2-8 SUC2 GRE3::[TPI1p-TAL1-ADH1p-TKL1-PGI1p-RPE1-ENO1p-RIK1]) are transformed with the construct pYISIT4-XKS1-xylA (Baun CpO). Transformation mixtures are plated on Yeast Carbon Base (YCB) w/o ammonium sulphate (Difco), 40 mM KPi (pH 6.8) and 5 mM acetamide. Untransformed cells cannot grow on this medium.

Transformants are characterized using PCR techniques and/or Southern blotting techniques.

Example 2

Growth of Transformed Yeast Strains on Xylose 2.1 Medium Composition

Growth experiments: *Saccharomyces cerevisiae* strains are grown on medium having the following composition: 0.67% (w/v) yeast nitrogen base and either glucose, galactose or xylose, or a combination of these substrates (see below). For agar plates the medium is supplemented with 2% (w/v) bacteriological agar.

Ethanol production: Shake-flask cultivations were performed at 30° C. in a synthetic medium (Verduyn et al., Yeast 8:501-517, 1992). The pH of the medium was adjusted to 6.0 with 2 M KOH prior to sterilisation. For solid synthetic medium, 1.5% of agar was added.

Pre-cultures were prepared by inoculating 100 ml medium containing the appropriate sugar in a 500-ml shake flask with a frozen stock culture. After incubation at 30° C. in an orbital shaker (200 rpm), this culture was used to inoculate either shake-flask cultures. The synthetic medium for anaerobic cultivation was supplemented with 0.01 g I-1 ergosterol and 0.42 g I-1 Tween 80 dissolved in ethanol (Andreasen and Stier. J. Cell Physiol. 41:23-36, 1953; and Andreasen and Stier. J. Cell Physiol. 43:271-281, 1954).

2.2 Growth Experiments

*Saccharomyces cerevisiae* strain CEN.PK113-7D or the derivative constitutively expressing the PPP (see Example 1), transformed with pYISIT4-XKS1-xylA (Baun CpO), are grown on agar plates with 2% glucose as carbon source. When colonies are visible, single colonies are used to inoculate liquid medium with 100 mM xylose, 100 mM glucose and 100 mM galactose as carbon sources, or combinations thereof. Growth is monitored by measuring the increase in optical density at 600 nm on a LKB Ultrospec K spectrophotometer.

2.3 Ethanol production

*Saccharomyces cerevisiae* strain CEN.PK113-7D or the derivative constitutively expressing the PPP (see Example 1), transformed with pYISIT4-XKS1-xylA (Baun CpO), are grown on agar plates with 2% glucose as carbon source. When colonies were visible, single colonies are used to inoculate a synthetic medium (Verduyn et al., supra). Mixtures of glucose, xylose and or galactose are added to the medium as a carbon source, ranging from 0 to 50 grams per liter. Growth is monitored by measuring the increase in optical density at 600 nm on a LKB Ultrospec K spectrophotometer. Ethanol production and sugar consumption in time are monitored by HPLC and/or NMR analysis.

Example 3

3.1 Introduction of Four Constitutively Expressed Genes of the Non-Oxidative Pentose Phosphate Pathway

Figure 2:
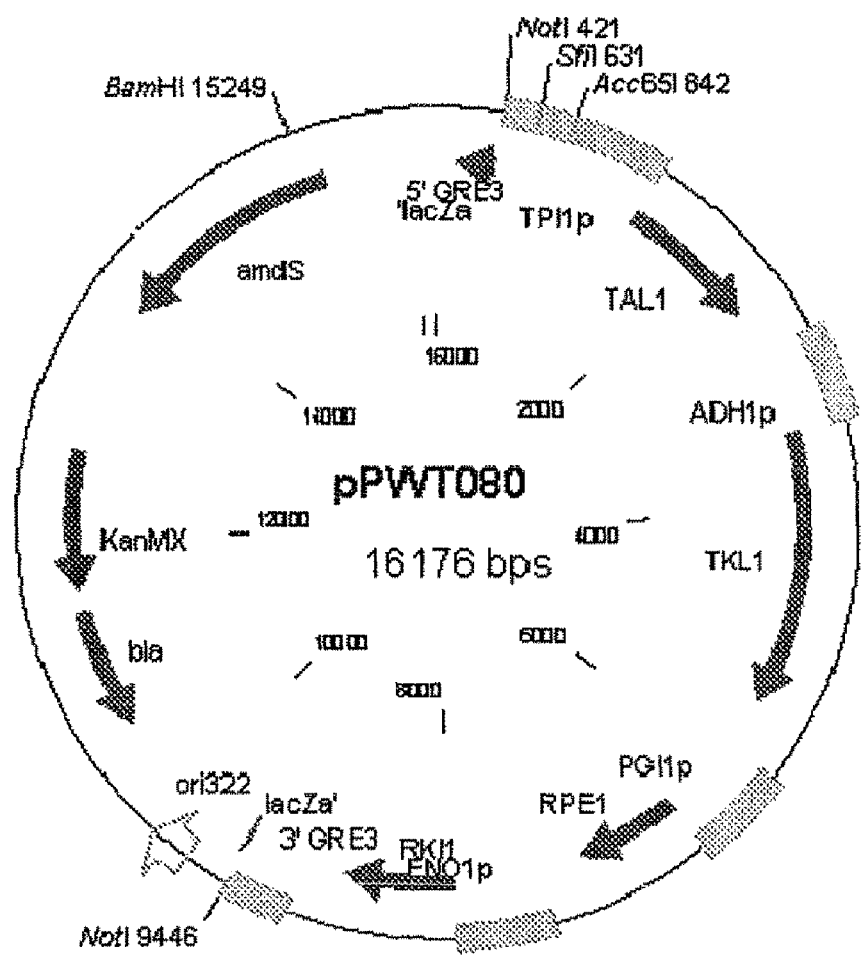
FIG. 2 sets out a physical map of plasmid pPWT080, the sequence of which is given in SEQ ID no. 4.

*Saccharomyces cerevisiae* BIE104P1, expressing the genes TAL1, TKL1, RKI1 and RPE1 constitutively, was obtained by transforming CEN.PK113-7D (MATa URA3 HIS3 LEU2 TRP1 MAL2-8 SUC2) with plasmid pPWT080 (FIG. 2). To a large extent, plasmid pPWT080 was constructed by using synthetic DNA, synthesized by GeneArt AG (Regensburg, Germany). The sequence of plasmid pPWT080 is set out in SEQ ID 4. In short, plasmid pPWT080 consists of the promoter region of the GRE3-gene, followed by the four PPP-genes TAL1, TKL1, RKI1 and RPE1 under control of strong constitutive promoters, and the 3' non-coding sequences of the GRE3-gene, as set out in FIG. 2. As selectable markers, the kanMX-gene conferring resistance to G418 and the *Aspergillus* amdS-gene allowing the transformants to grow in acetamide as sole nitrogen source are present on this plasmid. Upon integration, followed by intramolecular recombination, the markers are lost and the integration of this construct leads to inactivation of the coding region of the GRE3-gene and the overexpression of the genes TAL1, TKL1, RPE1 and RKI1.

Prior to the transformation of CEN.PK113-7D, pPWT080 was linearized using the restriction enzyme SfiI (New England Biolabs), according to the instructions provided by the supplier. Transformation mixtures were plated on YPD (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

The integration of plasmid pPWT080 is directed to the GRE3-locus. Transformants were characterized using PCR and Southern blotting techniques.

Figure 3:
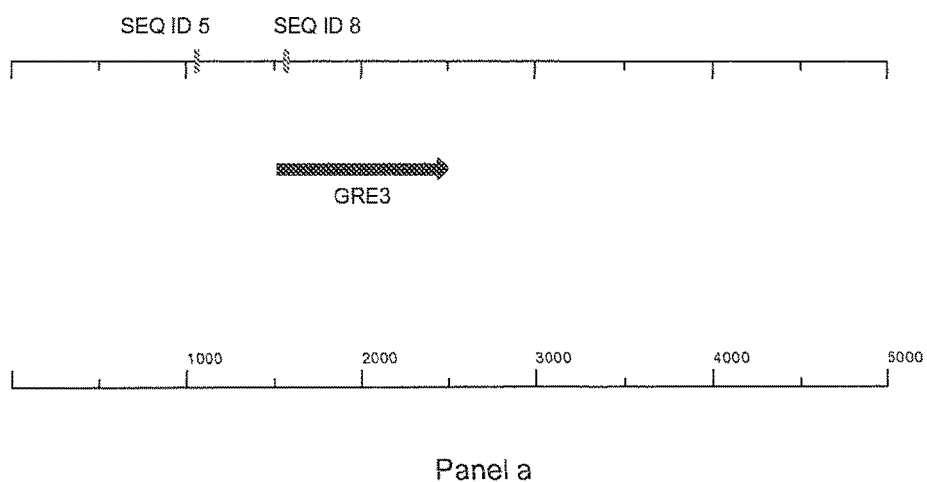
FIG. 3 sets out a physical map of the wild-type GRE3-locus (panel a) and a one copy integration of PWT080 in the GRE3-locus (panel b, showing where the primers bind and panel c, showing where the RKI1-probe binds)
Figure 3:
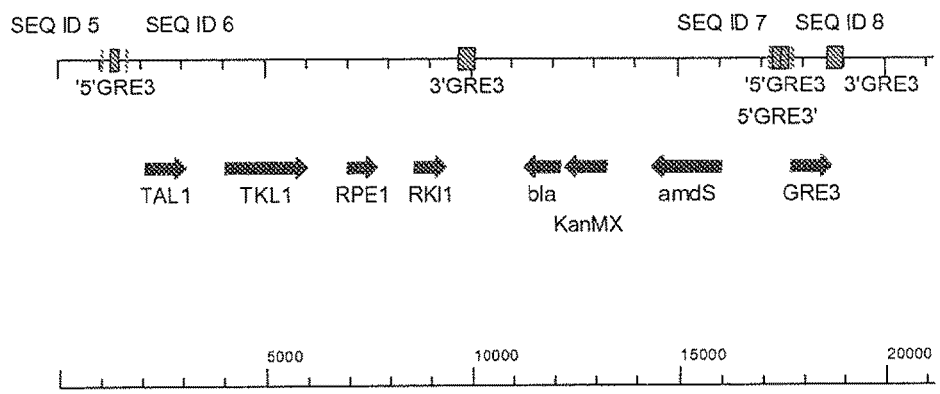
Figure 3:
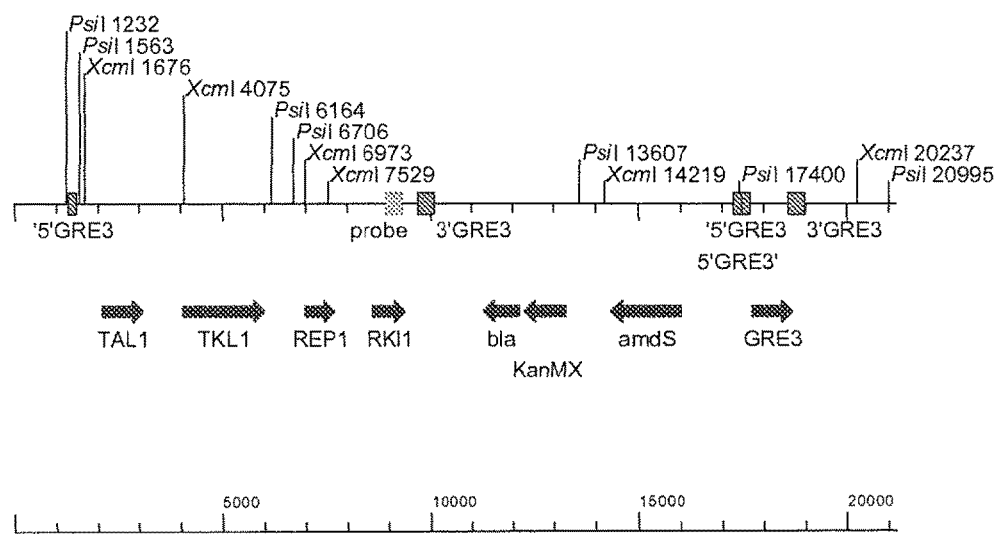

PCR reactions, which are indicative for the correct integration of one copy of plasmid pPWT080, were performed with the primers indicated by SEQ ID 5 and 6, and 6 and 7 (see FIG. 3). With the primer pairs of SEQ ID 5 and 6, the correct integration at the GRE3-locus was checked. If plasmid pPWT080 was integrated in multiple copies (head-to-tail integration), the primer pair of SEQ ID 6 and 7 will give a PCR-product. If the latter PCR product is absent, this is indicative for a one copy integration.

In order to verify the correct one copy integration in transformants identified as such using the above described PCR technique, a Southern blot analysis was performed. To this end, the chromosomal DNA was isolated from the wild-type strain CEN.PK113-7D and transformants using standard molecular biology techniques. The chromosomal DNA was digested with the restriction enzymes XcmI and PsiI, electroforesed over a 0.7% agarose gel and the DNA was transferred to a nylon membrane (Hybond N+, Amersham Pharmacia Biotech) according to the instructions of the manufacturer.

As a probe for detecting the correct integration of the plasmid pPWT080, a probe derived from the RKI1-gene, present in plasmid pPWT080, was used. The probe was made by using the primers of SEQ ID 9 and 10 and plasmid pPWT080 as a template. The labeling of the probe and the subsequent hybridization and washing procedures were performed as suggested by the supplier of the ECL Direct Labeling and Detection System (GE Life Sciences).

Figure 4:
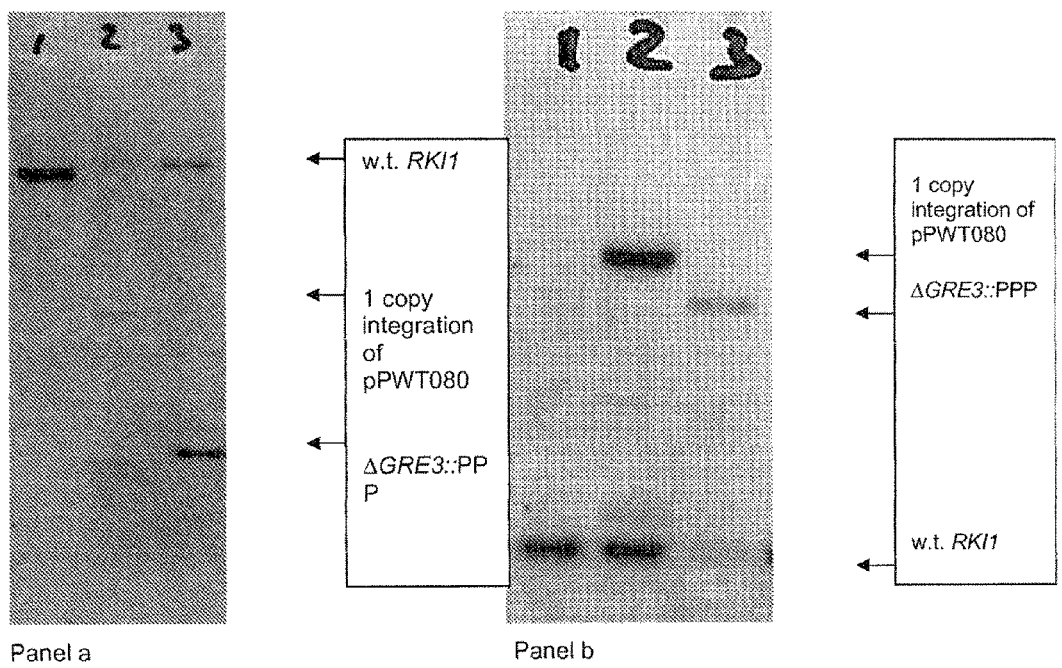
FIG. 4 sets out an Autoradiogram showing the correct integration of one copy of the plasmid pPWT080 in CEN.PK113-7D.

The autoradiogram, as presented in FIG. 4, shows correct integration of one copy of plasmid pPWT080, in accordance with the expected hybridisation pattern as can be deduced from FIG. 3 (panel c). The strain was designated BIE104F1.

In order to be able to introduce the genes encoding xylose isomerase and xylulokinase (section 3.2), it is necessary to remove the selection markers introduced by the integration of plasmid pPWT080. The design of plasmid pPWT080 was such, that upon integration of pPWT080 in the chromosome, homologous sequences are in close proximity of each other. This design allows the selectable markers to be lost by spontaneous intramolecular recombination of these homologous regions. The removal of the markers from the strain results in a marker free strain that is more stable in its use, than a strain containing markers. More specifically, the promoter region of the GRE3-gene and the 3' non-coding region of the GRE3-gene are duplicated after integration of one copy of pPWT080 at the GRE3-locus of S. cerevisiae. Upon vegetative growth, intramolecular recombination will take place, although at low frequency. The frequency of this recombination depends on the length of the homology and the locus in the genome (unpublished results). Upon sequential transfer of a subfraction of the culture to fresh medium, intramolecular recombinants will accumulate in time.

To this end, strain BIE104F1 was cultured in YPD-2% glucose, starting from a colony isolate. 25 µl of an overnight culture was used to inoculate fresh YPD-2% glucose medium. After five serial transfers, the optical density of the culture was determined and cells were diluted to a concentration of approximately 5000 per ml. 100 µl of the cell suspension was plated on Yeast Carbon Base medium (Difco) containing 30 mM KPi (pH 6.8), 0.1% $(NH_4)_2SO_4$, 40 mM fluoro-acetamide (Amersham) and 1.8% agar (Difco). Cells identical to cells of strain BIE104F1, i.e. without intracellular recombination, still contain the amdS-gene. To those cells, fluoro-acetamide is toxic. These cells will not be able to grow and will not form colonies on a medium containing fluoro-acetamide. However, if intramolecular recombination has occurred, BIE104F1-variants that have lost the selectable markers will be able to grow on the fluoro-acetamide medium, since they are unable to convert fluoro-acetamide into growth inhibiting compounds. Those cells will form colonies on this agar medium.

The thus obtained fluoro-acetamide resistant colonies were subjected to PCR analysis using primers of SEQ ID 5 and 6, and 7 and 8. Primers of SEQ ID 5 and 6 will give a band if recombination of the selectable markers has taken place as intended, as set out in FIG. 5. As a result, the coding region of the GRE3-gene is replaced by the four genes TKL1, TAL1, RKI1 and RPE1. In that case, a PCR reaction using primers of SEQ ID 7 and 8 should not result in a PCR product, since primer 7 primes in a region that should be out-recombined (see FIG. 3, panel b). If a band is obtained with these primers, this is indicative for the presence of the complete plasmid pPWT080 in the genome, so no recombination has taken place.

If primers of SEQ ID 5 and 6 do not result in a PCR product, recombination has taken place, but in such a way that the complete plasmid pPWT080 has recombined out of the genome. Not only were the selectable markers lost, but also the four PPP-genes. In fact, wild-type yeast has been retrieved.

Isolates that exhibited the expected PCR results, were subjected to Southern blot analysis (vide supra). The result is presented in FIG. 4. One of the strains that showed the correct pattern of bands on the Southern blot (as can be deduced from FIG. 3) is the strain designated as BIE104P1.

3.2 Introduction of Constitutively Expressed Genes Encoding Xylose Isomerase and Xylulokinase Plasmid pYISIT4-XKS1-xylA (Baun CpO), as set out in FIG. 1, was improved in order to allow for G418 selection of the transformants. To this end, a 4630 by insert containing the xylA-gene under control of the TPI1-promoter and the XKS1-gene under control of the TDH1-promoter was excised from plasmid pYISIT4-XKS1-xylA (Baun) (FIG. 1), using the restriction enzymes MluI and SacI.

Plasmid pYI#SIT4, as set out in FIG. 6, was digested with restriction enzyme Acc65I.

The kanamycin-resistance marker (kanMX) present on plasmid p427TEF (Dualsystems Biotech AG), allowing selection in E. coli (kanamycin) and S. cerevisiae (G418) was isolated by PCR using primers of SEQ ID 11 and 12. The sequence of primer of SEQ ID 12 was designed in such a way that the MluI-site in the kanMX-fragment was lost, which keeps the MluI-site in the resulting plasmid (pPWT007, see below) unique. The PCR product was subcloned in the pCRII-TOPO vector using the Zero Blunt® TOPO PCR Cloning Kit for Sub-cloning (Invitrogen). Correct clones were used to excise the kanMX-resistance marker using the restriction enzyme Acc65I. Ligation of this fragment with the digested plasmid pYI#SIT4 resulted in pPWT007, which is set out in FIG. 7.

Plasmid pPWT007 was cleaved with the restriction enzymes MluI and SacI. After clean-up of this vector, the above described 4630 by MluI-SacII fragment of pYISIT4-XKS1-xylA (Baun) was ligated. The resulting plasmid is called pPWT042, which is set out in FIG. 8.

Strain BIE104P1 (MATa URA3 HIS3 LEU2 TRP1 MAL2-8 SUC2 ΔGRE3::[TPI1p-TAL1-ADH1p-TKL1-PGI1p-RPE1-ENO1p-RKI1]) (see section 3.1) was transformed with plasmid pPWT042. Prior to the transformation of BIE104P1, pPWT042 was linearized using the restriction enzyme SfiI, according to the instructions provided by the supplier. Transformation mixtures were plated on YPD (per liter: 10 grams of yeast extract, 20 grams per liter peptone, 20 grams per liter dextrose, 20 grams of agar) containing 100 µg G418 (Sigma Aldrich) per ml.

After two to four days, colonies appeared on the plates, whereas the negative control (i.e. no addition of DNA in the transformation experiment) resulted in blank YPD/G418-plates.

Upon digestion of plasmid pPWT042 with SfiI, its integration is directed to the S/T4-locus (Gottlin-Ninfa and Kaback (1986) Molecular and Cellular Biology Vol. 6, No. 6, 2185-2197) in the genome. Transformants were characterized using PCR and Southernblotting techniques.

PCR reactions, using Phusion® DNA polymerase (Finnzymes), which are indicative for the correct integration of one copy of plasmid pPWT042, were performed with the primers indicated by SEQ IDs 13 and 14, and 14 and 15.

As set out in FIG. 9, with primer pair SEQ ID 13 and 14, the correct integration at the S/T4-locus was checked. The correct integration of the plasmid in the S/T4-locus may also be checked with primer pair SEQ ID 15 and 16 (FIG. 9). If plasmid pPWT042 was integrated in multiple copies (head-to-tail integration), the primer pair of SEQ ID 14 and 15 will give a PCR-product. If the latter PCR product is absent, this is indicative for one copy integration of plasmid pPWT042

A strain with one copy of plasmid pPWT042 integrated into the genome was designated BIE104P1Y9.

3.3 Growth Experiments

Single colony isolates of strains BIE104P1 and BIE104P1Y9 were used to inoculate YNB-medium (Difco) supplemented with 2% glucose. The inoculated flasks were incubated for approximately 16 hours at 30° C. and 280 rpm. The optical density at 600 nm of the overnight cultures was determined. YNB-medium supplemented with 1% glucose and 1% xylose was inoculated with the overnight cultures at a starting OD600 of 0.2. Cells were grown overnight at 30° C. and 280 rpm. Subsequently, YNB medium containing 2% xylose and 0.1% glucose were inoculated at a starting OD600 of 0.2.

The minute amount of glucose present in the latter medium was consumed rapidly by both strains. Upon transfer to YNB with 2% xylose as sole carbon source, at a starting OD600 of 0.2, only BIE104P1Y9 was able to grow on this medium after a very long lag phase of approximately 4 weeks. If the optical density at 600 nm reached a value of at least 2.0, the cells were transferred to a flask with fresh YNB-medium containing 2% xylose, at a starting OD600 of 0.2.

This was repeated a number of times, as is set it in FIG. 10. The graph clearly shows that strain BIE104P1Y9 grows rapidly and efficiently on a mineral medium containing 2% xylose as sole carbon source, while a reference strain, missing the integrated plasmid pPWT042, is not capable of doing so.

3.4 Xylose Isomerase Activity

Single colony isolates of strains BIE104P1 and BIE104P1Y9 were used to inoculate YPD 2% glucose. The inoculated flasks were incubated for approximately 16 hours at 30° C. and 280 rpm. The optical density at 600 nm of the overnight cultures was determined. Cells were harvested by centrifugation. The pellet was washed once with 0.1 M MOPS (3-(N-morpholino)propanesulfonic acid; Sigma) buffer, pH 7.5 and frozen at −20° C. until the analysis was performed.

The results of the analysis are summarized in the table below.

| Strain | XI-activity at 30° C. (nmol/mg protein · min) | XI-activity at 50° C. (nmol/mg protein · min) |
|---|---|---|
| Reference strain BIE104P1 | <20 | <20 |
| BIE104P1Y9 | 110 | 640 |

The values are the average of two independent experiments.

3.5 Ethanol Production

Single colony isolates of strains BIE104P1 and BIE104P1Y9 were used to inoculate Verduyn-medium (Verduyn et al., Yeast 8:501-517, 1992) supplemented with 2% glucose as sole carbon source. In addition, strain BIE104P1Y9 was inoculated in Verduyn-medium with 2% xylose as sole carbon source. The inoculated flasks were incubated for approximately 64 hours at 30° C. and 280 rpm. The optical density at 600 nm of the cultures was determined. The cells were harvested by centrifugation and the cell pellet was washed with sterile milliQ water (Millipore).

Fresh Verduyn-medium supplemented with 2% glucose and 2% xylose was inoculated with the three precultures described above. The amount of cells inoculated was such that the initial OD600 was 0.2. The flasks were closed with waterlocks, ensuring anaerobic growth conditions after the oxygen was exhausted from the medium and head space.

The flasks were incubated for 72 hours at 30° C. and 280 rpm. Samples were taken at 23, 47 and 71 hours for analysis. The following analyses were performed: OD600 determination, NMR analysis (xylose, glucose, ethanol, acetic acid and glycerol). The results are shown in FIGS. 11 and 12 and the tale below. The data represent the residual amount of sugars at the indicated (glucose and xylose in grams per liter) and the formation of (by-)products (ethanol, glycerol and acetic acid).

In FIG. 11, the development of the optical density at 600 nm (OD600) in time is shown. The reference strain, BIE104P1, reaches its maximum OD600 before or at 23 h after the start of the experiment. Apparently, at or before the 23 h time point, the glucose has been exhausted from the medium (FIG. 12, panel a). Also, the ethanol production has reached its maximum at the moment the glucose has been consumed by this yeast strain. Both growth and ethanol production seize, because this strain cannot utilize and ferment xylose, for it misses the necessary active proteins (i.e. a xylose isomerase and overexpressed xylulokinase).

Strain BIE104P1Y9 however, in which the xylose isomerase derived from *Bacteroides uniformis* and the native xylulokinase are overexpressed, is capable of growing on and fermenting xylose into ethanol (FIGS. 11 and 12). After approximately 1 day of anaerobic cultivation, strain BIE104P1Y9 already consumed some xylose, while all glucose was already consumed. Subsequently, the residual amount of glucose was fermented into ethanol, as is apparent from FIG. 12 (panel b and c) and the table below. By-product formation (actetic acid and glycerol) is low, as is apparent from the table below.

The results are not (significantly) influenced by the precultures (glucose or xylose), as is apparent from the results presented in FIGS. 11 and 12.

| BIE104P1 pregrown on glucose | | | | | |
|---|---|---|---|---|---|
| Time (h) | Glucose | Xylose | Glycerol | Acetic Acid | Ethanol |
| 0 | 19.5 | 19.6 | 0.0 | 0.0 | 0.7 |
| 23 | 0.0 | 20.8 | 0.5 | 0.3 | 9.0 |
| 47 | 0.0 | 20.7 | 0.7 | 0.7 | 8.8 |
| 71 | 0.0 | 19.9 | 0.7 | 0.9 | 8.4 |

| BIE104P1Y9 pregrown on glucose | | | | | |
|---|---|---|---|---|---|
| Time (h) | Glucose | Xylose | Glycerol | Acetic Acid | Ethanol |
| 0 | 19.5 | 19.6 | 0.0 | 0.0 | 0.7 |
| 23 | 0.0 | 16.6 | 0.6 | 0.5 | 11.4 |
| 47 | 0.0 | 6.3 | 0.7 | 0.8 | 14.3 |
| 71 | 0.0 | 1.7 | 0.4 | 1.1 | 16.8 |

| BIE104P1Y9 pregrown on xylose | | | | | |
|---|---|---|---|---|---|
| Time (h) | Glucose | Xylose | Glycerol | Acetic Acid | Ethanol |
| 0 | 19.5 | 19.6 | 0.0 | 0.0 | 0.7 |
| 23 | 0.7 | 17.7 | 0.0 | 0.5 | 11.3 |

-continued

| BIE104P1Y9 pregrown on xylose | | | | | |
|---|---|---|---|---|---|
| Time (h) | Glucose | Xylose | Glycerol | Acetic Acid | Ethanol |
| 47 | 0.0 | 6.1 | 0.7 | 0.8 | 14.9 |
| 71 | 0.0 | 1.1 | 0.5 | 1.1 | 16.7 |

All values are given in grams per liter.

Based on these results, a Qs of 363 mg xylose per gram biomass, per hour was calculated (time interval 23-47 hours; optical density of 30 equals to 6 grams of dry matter per liter), in case of strain BIE104P1Y9 pregrown on xylose.

EXAMPLE 4

4.1 Introduction of the Genes araA, araB and araD into the Genome of *S. cerevisiae*

Plasmid pPWT018, as set out in FIG. 13, was constructed as follows: vector pPWT006 (FIG. 14), consisting of a SIT2-locus (Gottlin-Ninfa and Kaback (1986) Molecular and Cell Biology vol. 6, no. 6, 2185-2197) and the markers allowing for selection of transformants on the antibiotic G418 and the ability to grow on acetamide (vide supra), was digested with the restriction enzymes BsiWI and MluI. The genes encoding arabinose isomerase (araA), L-ribulokinase (araB) and L-ribulose-5-phosphate-4-epimerase (araD) from *Lactobacillus plantarum*, as disclosed in patent application WO2008/041840, were synthesized by GeneArt AG (Regensburg, Germany). One large fragment was synthesized, harbouring the three ara-genes mentioned above, under control of (or operably linked to) strong promoters from *S. cerevisiae*, i.e. the TDH3-promoter controlling the expression of the araA-gene, the ENO1-promoter controlling the araB-gene and the PGI1-promoter controlling the araD-gene. This fragment was surrounded by the unique restriction enzymes Acc65I and MluI. Cloning of this fragment into pPWT006 digested with MluI and BsiWI, resulted in plasmid pPWT018 (FIG. 13). The sequence of plasmid pPWT018 is set out in SEQ ID 17.

CEN.PK113-7D (MATa URA3 HIS3 LEU2 TRP1 MAL2-8 SUC2) was transformed with plasmid pPWT018, which was previously linearized with SfiI (New England Biolabs), according to the instructions of the supplier. A synthetic SfiI-site was designed in the 5'-flank of the SIT2-gene (see FIG. 13). Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

The integration of plasmid pPWT018 is directed to the SIT2-locus. Transformants were characterized using PCR and Southern blotting techniques.

PCR reactions, which are indicative for the correct integration of one copy of plasmid pPWT018, were performed with the primers indicated by SEQ ID 18 and 15, and 15 and 14 (see FIG. 3). With the primer pairs of SEQ ID 18 and 15, the correct integration at the SIT2-locus was checked. If plasmid pPWT018 was integrated in multiple copies (head-to-tail integration), the primer pair of SEQ ID 15 and 14 will give a PCR-product. If the latter PCR product is absent, this is indicative for one copy integration of pPWT018. A strain in which one copy of plasmid pPWT018 was integrated in the SIT2-locus was designated BIE104R2.

In order to be able to transform the yeast strain with other constructs, it is necessary to remove the selectable markers. The design of plasmid pPWT018 was such, that upon integration of pPWT018 in the chromosome, homologous sequences are in close proximity of each other. This design allows the selectable markers to be lost by spontaneous intramolecular recombination of these homologous regions.

Upon vegetative growth, intramolecular recombination will take place, although at low frequency. The frequency of this recombination depends on the length of the homology and the locus in the genome (unpublished results). Upon sequential transfer of a subfraction of the culture to fresh medium, intramolecular recombinants will accumulate in time.

To this end, strain BIE104R2 was cultured in YPD-medium (per liter: 10 grams of yeast extract, 20 grams per liter peptone, 20 grams per liter dextrose), starting from a single colony isolate. 25 μl of an overnight culture was used to inoculate fresh YPD medium. After at least five of such serial transfers, the optical density of the culture was determined and cells were diluted to a concentration of approximately 5000 per ml. 100 μl of the cell suspension was plated on Yeast Carbon Base medium (Difco) containing 30 mM KPi (pH 6.8), 0.1% $(NH_4)_2SO_4$, 40 mM fluoro-acetamide (Amersham) and 1.8% agar (Difco). Cells identical to cells of strain BIE104R2, i.e. without intracellular recombination, still contain the amdS-gene. To those cells, fluoro-acetamide is toxic. These cells will not be able to grow and will not form colonies on a medium containing fluoro-acetamide. However, if intramolecular recombination has occurred, BIE104R2-variants that have lost the selectable markers will be able to grow on the fluoro-acetamide medium, since they are unable to convert fluoro-acetamide into growth inhibiting compounds. Those cells will form colonies on this agar medium.

The thus obtained fluoro-acetamide resistant colonies were subjected to PCR analysis using primers of SEQ ID 18 and 15, and 14 and 19. Primers of SEQ ID 18 and will give a band if recombination of the selectable markers has taken place as intended. As a result, the cassette with the genes araA, araB and araD under control of the strong yeast promoters have been integrated in the SIT2-locus of the genome of the host strain. In that case, a PCR reaction using primers of SEQ ID 14 and 19 should not result in a PCR product, since primer 14 primes in a region that should be out-recombined. If a band is obtained with the latter primers, this is indicative for the presence of the complete plasmid pPWT018 in the genome, so no recombination has taken place.

If primers of SEQ ID 18 and 15 do not result in a PCR product, recombination has taken place, but in such a way that the complete plasmid pPWT018 has recombined out of the genome. Not only were the selectable markers lost, but also the ara-genes. In fact, wild-type yeast has been retrieved.

Isolates that showed PCR results in accordance with one copy integration of pPWT018 were subjected to Southern blot analysis. The chromosomal DNA of strains CEN.PK113-7D and the correct recombinants were digested with EcoRI and HindIII (double digestion). A SIT2-probe was prepared with primers of SEQ ID 20 and 21, using pPW018 as a template. The result of the hybridisation experiment is shown in FIG. 15. The expected hybridisation pattern may be deduced from the physical maps as set out in FIG. 16 (panels a and b).

In the wild-type strain, a band of 2.35 kb is observed, which is in accordance with the expected size (FIG. 16, panel a). Upon integration and partial loss by recombination of the plasmid pPWT018, a band of 1.06 kb was expected (FIG. 16, panel b). Indeed, this band is observed, as shown in FIG. 15 (lane 2).

One of the strains that showed the correct pattern of bands on the Southern blot (as can be deduced from FIG. 15) is the strain designated as BIE104A2.

4.2 Introduction of Four Constitutively Expressed Genes of the Non-Oxidative Pentose Phosphate Pathway

*Saccharomyces cerevisiae* BIE104A2, expressing the genes araA, araB and araD constitutively, was transformed with plasmid pPWT080 (FIG. 2). The procedure and results were already described in Example 3 (section 3.1). In short, BIE104A2 was transformed with SfiI-digested pPWT080. Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

The integration of plasmid pPWT080 is directed to the GRE3-locus. Transformants were characterized using PCR and Southern blotting techniques, as described in Example 3, section 3.1.

A transformant showing correct integration of one copy of plasmid pPWT080, in accordance with the expected hybridisation pattern, was designated BIE104A2F1.

In order to be able to introduce the genes encoding xylose isomerase and xylulokinase (section 3.2), it is necessary to remove the selection markers introduced by the integration of plasmid pPWT080. To this end, strain BIE104A2F1 was cultured in YPD-medium, starting from a colony isolate. 25 μl of an overnight culture was used to inoculate fresh YPD-medium. After five serial transfers, the optical density of the culture was determined and cells were diluted to a concentration of approximately 5000 per ml. 100 μl of the cell suspension was plated on Yeast Carbon Base medium (Difco) containing 30 mM KPi (pH 6.8), 0.1% $(NH_4)_2SO_4$, 40 mM fluoro-acetamide (Amersham) and 1.8% agar (Difco). Fluoro-acetamide resistant colonies were subjected to PCR analysis and, in case of correct PCR-profiles, Southern blot analysis (section 3.1 of Example 3). One of the strains that showed the correct pattern of bands on the Southern blot is the strain designated as BIE104A2P1.

4.3 Introduction of Constitutively Expressed Genes Encoding Xylose Isomerase and Xylulokinase Strain BIE104A2P1 (MATa URA3 HIS3 LEU2 TRP1 MAL2-8 SUC2 SIT2::[TDH3-araA, ENO1-araB, PGI1-araD] ΔGRE3::[TPI1p-TAL1, ADH1p-TKL1, PGI1p-RPE1, ENO1p-RIK1]) was transformed with plasmid pPWT042. Prior to the transformation of BIE104A2P1, pPWT042 was linearized using the restriction enzyme SfiI, according to the instructions provided by the supplier. Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

Upon digestion of plasmid pPWT042 with SfiI, its integration is directed to the SIT4-locus (Gottlin-Ninfa and Kaback (1986) Molecular and Cellular Biology Vol. 6, No. 6, 2185-2197) in the genome. Transformants were characterized using PCR and Southernblotting techniques, as described in Example 3 (section 3.2).

A strain with one copy of plasmid pPWT042 integrated into the genome was designated BIE104A2P1Y9.

4.4 Growth Experiments

Single colony isolates of strains BIE104A2P1Y9 were used to inoculate YNB-medium (Difco) supplemented with 2% glucose or 2% galactose. The inoculated flasks were incubated at 30° C. and 280 rpm until the optical density at 600 nm reached a value of at least 2.0.

YNB-medium supplemented with 1% arabinose and 1% xylose was inoculated with the overnight cultures at a starting OD600 of 0.2. Cells were grown at 30° C. and 280 rpm. The optical density at 600 nm was monitored regularly. When the optical density reached a value larger than 2.0, an aliquot of the culture was transferred to fresh YNB medium containing 2% xylose and 0.2% arabinose. The amount of cells added was such that the starting OD600 of the culture was 0.2.

The optical density was monitored regularly. The results are shown in FIG. 17, panel a (precultures on galactose) and panel b (precultures on glucose).

The results clearly show that the strains are capable of utilizing both arabinose and xylose.

The invention claimed is:

1. A cell which comprises a nucleotide sequence encoding a xylose isomerase, wherein the amino acid sequence of the xylose isomerase has at least about 94% sequence identity to the amino acid sequence set out in SEQ ID NO:3 and wherein the nucleotide sequence is heterologous to the host.

2. The cell according to claim 1 which is a eukaryotic cell.

3. The cell according to claim 1 which is a yeast cell.

4. The cell according to claim 3 which is a yeast cell of the genus *Saccharomyces, Kluyveromyces, Candida, Pichia, Schizosaccharomyces, Hansenula, Klockera, Schwanniomyces* or *Yarrowia*.

5. The cell according to claim 4, wherein the yeast cell is of the species *S. cerevisiae, S. bulderi, S. bametti, S. exiguus, S. uvarum, S. diastaticus, K. lactis, K. marxianus* or *K. fragifis*.

6. The cell according to claim 1 which is a filamentous fungal cell.

7. The cell according to claim 6 wherein the filamentous fungal cell is of the genus *Aspergillus, Penicillium, Rhizopus, Trichoderma, Humicola, Acremonium* or *Fusarium*.

8. The cell according to claim 7, wherein the filamentous fungus cell is of the species *Aspergillus niger, Aspergillus oryzae, Penicillium chrysogenum*, or *Rhizopus oryzae*.

9. The cell according to claim 1, wherein the cell comprises one or more genetic modifications,
wherein the one or more genetic modifications result in overexpression of at least one gene encoding a ribulose-5-phosphate isomerase, a ribulose-5-phosphate epimerase, a transketolase, a transaldolase, or a xylulose kinase.

10. The cell according to claim 9, wherein the one or more genetic modifications result in overexpression of at least the genes encoding a transketolase and a transaldolase.

11. The cell according to claim 9, wherein the one or more genetic modifications result in overexpression of a gene encoding a xylulose kinase.

12. The cell according to claim 9, wherein the gene that is overexpressed is a gene which is endogenous to the cell.

13. The cell according to claim 9, wherein said cell is a *S. cerevisiae* cell, said one or more genetic modifications is to GRE3, and wherein the one or more genetic modifications reduces the expression or the activity of said GRE3.

14. The cell according to claim 13, wherein the gene is inactivated by deletion of at least part of the gene or by disruption of the gene.

15. The cell according to claim 9, wherein the TAL1 transaldolase, TKL1 transketolase, RPE1 ribulose-5-phosphate epimerase, and RKI1 ribose-5-phosphate isomerase genes are overexpressed.

16. The cell according to claim 9, wherein the coding region of the GRE3 aldose reductase gene is inactivated by replacement of the coding region with a nucleotide sequence comprising the TAL1 transaldolase, TKL1 transketolase, RPE1 ribulose-5-phosphate epimerase, and RKI1 ribose-5-phosphate isomerase genes.

17. The cell according to claim 9, wherein the araA L-arabinose isomerase, araB L-ribulokinase, and araD L-ribulose-5-P-epimerase genes from *Lactobacillus plantarum* are expressed.

18. The cell according to claim 9, wherein all expressed genes are constitutively expressed.

19. The cell according to claim 18 wherein one or more constitutively expressed genes are stably integrated into the genome of the cell.

20. The cell according to claim 19, wherein all constitutively expressed genes are stably integrated into the genome of the cell.

21. The cell according to claim 1 which has the ability to grow on L-arabinose.

22. The cell according to claim 21 wherein said cell produces a fermentation product.

23. A process for producing a fermentation product which process comprises fermenting a medium containing at least a source of xylose and a source of L-arabinose with a cell as defined in claim 22 such that the cell ferments xylose and L-arabinose to the fermentation product.

24. The cell according to claim 1 wherein said cell produces a fermentation product.

25. A process for producing a fermentation product which process comprises fermenting a medium containing a source of xylose with the cell according to claim 24 such that the cell ferments xylose to the fermentation product.

26. A process for producing a fermentation product which process comprises fermenting a medium containing at least a source of xylose and a source of L-arabinose with a cell as defined in claim 24 and a cell able to use L-arabinose, whereby each cell ferments xylose and/or arabinose to the fermentation product.

27. The process according to claim 26, wherein the fermentation product is selected from the group consisting of ethanol, butanol, lactic acid, 3-hydroxypropionic acid, acrylic acid, acetic acid, succinic acid, citric acid, malic acid, fumaric acid, itaconic acid, an amino acid, 1,3-propane-diol, ethylene, glycerol, butanol, a β-lactam antibiotic and a cephalosporin.

28. The process according to claim 25, which comprises recovering the fermentation product.

29. The process according to claim 25 wherein the medium also contains a source of glucose.

30. The process according to claim 25, wherein the process is anaerobic.

31. The process according to claim 25, wherein the process is aerobic.

32. The process according to claim 31, wherein the process is performed under oxygen limited conditions wherein the rate of oxygen consumption is at least about 5.5 mmol/L/h.

* * * * *